United States Patent
Tatani et al.

(10) Patent No.: US 8,680,120 B2
(45) Date of Patent: *Mar. 25, 2014

(54) INDOLE DERIVATIVE OR PHARMACEUTICALLY ACCEPTABLE SALT THEREOF

(75) Inventors: Kazuya Tatani, Azumino (JP); Naohiro Kawamura, Azumino (JP); Tatsuhiro Kondo, Joetsu (JP); Atsushi Kondo, Azumino (JP)

(73) Assignee: Kissei Pharmaceutical Co., Ltd., Nagano (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/387,266

(22) PCT Filed: Jul. 26, 2010

(86) PCT No.: PCT/JP2010/062533
§ 371 (c)(1),
(2), (4) Date: Jan. 26, 2012

(87) PCT Pub. No.: WO2011/013624
PCT Pub. Date: Feb. 3, 2011

(65) Prior Publication Data
US 2012/0129890 A1 May 24, 2012

(30) Foreign Application Priority Data

Jul. 27, 2009 (JP) .................. 2009-173862
Nov. 4, 2009 (JP) .................. 2009-252862

(51) Int. Cl.
| A61K 31/444 | (2006.01) |
| A61K 31/4439 | (2006.01) |
| C07D 401/14 | (2006.01) |
| C07D 401/06 | (2006.01) |
| C07D 401/04 | (2006.01) |
| C07D 209/08 | (2006.01) |
| C07D 209/10 | (2006.01) |
| C07D 405/06 | (2006.01) |
| C07D 405/14 | (2006.01) |
| C07D 405/04 | (2006.01) |

(52) U.S. Cl.
USPC .......... 514/333; 514/339; 514/414; 514/415; 546/256; 546/271.4; 546/277.4; 548/465; 548/466; 548/511

(58) Field of Classification Search
None
See application file for complete search history.

(56) References Cited

U.S. PATENT DOCUMENTS

| 4,510,158 A | 4/1985 | Bailey |
| 6,486,153 B1 | 11/2002 | Castro Pineiro et al. |
| 2004/0186148 A1 | 9/2004 | Shankar et al. |
| 2005/0215589 A1 | 9/2005 | Crossley et al. |
| 2007/0232682 A1 | 10/2007 | Beard et al. |
| 2010/0144821 A1 | 6/2010 | Carter et al. |
| 2011/0082129 A1 | 4/2011 | Adams et al. |
| 2012/0040974 A1 | 2/2012 | Jorgensen et al. |

FOREIGN PATENT DOCUMENTS

| WO | WO 98/51667 A1 | 11/1998 | |
| WO | 2007/112322 A2 | 10/2007 | |
| WO | 2008/058402 A1 | 5/2008 | |
| WO | WO 2008/137609 | * 11/2008 | .......... C07D 209/26 |
| WO | 2009/156462 A2 | 12/2009 | |
| WO | WO 2009/156462 | * 12/2009 | .......... C07D 401/04 |
| WO | 2010/021693 A2 | 2/2010 | |

OTHER PUBLICATIONS

Johns Hopkins Medicine, Health Alerts, "BPH (Benign Prostatic Hyperplasia)." Accessed May 26, 2009, <http://www.johnshopkinshealthalerts.com/symptoms_remedies/benign_prostatic_hyperplasia/2077-1.html>.*
Swierzewski, Stanley J. "Urologic Emergencies: Acute Urinary Retention, Risk Factors, Causes, Treatment." Published Jun. 10, 1998. Accessed May 26, 2009. <http://www.urologychannel.com/emergencies/acute.shtml>.*
Adrian Hall, et al., "Discovery of a Novel Indole Series of EP1, Receptor Antagonists by Scaffold Hopping", Bioorganic and Medicinal Chemistry Letters, 2008, pp. 2684-2690, vol. 18, No. 8.
International Search Report of PCT/JP2010/062533 dated Sep. 7, 2010.
European Search Report issued in application No. 10 80 4370 dated Nov. 22, 2012.

* cited by examiner

Primary Examiner — Alicia L Otton
(74) Attorney, Agent, or Firm — Sughrue Mion, PLLC

(57) ABSTRACT

A compound (I) of the present invention, which has an $EP_1$ receptor antagonism:

[Chem.]

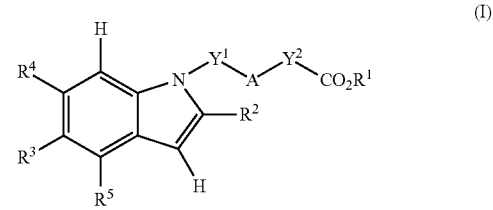

(I)

[wherein A represents a benzene ring or the like; $Y^1$ represents a $C_{1-6}$ alkylene group; $Y^2$ represents a single bond or the like; $R^1$ represents a hydrogen atom, a $C_{1-6}$ alkyl group or the like; $R^2$ represents a phenyl group which may have a substituent, a 5-membered aromatic heterocyclic ring which may have a substituent, a 6-membered aromatic heterocyclic ring which may have a substituent or the like; $R^3$ represents a halogen atom, a $C_{1-6}$ alkoxy group or the like; $R^4$ represents a hydrogen atom or the like; and $R^5$ represents a hydrogen atom or the like] or a pharmaceutically acceptable salt thereof is provided. Furthermore, the compound (I) of the present invention can be used as an agent for treating or preventing LUTS, in particular, various symptoms of OABs.

10 Claims, No Drawings

INDOLE DERIVATIVE OR PHARMACEUTICALLY ACCEPTABLE SALT THEREOF

CROSS REFERENCE TO RELATED APPLICATIONS

This application is a National Stage of International Application No. PCT/JP2010/062533 filed Jul. 26, 2010, claiming priority based on Japanese Patent Application Nos. 2009-2009-173862 filed Jul. 27, 2009 and 2009-252862 filed Nov. 4, 2009, the contents of all of which are incorporated herein by reference in their entirety.

TECHNICAL FIELD

The present invention relates to an indole derivative having an $EP_1$ receptor antagonism, which is useful as a pharmaceutical, or a pharmaceutically acceptable salt thereof, a pharmaceutical composition comprising the same, and a pharmaceutical use thereof.

BACKGROUND ART

With an increasingly aging and stressed society, the number of patients with lower urinary tract dysfunction (LUTD) has increased. LUTD is a generic term for urine collection disorder and dysuria, and the symptoms derived from LUTD are lower urinary tract symptoms (LUTS). One of the LUTS is an overactive bladder syndrome (OABs). OABs may be generally called overactive bladder (OAB) in some cases. In any case, it is a disease defined as "a symptom syndrome which essentially has urinary urgency and which is usually accompanied by urinary frequency and nocturia. Urge urinary incontinence is not necessary". The symptoms associated with OABs interfere with general life such as work, daily life, mental activity, and the like, and thus lower the quality of life (QOL). Currently, a first choice drug as an agent for treating OABs is an anticholinergic agent. However, it is necessary for the anticholinergic agent to be used also in due consideration of an anti-muscarinic effect such as thirst and residual urine, and thus, is not always effective for all patients (see, for example, Non-patent literature 1). Under these circumstances, there is a demand for development of a therapeutic agent which has a different mechanism from that of the anticholinergic agent (see, for example, Non-patent literature 1).

Recently, in LUTS, particularly in OABs, the role of urothelium has attracted attention. For LUTS, it has become clear that various chemical mediators are released in the urothelial cells, which cause a micturition reflex through the receptors of bladder sensory nerve terminals. Among them, one of the chemical mediators, prostaglandin $E_2$ ($PGE_2$), binds with a prostaglandin E receptor 1 ($EP_1$ receptor) in the afferent nerves (especially C fibers) in the urothelium to increase the micturition reflex. In addition, $PGE_2$ binds with the $EP_1$ receptors present in the bladder smooth muscle to contract the bladder. In fact, it has been reported that the $EP_1$ receptor antagonists inhibit both of the increase in the micturition reflex and the increase in the afferent nerve activities by $PGE_2$ (see, for example, Non-patent literature 2 and Non-patent literature 3). From these, it is suggested that $PGE_2$ is involved in contraction of the bladder smooth muscle and increase in the bladder sensory nerves through the $EP_1$ receptors. Furthermore, it is reported that $EP_1$ receptor antagonists do not increase the amount of the residual urine, but increase the bladder capacity (see, for example, Non-patent literature 4).

There exist four subtypes, $EP_2$, $EP_3$, and $EP_4$ as well as $EP_1$, of the $PGE_2$ receptor. The $EP_1$ receptor exists in the lungs as well as the bladder and the urothelium, the skeletal muscle, the renal collecting duct, and the like (see, for example, Non-patent literature 2). Therefore, it is expected that by changing the selectivity of the subtypes of the $PGE_2$ receptor, the target organs of the drugs, or the target tissues, a therapeutic agent for desired diseases can be developed.

A compound represented by the general formula (A) is disclosed as a therapeutic drug for Alzheimer's disease (see, for example, Patent literature 1).

[Chem. 1]

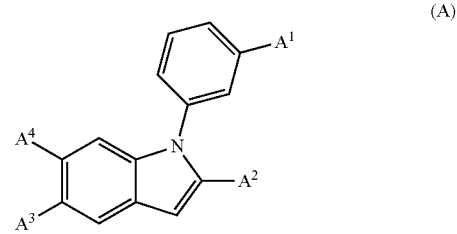

(A)

[wherein $A^1$ represents $-L-CO_2H$ or the like, $A^2$ represents a phenyl group which may have substituents, $A^3$ and $A^4$ independently represent a hydrogen atom, a halogen atom, an alkyl group, an alkoxy group, a haloalkyl group or a haloalkoxy group or the like, L represents $-(CH_2)n-(CH_2)n-$ or $-(CH_2)nO(CH_2)n-$ or the like, each n independently represents integer selected from 0 to 8].

However, there is no suggestion or disclosure that these compounds have an $EP_1$ receptor antagonism.

As an indole derivative having an $EP_1$ receptor antagonism, a compound represented by the chemical structural formula (B) (sodium 6-(6-chloro-3-isobutylindol-1-yl)pyridine-2-carboxylate) and a analog thereof are disclosed (see, for example, Non-patent literature 5).

[Chem. 2]

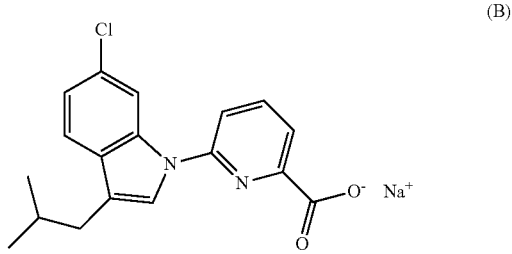

(B)

However, these compounds differ from the compounds of the present invention in the chemical structural formula in terms of the position, the type, or the like of a substituent.

CITATION LIST

Patent Literature

Patent literature 1: International publication WO2006/041874

Non-Patent Literature

Non-patent literature 1: Narihito Seki, "Folia Pharmacologia Japonica", 2007, Vol. 129, p. 368-373
Non-patent literature 2: Xiaojun Wang, et al., "Biomedical Research", 2008, Vol. 29, p. 105-111
Non-patent literature 3: Masahito Kawatani, "PAIN RESEARCH", 2004, Vol. 19, p. 185-190
Non-patent literature 4: Masanobu Maegawa, "The Journal of The Japan Neurogenic Bladder Society", 2008, Vol. 19, p. 169
Non-patent literature 5: Adrian Hall, et al., "Bioorganic & Medicinal Chemistry Letters", 2008, p. 2684-2690

SUMMARY OF THE INVENTION

Objects to be Solved by the Invention

The present invention is to provide a compound having an $EP_1$ receptor antagonism or a pharmaceutically acceptable salt thereof, a pharmaceutical composition comprising the same, and a pharmaceutical use thereof.

Means for Solving the Objects

The present inventors have conducted extensive studies on a compound having an $EP_1$ receptor antagonism, and as a result, they have found that the compounds (I) of the present invention or a pharmaceutically acceptable salt thereof exhibit a potent $EP_1$ receptor antagonism, thereby completing the present invention.

That is, the means for solving the above-described objects are presented below.

[1] A compound represented by the general formula (I) or a pharmaceutically acceptable salt thereof:

[Chem. 3]

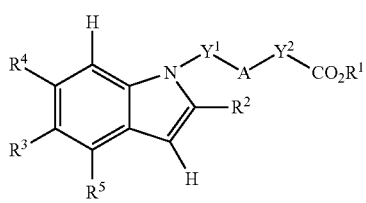
(I)

[wherein
A represents a group selected from the group consisting of the following a) to h):

[Chem. 4]

a) 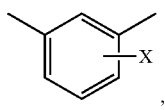, b) 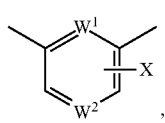, c) 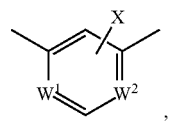, d) 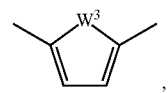, e) 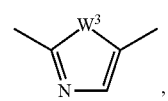, f) 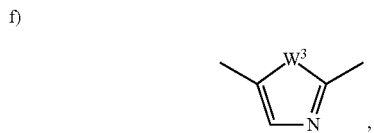, g) 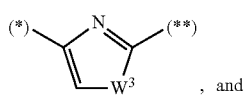, and h) 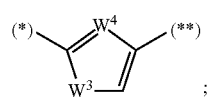;

one of $W^1$ and $W^2$ represents a nitrogen atom and the other represents =CH— or a nitrogen atom;
$W^3$ represents an oxygen atom or a sulfur atom;
$W^4$ represents =CH— or a nitrogen atom;
X represents a hydrogen atom or a halogen atom;
$Y^1$ represents a $C_{1-6}$ alkylene group;
$Y^2$ represents a single bond or an oxy-$C_{1-6}$ alkylene group;
$R^1$ represents a hydrogen atom, a $C_{1-6}$ alkyl group, or a $C_{7-10}$ aralkyl group;
$R^2$ represents a group selected from the group consisting of the following i) to n):
  i) a branched $C_{3-6}$ alkyl group,
  j) a halo-$C_{1-6}$ alkyl group,
  k) a $C_{3-6}$ cycloalkyl group,
  l) a phenyl group, in which the ring is unsubstituted or substituted with 1 to 5 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group,
  m) a 6-membered aromatic heterocyclic group, in which the ring is unsubstituted or substituted with 1 to 4 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group, and
  n) a 5-membered aromatic heterocyclic group, in which the ring is unsubstituted or substituted with 1 to 3 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group;

$R^3$ represents a halogen atom, a $C_{1-6}$ alkyl group, a halo-$C_{1-6}$ alkyl group, a hydroxy-$C_{1-6}$ alkyl group, a $C_{1-6}$ alkoxy group, a halo-$C_{1-6}$ alkoxy group, a $C_{1-6}$ alkylsulfanyl group, a $C_{3-6}$ cycloalkyl group, a cyano group, an amino group, or a nitro group;

$R^4$ represents a hydrogen atom, a halogen atom, a $C_{1-6}$ alkyl group, or a $C_{1-6}$ alkoxy group; and $R^5$ represents a hydrogen atom, a halogen atom, a $C_{1-6}$ alkyl group, or a $C_{1-6}$ alkoxy group;

with the proviso that the bonds with (*) represent binding to $Y^1$, and the bonds with (**) represent binding to $Y^2$].

[2] The compound or a pharmaceutically acceptable salt thereof as set forth in (1), wherein A is a group selected from the group consisting of the following a) to d):

[Chem. 5]

a)
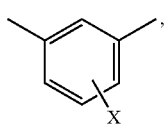

b)
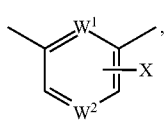

c)
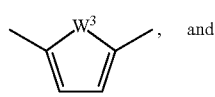

, and d)
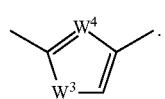

[3] The compound or a pharmaceutically acceptable salt thereof as set forth in (2), wherein A is a group selected from the group consisting of a) to c) below:

[Chem. 6]

a)
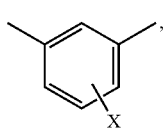

b)
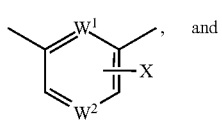

, and c)
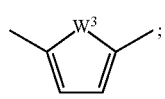

[4] The compound or a pharmaceutically acceptable salt thereof as set forth in (3), wherein $R^2$ is a group selected from the group consisting of the following a) to d):
a) a branched $C_{3-6}$ alkyl group,
b) a $C_{3-6}$ cycloalkyl group,
c) a phenyl group, and
d) a 5-membered aromatic heterocyclic group or a 6-membered aromatic heterocyclic group;
$R^4$ is a hydrogen atom or a halogen atom; and
$R^5$ is a hydrogen atom.

[5] The compound or a pharmaceutically acceptable salt thereof as set forth in (4), wherein $R^1$ is a hydrogen atom.

[6] The compound or a pharmaceutically acceptable salt thereof as set forth in (5), wherein A is a group selected from the group consisting of a) to e) below:

[Chem. 7]

a)
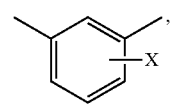

b)
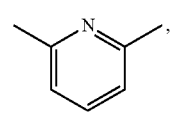

c)
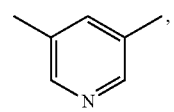

d)
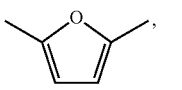

, and e)
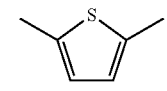

$Y^1$ is a methylene group and $Y^2$ is a single bond.

[7] The compound or a pharmaceutically acceptable salt thereof as set forth in (6), wherein $R^3$ is a $C_{1-6}$ alkoxy group.

[8] The compound or a pharmaceutically acceptable salt thereof as set forth in (7), wherein $R^3$ is a methoxy group.

[9] The compound or a pharmaceutically acceptable salt thereof as set forth in (6), wherein $R^3$ is a halogen atom.

[10] The compound or pharmaceutically acceptable salt thereof as set forth in (9), wherein $R^3$ is a fluorine atom.

[11] The compound or a pharmaceutically acceptable salt thereof as set forth in (6), wherein $R^3$ is a $C_{1-6}$ alkyl group.

[12] The compound or a pharmaceutically acceptable salt thereof as set forth in (11), wherein $R^3$ is a methyl group.

[13] The compound or a pharmaceutically acceptable salt thereof as set forth in (6), wherein $R^2$ is an isopropyl group, an isobutyl group, a sec-butyl group or a 1-ethylpropyl group.

[14] The compound or pharmaceutically acceptable salt thereof as set forth in (6), wherein $R^2$ is a phenyl group or a 5-membered aromatic heterocyclic group.

[15] The compound or pharmaceutically acceptable salt thereof as set forth in (14), wherein $R^2$ is a phenyl group, a 3-thienyl group or a 3-furyl group.

[16] The compound or a pharmaceutically acceptable salt thereof as set forth in (2), wherein A is a group represented by the following formula:

[Chem. 8]

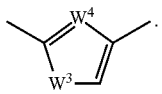

[17] The compound or a pharmaceutically acceptable salt thereof as set forth in (16), wherein $R^1$ is a hydrogen atom.
[18] The compound or a pharmaceutically acceptable salt thereof as set forth in (3), wherein $R^2$ is a group selected from the group consisting of the following a) to c):

[Chem. 9]

a)

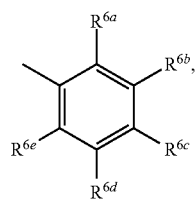

b)

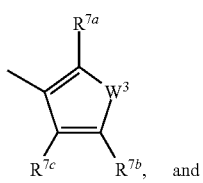

and c)

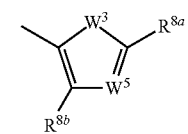

$W^5$ is a nitrogen atom or —$CR^{8c}$=;
$R^{6a}$, $R^{6b}$, $R^{6c}$, $R^{6d}$ and $R^{6e}$ are each independently a group selected from a hydrogen atom, a halogen atom, a $C_{1-6}$ alkyl group, a halo-$C_{1-6}$ alkyl group, a hydroxy-$C_{1-6}$ alkyl group, a $C_{1-6}$ alkoxy group, or a cyano group, with the proviso that all of $R^{6a}$, $R^{6b}$, $R^{6c}$, $R^{6d}$ and $R^{6e}$ are not simultaneously a hydrogen atom;
$R^{7a}$, $R^{7b}$ and $R^{7c}$ are each independently a hydrogen atom, a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, with the proviso that all of $R^{7a}$, $R^{7b}$ and $R^{7c}$ are not simultaneously a hydrogen atom; and
$R^{8a}$, $R^{8b}$ and $R^{8c}$ are each independently a hydrogen atom, a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, with the proviso that all of $R^{8a}$, $R^{8b}$ and $R^{8c}$ are not simultaneously a hydrogen atom.
[19] The compound or a pharmaceutically acceptable salt thereof as set forth in (18), wherein $R^1$ is a hydrogen atom.
[20] A pharmaceutical composition comprising the compound or a pharmaceutically acceptable salt thereof as set forth in any one of (1) to (19) as an active ingredient.

[21] An $EP_1$ receptor antagonist comprising the compound or a pharmaceutically acceptable salt thereof as set forth in any one of (1) to (19) as an active ingredient.
[22] An agent for treating or preventing lower urinary tract symptoms, comprising the compound or a pharmaceutically acceptable salt thereof as set forth in any one of (1) to (19) as an active ingredient.
[23] A method for preventing or treating lower urinary tract symptoms, comprising administering an effective amount of the compound as set forth in any one of (1) to (19) or a pharmaceutically acceptable salt thereof.
[24] A use of the compound as set forth in any one of (1) to (19) or a pharmaceutically acceptable salt thereof for the manufacture of a pharmaceutical composition for preventing or treating lower urinary tract symptoms.

Effects of the Invention

The compound (I) of the present invention or a pharmaceutically acceptable salt thereof exhibits a potent $EP_1$ receptor antagonism, for example, in a test for confirmation of an $EP_1$ receptor antagonism. Therefore, the compound (I) of the present invention or a pharmaceutically acceptable salt thereof is useful as an agent for treating or preventing lower urinary tract symptoms (LUTS), in particular, overactive bladder syndrome (OABs) or the like, based on its $EP_1$ receptor antagonism.

EMBODIMENTS FOR CARRYING OUT THE INVENTION

The terms in the specification are defined.
The "halogen atom" means a fluorine atom, a chlorine atom, a bromine atom, or an iodine atom. In X, a fluorine atom or a chlorine atom is preferable. In $R^3$, a fluorine atom or a chlorine atom is preferable, and a fluorine atom is more preferable.
The "$C_{1-6}$ alkyl group" means an alkyl group having 1 to 6 carbon atoms, which may be branched. Examples thereof include a methyl group, an ethyl group, a propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, a 2-methylbutyl group, a 1,2-dimethylpropyl group, an n-hexyl group, an isohexyl group and the like. In $R^3$, a methyl group or an ethyl group is preferable, and a methyl group is more preferable.
The "branched $C_{3-6}$ alkyl group" means a branched alkyl group having 3 to 6 carbon atoms. Examples thereof include an isopropyl group, an isobutyl group, a sec-butyl group, a tert-butyl group, an isopentyl group, a neopentyl group, a tert-pentyl group, a 1-methylbutyl group, a 2-methylbutyl group, a 1,2-dimethylpropyl group, a 1-ethylpropyl group, an isohexyl group, and the like. It is preferably an isopropyl group, an isobutyl group, a sec-butyl group or a 1-ethylpropyl group. It is more preferably an isopropyl group, a sec-butyl group, or a 1-ethylpropyl group. It is further preferably a sec-butyl group.
The "$C_{1-6}$ alkoxy group" means an alkoxy group having 1 to 6 carbon atoms, which may be branched. Examples thereof include a methoxy group, an ethoxy group, a propoxy group, an isopropoxy group, a butoxy group, an isobutoxy group, a sec-butoxy group, a tert-butoxy group, a pentyloxy group, a hexyloxy group and the like. In $R^3$, a methoxy group or an ethoxy group is preferable, and a methoxy group is more preferable.

The "halo-$C_{1-6}$ alkyl group" means a $C_{1-6}$ alkyl group substituted with the same or different 1 to 5 or 6 halogen atoms. Examples thereof include a monofluoromethyl group, a difluoromethyl group, a trifluoromethyl group, a 2-chloroethyl group, a 2-fluoroethyl group, a 2,2-difluoroethyl group, a 1,1-difluoroethyl group, a 1,2-difluoroethyl group, a 2,2,2-trifluoroethyl group, pentafluoroethyl group, a 2,2,2-trichloroethyl group, a 3-fluoropropyl group, a 2-fluoropropyl group, a 1-fluoropropyl group, a 3,3-difluoropropyl group, a 2,2-difluoropropyl group, a 1,1-difluoropropyl group, a 1-fluorobutyl group, a 1-fluoropentyl group, a 1-fluorohexyl group, a 2,2,2-trifluoro-1-trifluoromethyl-1-ethyl group and the like. It is preferably a monofluoromethyl group, a trifluoromethyl group or a 2-fluoroethyl group.

The "halo-$C_{1-6}$ alkoxy group" means a $C_{1-6}$ alkoxy group substituted with the same or different 1 to 5 halogen atoms. Examples thereof include a monofluoromethoxy group, a difluoromethoxy group, a trifluoromethoxy group, a 2-chloroethoxy group, a 2-fluoroethoxy group, a 2,2-difluoroethoxy group, a 1,1-difluoroethoxy group, a 1,2-difluoroethoxy group, a 2,2,2-trifluoroethoxy group, pentafluoroethoxy group, a 2,2,2-trichloroethoxy group, a 3-fluoropropoxy group, a 2-fluoropropoxy group, a 1-fluoropropoxy group, a 3,3-difluoropropoxy group, a 2,2-difluoropropoxy group, a 1,1-difluoropropoxy group, a 4-fluorobutoxy group, a 5-fluoropentyloxy group, a 6-fluorohexyloxy group and the like. It is preferably a monofluoromethoxy group, a difluoromethoxy group or a trifluoromethoxy group.

The "hydroxy-$C_{1-6}$ alkyl group" means a $C_{1-6}$ alkyl group substituted with a hydroxy group. Examples thereof include a hydroxymethyl group, a 1-hydroxyethyl group, a 1-hydroxy-1,1-dimethylmethyl group, a 2-hydroxyethyl group, a 2-hydroxy-2-methylpropyl group, a 3-hydroxypropyl group and the like.

The "$C_{1-6}$ alkylsulfanyl" means a group represented by ($C_{1-6}$ alkyl)-S—. Examples thereof include a methylsulfanyl group, an ethylsulfanyl group, a propylsulfanyl group, a butylsulfanyl group, a pentylsulfanyl group, a hexylsulfanyl group and the like.

The "$C_{3-6}$ cycloalkyl group" means a monocyclic saturated alicyclic hydrocarbon group having 3 to 6 carbon atoms. Examples thereof include a cyclopropyl group, a cyclobutyl group, a cyclopentyl group, a cyclohexyl group and the like. In $R^2$, it is preferably a cyclopropyl group or a cyclopentyl group. It is more preferably a cyclopropyl group.

The "$C_{7-10}$ aralkyl group" means an alkyl group having 1 to 4 carbon atoms, which is substituted with an aryl group. Examples thereof include a benzyl group, a phenethyl group, a 1-phenylethyl group, a 3-phenylpropyl group, a 4-phenylbutyl group and the like.

The "5- or 6-membered aromatic heterocyclic group" means a 5- or 6-membered ring group containing 1 to 4 heteroatoms selected from an oxygen atom, a nitrogen atom, and a sulfur atom in the ring. Examples thereof include a pyridyl group, a pyrimidinyl group, a pyrazinyl group, a pyridazinyl group, a furyl group, a pyrrolyl group, a thienyl group, an imidazolyl group, a pyrazolyl group, a 1,2,4-triazolyl group, an isothiazolyl group, an isoxazolyl group, an oxazolyl group, a thiazolyl group, a 1,3,4-oxadiazolyl group, a 1,2,4-oxadiazolyl group and the like. It is preferably a 5-membered aromatic heterocyclic group, and more preferably a 2-furyl group, a 3-furyl group, a 2-thienyl group or a 3-thienyl group. It is further preferably a 3-furyl group or a 3-thienyl group.

The "5-membered aromatic heterocyclic group" means a 5-membered ring group containing 1 to 4 hetero atoms selected from an oxygen atom, a nitrogen atom, and a sulfur atom in the ring. Examples thereof include a furyl group, pyrrolyl group, a thienyl group, an imidazolyl group, a pyrazolyl group, a 1,2,4-triazolyl group, an isothiazolyl group, an isoxazolyl group, an oxazolyl group, a thiazolyl group, a 1,3,4-oxadiazolyl group, a 1,2,4-oxadiazolyl group and the like. It is preferably a 2-furyl group, a 3-furyl group, a 2-thienyl group or a 3-thienyl group. It is more preferably a 3-furyl group or a 3-thienyl group.

The "6-membered aromatic heterocyclic group" means a 6-membered ring group containing 1 to 4 nitrogen atoms in the ring. Examples thereof include a pyridyl group, a pyrimidinyl group, a pyrazinyl group, a pyridazinyl group and the like. It is preferably a pyridyl group, and more preferably a 3-pyridyl group.

The "$C_{1-6}$ alkylene group" means a divalent linear or molecular-chained saturated hydrocarbon chain having 1 to 6 carbon atoms. Examples thereof include —CH$_2$—, —CH$_2$CH$_2$—, —CH(CH$_3$)—, —(CH$_2$)$_3$—, —CH(CH$_3$)CH$_2$—, —CH$_2$CH(CH$_3$)—, —CH(CH$_2$CH$_3$)—, —C(CH$_3$)$_2$—, —(CH$_2$)$_4$—, —CH(CH$_3$)—(CH$_2$)$_2$—, —(CH$_2$)$_2$—CH(CH$_3$)—, —CH(CH$_2$CH$_3$)—CH$_2$—, —C(CH$_3$)$_2$CH$_2$—, —CH$_2$—C(CH$_3$)$_2$—, —CH(CH$_3$)—CH(CH$_3$)—, —(CH$_2$)$_5$—, —CH(CH$_3$)—(CH$_2$)$_3$—, —C(CH$_3$)$_2$CH$_2$CH$_2$—, —(CH$_2$)$_6$—, —C(CH$_3$)$_2$(CH$_2$)$_3$— and the like.

The "$C_{1-5}$ alkylene group" means a divalent linear or molecular-chained saturated hydrocarbon chain having 1 to 5 carbon atoms. Examples thereof include —CH$_2$—, —(CH$_2$)$_2$—, —CH(CH$_3$)—, —(CH$_2$)$_3$—, —CH$_2$—CH(CH$_3$)—, —C(CH$_3$)$_2$—, —(CH$_2$)$_4$—, —(CH$_2$)$_5$— and the like.

The "oxy-$C_{1-6}$ alkylene group" means —O—CH$_2$—, —O—(CH$_2$)$_2$—, —CH$_2$—O—CH$_2$—, —(CH$_2$)$_2$—O—, —O—CH(CH$_3$)—, —CH(CH$_3$)—O—, —O—(CH$_2$)$_3$—, —(CH$_2$)$_3$—O—, —O—CH(CH$_3$)—CH$_2$—, —CH(CH$_3$)—CH$_2$—O—, —O—C(CH$_3$)$_2$—, —C(CH$_3$)$_2$—O—, —O—(CH$_2$)$_4$—, —O—(CH$_2$)$_5$— or —O—(CH$_2$)$_6$—. It is preferably —O—CH$_2$—, —CH$_2$—O—, —O—(CH$_2$)$_2$—, —O—CH(CH$_3$)—, —O—CH(CH$_3$)—CH$_2$— or —O—C(CH$_3$)$_2$—. It is more preferably —O—CH$_2$—, —O—CH(CH$_3$)— or —O—C(CH$_3$)$_2$—.

Hereinafter, the present invention is described in more detail.

In the case that one or more asymmetric carbon atoms exist in the compound (I) of the present invention, the present invention includes each of compounds in which the respective asymmetric carbon atoms are in an R configuration or S configuration, and compounds having any combination of the configurations. Also, the racemic compound, the racemic mixture, the singular enantiomer, and the diastereomer mixture are encompassed within the scope of the present invention. In the case that geometrical isomerism exists in the compound (I) of the present invention, the present invention includes any of the geometrical isomers.

The compound (I) of the present invention can be converted to a pharmaceutically acceptable salt thereof according to a usual method, as necessary. Such a salt may be presented as an acid addition salt or a salt with a base.

Examples of the acid addition salt include acid addition salts with mineral acids such as hydrochloric acid, hydrobromic acid, hydroiodic acid, sulfuric acid, nitric acid, phosphoric acid and the like, and acid addition salts with organic acids such as formic acid, acetic acid, trifluoroacetic acid, methanesulfonic acid, benzene sulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like.

Examples of the salt with a base include salts with inorganic bases, such as a sodium salt, a potassium salt, a calcium salt, a magnesium salt and the like, and salts with organic bases or the like such as piperidine, morpholine, pyrrolidine, arginine, lysine and the like.

In addition, the compound (I) of the present invention or a pharmaceutically acceptable salt thereof also encompasses hydrates, and solvates with pharmaceutically acceptable solvents such as ethanol and the like.

The "$EP_1$ receptor antagonism" as mentioned in the present invention means an action of inhibiting the binding of a prostaglandin $E_2$ ($PGE_2$) to a prostaglandin E receptor 1 ($EP_1$ receptor).

The $EP_1$ receptor antagonism reduces the influx amount of calcium into cells and thus decreased or suppressed the intracellular calcium concentration. As the result, the $EP_1$ receptor antagonism exhibits an action of relaxation of smooth muscles, inhibition of sensory nerve stimulation or the like. Particularly, the $EP_1$ receptor antagonist acts on the bladder, the urothelium or the like, whereby it is useful as an agent for treating or preventing LUTS, in particular, the symptoms of OABs or the like.

Furthermore, the $EP_1$ receptor antagonism can be evaluated based on the efficacy of inhibiting the influx amount of calcium into cells by stimulus of a $PGE_2$ to $EP_1$ receptor. This efficacy can be evaluated by an in vitro test or in vivo test in accordance with "Pharmacological Test Examples" described in JP2008-214224A.

Examples of the preferable substituents for the compound (I) of the present invention or a pharmaceutically acceptable salt thereof are as follows.

(I-1) A is preferably a benzene ring, a pyridine ring, a furan ring or a thiazole ring, and more preferably a benzene ring or a pyridine ring.

(I-2) $Y^1$ is preferably a methylene group, —$CH(CH_3)$—, or —$C(CH_3)_2$—, and more preferably a methylene group.

(I-3) $Y^2$ is preferably a single bond or —$OCH_2$—, and more preferably a single bond.

(I-4) $R^1$ is preferably a hydrogen atom or a $C_{1-6}$ alkyl group, and more preferably a hydrogen atom.

(I-5) $R^2$ is preferably an isopropyl group, an isobutyl group, a sec-butyl group, a 1-ethylpropyl group, a phenyl group, a 5-membered aromatic heterocyclic group, a 6-membered aromatic heterocyclic group, a phenyl group, in which the ring is substituted with 1 to 3 groups independently selected from the group consisting of a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group, a 6-membered aromatic heterocyclic group, in which the ring is substituted with 1 to 2 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group, or a 5-membered aromatic heterocyclic group, in which the ring is substituted with 1 to 2 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group. It is more preferably an isopropyl group, a sec-butyl group, a phenyl group, a 3-furyl group, a 3-thienyl group, or a group selected from the group consisting of the following a) to d):

[Chem. 10]

a)
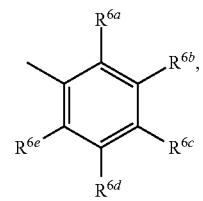

b)
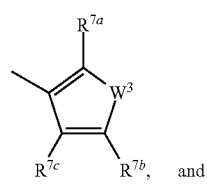
and c)
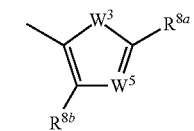

(wherein
$R^{6a}$, $R^{6b}$, $R^{6c}$, $R^{6d}$, and $R^{6e}$ are each a group selected from the group consisting of the following e) to g):
e) one group of $R^{6a}$, $R^{6b}$, $R^{6c}$, $R^{6d}$, and $R^{6e}$ is a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, and the other four groups are hydrogen atoms,
f) two groups of $R^{6a}$, $R^{6b}$, $R^{6c}$, $R^{6d}$, and $R^{6e}$ are each independently a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, and the other three groups are hydrogen atoms, and
g) three groups of $R^{6a}$, $R^{6b}$, $R^{6c}$, $R^{6d}$, and $R^{6e}$ are each independently a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, and the other two groups are hydrogen atoms;
$R^{7a}$, $R^{7b}$, and $R^{7c}$ are each a group selected from the group consisting of h) and i) below:
h) one group of $R^{7a}$, $R^{7b}$, and $R^{7c}$ is a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, and the other two groups are hydrogen atoms, and
i) two groups of $R^{7a}$, $R^{7b}$, and $R^{7c}$ are each independently a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, and the other is a hydrogen atom;
for $R^{8a}$ and $R^{8b}$, when $w^5$ is —$CR^{8c}$=, one group of $R^{8a}$, $R^{8b}$, and $R^{8c}$ is a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, the other two groups are hydrogen atoms, and when $w^5$ is a nitrogen atom, one group of $R^{8a}$ and $R^{8b}$ is a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, and the other group is a hydrogen atom). It is further preferably a 3-furyl group, a 3-thienyl group or a phenyl group.

(I-6) $R^3$ is preferably a fluorine atom, a chlorine atom, a methyl group, an ethyl group, a trifluoromethyl group, a methoxy group, an ethoxy group or a difluoromethoxy group, more preferably a fluorine atom, a chlorine atom, a methyl group, a methoxy group, an ethoxy group, or a difluoromethoxy group, further preferably a fluorine atom or a methoxy group, and particularly preferably a methoxy group.

(I-7) $R^4$ is preferably a hydrogen atom, a fluorine atom or a chlorine atom, and more preferably a hydrogen atom.

A preferable embodiment of the compound (I) of the present invention or a pharmaceutically acceptable salt thereof is a compound formed by combinations of preferable substituents described in (I-1) to (I-7).

Embodiment 1

A preferable embodiment of the present invention is as follows:
A is a following:

[Chem. 11]

a)

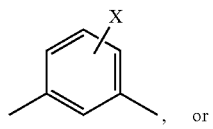
, or b)

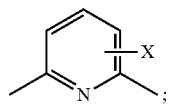
;

X is a hydrogen atom, a fluorine atom or a chlorine atom;
$Y^1$ is a methylene group;
$Y^2$ is a single bond or —O—CH$_2$—;
$R^1$ is a hydrogen atom;
$R^2$ is a phenyl group or a 5-membered aromatic heterocyclic group;
$R^3$ is a fluorine atom, a methyl group, a methoxy group or an ethoxy group; and
$R^4$ is a hydrogen atom, a fluorine atom or a chlorine atom.

Examples of the concrete compound included in the present embodiment include the following compounds:
3-(5-methoxy-2-phenylindol-1-ylmethyl)benzoic acid (Example 9-1), 3-(5-methyl-2-phenylindol-1-ylmethyl)benzoic acid (Example 9-13), 6-(5-methoxy-2-phenylindol-1-ylmethyl)pyridine-2-carboxylic acid (Example 9-21), 3-(5-methoxy-2-thiophen-3-ylindol-1-ylmethyl)benzoic acid (Example 9-25), 3-(2-furan-3-yl-5-methoxyindol-1-ylmethyl)benzoic acid (Example 9-32), 6-(5-methoxy-2-thiophen-3-ylindol-1-ylmethyl)pyridine-2-carboxylic acid (Example 9-35), 3-(6-fluoro-5-methoxy-2-phenylindol-1-ylmethyl)benzoic acid (Example 9-43), 2-fluoro-3-(5-methoxy-2-phenylindol-1-ylmethyl)benzoic acid (Example 9-44), 6-(6-chloro-5-methoxy-2-phenylindol-1-ylmethyl)pyridine-2-carboxylic acid (Example 25-9), 6-(5-methoxy-6-methyl-2-phenylindol-1-ylmethyl)pyridine-2-carboxylic acid (Example 25-16), 3-[2-(2-fluorophenyl)-5-methoxyindol-1-ylmethyl]benzoic acid (Example 25-17), 3-[2-(3-fluorophenyl)-5-methoxyindol-1-ylmethyl]benzoic acid (Example 25-18), 3-[2-(4-fluorophenyl)-5-methoxyindol-1-ylmethyl]benzoic acid (Example 25-19), 6-[6-chloro-2-(3-fluorophenyl)-5-methoxyindol-1-ylmethyl]pyridine-2-carboxylic acid (Example 25-23), 6-[6-fluoro-2-(2-fluorophenyl)-5-methoxyindol-1-ylmethyl]pyridine-2-carboxylic acid (Example 25-28), 6-[6-fluoro-2-(3-fluorophenyl)-5-methoxyindol-1-ylmethyl]pyridine-2-carboxylic acid (Example 25-29), 6-[6-fluoro-2-(4-fluorophenyl)-5-methoxyindol-1-ylmethyl]pyridine-2-carboxylic acid (Example 25-31), 6-(6-chloro-5-methoxy-2-thiophen-3-ylindol-1-ylmethyl)pyridine-2-carboxylic acid (Example 25-34), 6-(6-chloro-2-furan-3-yl-5-methoxyindol-1-ylmethyl)pyridine-2-carboxylic acid (Example 25-37), 6-(5-methoxy-6-methyl-2-thiophen-3-ylindol-1-ylmethyl)pyridine-2-carboxylic acid (Example 25-39), 6-[2-(2,5-difluorophenyl)-5-methoxyindol-1-ylmethyl)pyridine-2-carboxylic acid (Example 25-41).

Embodiment 2

Another preferable embodiment of the present invention is as follows:
A is a following:

[Chem. 12]

a)

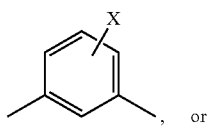
, or b)

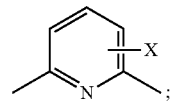
;

X is a hydrogen atom, a fluorine atom or a chlorine atom;
$Y^1$ is a methylene group;
$Y^2$ is a single bond or —O—CH$_2$—;
$R^1$ is a hydrogen atom;
$R^2$ is an isopropyl group or a sec-butyl group;
$R^3$ is a fluorine atom, a methyl group, a methoxy group or an ethoxy group; and
$R^4$ is a hydrogen atom, a fluorine atom or a chlorine atom.

Examples of the concrete compound included in the present embodiment include the following compounds:
3-(2-isopropyl-5-methoxyindol-1-ylmethyl)benzoic acid (Example 9-15), 6-[6-chloro-5-methoxy-2-(1-methylpropyl)indol-1-ylmethyl]pyridine-2-carboxylic acid (Example 25-44).

Embodiment 3

Another preferable embodiment of the present invention is as follows:
$R^1$ is a $C_{1-6}$ alkyl group.

Embodiment 4

Another preferable embodiment of the present invention is as follows:
A is a following:

[Chem. 13]

a)

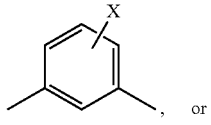
, or b)

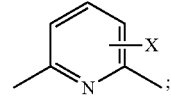
;

X is a hydrogen atom, a fluorine atom or a chlorine atom;
$Y^1$ is a methylene group;
$Y^2$ is a single bond or —O—$CH_2$—;
$R^1$ is a $C_{1-6}$ alkyl group;
$R^2$ is an isopropyl group, a sec-butyl group, a phenyl group or a 5-membered aromatic heterocyclic group;
$R^3$ is a fluorine atom, a chlorine atom, a methyl group, a methoxy group or an ethoxy group; and
$R^4$ is a hydrogen atom, a fluorine atom or a chlorine atom.

Embodiment 5

Another preferable embodiment of the present invention is as follows:
A is a following:

[Chem. 14]

a)

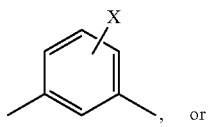, or b)

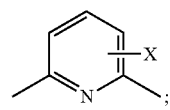;

X is a hydrogen atom, a fluorine atom or a chlorine atom;
$Y^1$ is a methylene group;
$Y^2$ is a single bond or —O—$CH_2$—;
$R^1$ is a hydrogen atom;
$R^2$ is a 6-membered aromatic heterocyclic group;
$R^3$ is a fluorine atom, a methyl group, a methoxy group or an ethoxy group; and
$R^4$ is a hydrogen atom, a fluorine atom or a chlorine atom.

Examples of the concrete compound included in the present embodiment include the following compounds:
3-(5-methoxy-2-pyridin-3-ylindol-1-ylmethyl)benzoic acid (Example 25-13), 6-(6-fluoro-5-methoxy-2-pyridin-3-ylindol-1-ylmethyl)pyridine-2-carboxylic acid (Example 25-33), 6-(6-chloro-5-methoxy-2-pyridin-3-ylindol-1-ylmethyl)pyridine-2-carboxylic acid (Example 25-42).

Embodiment 6

Another preferable embodiment of the present invention is as follows:
A is a following:

[Chem. 15]

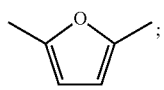;

$Y^1$ is a methylene group;
$Y^2$ is a single bond;
$R^1$ is a hydrogen atom;
$R^2$ is a phenyl group, which may have a substituent, or a 5-membered aromatic heterocyclic group, which may have a substituent;
$R^3$ is a fluorine atom, a methyl group, a methoxy group or an ethoxy group; and $R^4$ is a hydrogen atom, a fluorine atom, a chlorine atom or a methyl group.

Examples of the concrete compound included in the present embodiment include the following compounds:
5-[2-(3-fluorophenyl)-5-methoxyindol-1-ylmethyl]furan-2-carboxylic acid (Example 25-11), 5-[6 chloro-5-methoxy-2-phenylindol-1-ylmethyl]furan-2-carboxylic acid (Example 25-26), 5-[5-methoxy-6-methyl-2-phenylindol-1-ylmethyl]furan-2-carboxylic acid (Example 25-36), 5-(6-chloro-2-furan-3-yl-5-methoxyindol-1-ylmethyl)furan-2-carboxylic acid (Example 25-38).

Production Process of Compound (1) of the Present Invention

The compound (I) of the present invention or a pharmaceutically acceptable salt thereof can be prepared by a method described in the following Schemes 1 to 3, or a similar method thereto, or by a method described in other literature, or a similar method thereto.

[A] Synthesis of Compounds (Ia) to (Id)

The compound (I) of the present invention can be prepared by the method shown in Schemes 1 or 2 as compounds (Ia) to (Id). Further, when a protecting group is needed, combinations of introduction and cleavage can appropriately be carried out according to a usual method.

In the compound (I) of the present invention, the compound (Ia) wherein $R^1$ is a $C_{1-6}$ alkyl group or a $C_{7-10}$ aralkyl group, and the compound (Ib) wherein $R^1$ is a hydrogen atom can be prepared by each method shown in Scheme 1 or a similar method thereto, or be prepared according to a method described in other literature or a similar method thereto. Further, when a protective group is needed, combinations of introduction and cleavage can appropriately be carried out according to a usual method.

Scheme 1

[Chem.16]

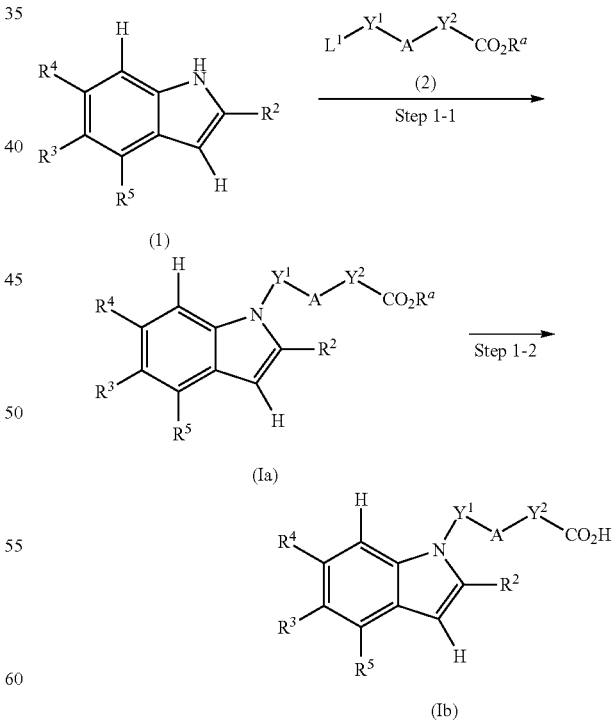

(wherein A, $R^2$, $R^3$, $R^4$, $R^5$, $Y^1$ and $Y^2$ have the same meanings as defined above; $R^a$ is a $C_{1-6}$ alkyl group or a $C_{7-10}$ aralkyl group; and $L^1$ represents a chlorine atom, a bromine atom, an iodine atom, a methanesulfonyloxy group or the like).

Step 1-1

A compound (Ia) can be prepared by reacting a compound (1) with a compound (2) in a solvent in the presence of a base. As the solvent to be used, N,N-dimethylformamide, N,N-dimethylacetamide, N,N-dimethylimidazolidinone, tetrahydrofuran, a mixed solvent thereof and the like can be illustrated. As the base to be used, sodium hydride, potassium tert-butoxide, lithium bis(trimethylsilyl)amide and the like can be illustrated. The reaction temperature is usually −20° C. to a solvent reflux temperature, and the reaction time varies depending on a starting material and a solvent to be used, a reaction temperature or the like, but it is usually 30 minutes to 3 days. Further, the present step can be carried out with addition of sodium iodide, tetra-n-butyl ammonium bromide, tetra-n-butyl ammonium iodide or the like, if necessary.

Furthermore, the compound (2) used in the present step may be commercially available. Further the compound (2) can be obtained by using the corresponding alcohol as a starting material and converting the hydroxy group into a chlorine atom, a bromine atom, an iodine atom, a methanesulfonyloxy group or the like according to a method described in literature or a similar method thereto.

Step 1-2

A compound (Ib) of the present invention can be prepared by treating the compound (Ia) of the present invention according to a conversion method from an ester group to a carboxy group. Such method is well-known to a skilled person in the art, and can be carried out using the method described in "Greene's Protective Groups in Organic Synthesis", edited by Greene & Wuts, fourth edition, Wiley-Interscience, 2006.

In the compound (I) of the present invention, the compounds (Ic) and (Id), wherein $R^2$ is a phenyl group, a 5 or 6-membered aromatic heterocyclic group, a phenyl group, in which the ring is substituted with 1 to 5 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group, a 6-membered aromatic heterocyclic group, in which the ring is substituted with 1 to 4 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group, or a 5-membered aromatic heterocyclic group, in which the ring is substituted with 1 to 3 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group can be prepared by the method shown in Scheme 2 or a similar method thereto, or can be prepared according to a method described in other literature or a similar method thereto. Further, when a protective group is needed, combinations of introduction and cleavage can appropriately be carried out according to a usual method.

Scheme 2

[Chem.17]

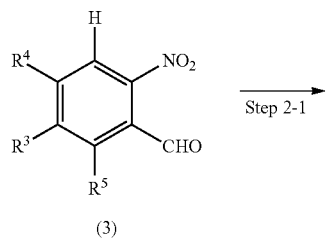

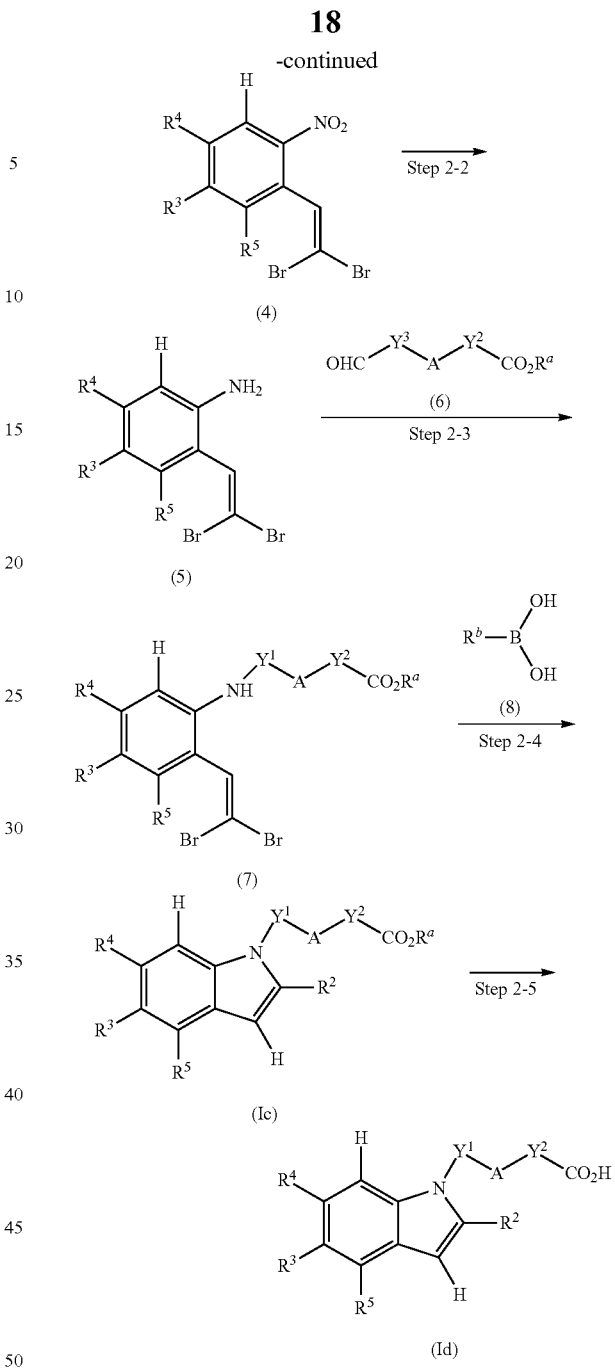

(wherein A, $R^3$, $R^4$, $R^5$, $R^a$, $Y^1$ and $Y^2$ have the same meanings as defined above; $R^b$ is a phenyl group, a 5 or 6-membered aromatic heterocyclic group, a phenyl group, in which the ring is substituted with 1 to 5 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group, a 6-membered aromatic heterocyclic group, in which the ring is substituted with 1 to 4 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group, or a 5-membered aromatic heterocyclic group, in which the ring is substituted with 1 to 3 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group; and $Y^3$ represents a single bond or a $C_{1-5}$ alkylene group).

Step 2-1

A compound (4) can be prepared by reacting a compound (3) with carbon tetrabromide and triphenylphosphine in a solvent. As the solvent to be used, dichloromethane, 1,2-dichloroethane, benzene, toluene, tetrahydrofuran, a mixed solvent thereof, and the like can be illustrated. The reaction temperature is usually from −20° C. to a solvent reflux temperature, and the reaction time varies depending on a starting material and a solvent to be used, a reaction temperature or the like, but it is usually 30 minutes to 3 days. Furthermore, the compound (3) used in the present step may be commercially available or can be prepared according to a method described in other literature or a similar method thereto.

Step 2-2

A compound (5) can be prepared by reducing a nitro group of the compound (4) using a reducing agent. As the reduction method of a nitro group, for example, a method using iron, zinc, tin(II) chloride dihydrate or the like as a reducing agent in a solvent can be illustrated. As the solvent to be used, methanol, ethanol, acetic acid, water, a mixed solvent thereof and the like can be illustrated. The reaction temperature is usually from −20° C. to a solvent reflux temperature, and the reaction time varies depending on a starting material and a solvent to be used, a reaction temperature or the like, but it is usually 30 minutes to 3 days.

Step 2-3

A compound (7) can be prepared by a reductive amination reaction using the compound (5) and the compound (6). As the solvent to be used, tetrahydrofuran, dichloromethane, 1,2-dichloroethane, ethanol, a mixed solvent thereof and the like can be illustrated. As the reducing agent to be used, sodium triacetoxyborohydride, sodium cyanoborohydride and the like can be, illustrated. The reaction temperature is usually from −20° C. to a solvent reflux temperature, and the reaction time varies depending on a starting material and a solvent to be used, a reaction temperature or the like, but it is usually 30 minutes to 3 days. Furthermore, the compound (6) used in the present step may be commercially available or can be prepared according to a method described in other literature or a similar method thereto.

Step 2-4

A compound (Ic) of the present invention can be prepared by reacting the compound (7) with a compound (8) in a solvent in the presence of a palladium catalyst and a base. As the solvent to be used, toluene, tetrahydrofuran, 1,4-dioxane, ethanol, N,N-dimethylformamide, water, a mixed solvent thereof and the like can be illustrated. As the palladium catalyst to be used, palladium (II) acetate, bis(triphenylphosphine)palladium (II) dichloride, tetrakis(triphenylphosphine) palladium (0), tris(dibenzylideneacetone) dipalladium (0) and the like can be illustrated. As the base to be used, potassium phosphate, potassium phosphate monohydrate, potassium carbonate, cesium carbonate, cesium fluoride, sodium carbonate and the like can be illustrated. The reaction temperature is usually from room temperature to a solvent reflux temperature, and the reaction time varies depending on a starting material and a solvent to be used, a reaction temperature or the like, but it is usually 30 minutes to 3 days. Further, the present step may be carried out with addition of a ligand such as 2-dicyclohexylphosphino-2',6'-dimethoxybiphenyl, bis(diphenylphosphino)ferrocene or the like, if necessary. Furthermore, the compound (8) used in the present step may be commercially available or can be prepared according to a method described in other literature or a similar method thereto.

Step 2-5

The compound (Id) of the present invention can be prepared by treating the compound (Ic) of the present invention according to a method of Step 1-2.

[B] Synthesis of Compound (1)

The compound (1) may be commercially available, or can be prepared by a method described in the following Scheme 3 or a similar method thereto, or a method described in other literature or a similar method thereto. Further, when a protective group is needed, combinations of introduction and cleavage can appropriately be carried out according to a usual method.

Scheme 3

[Chem.18]

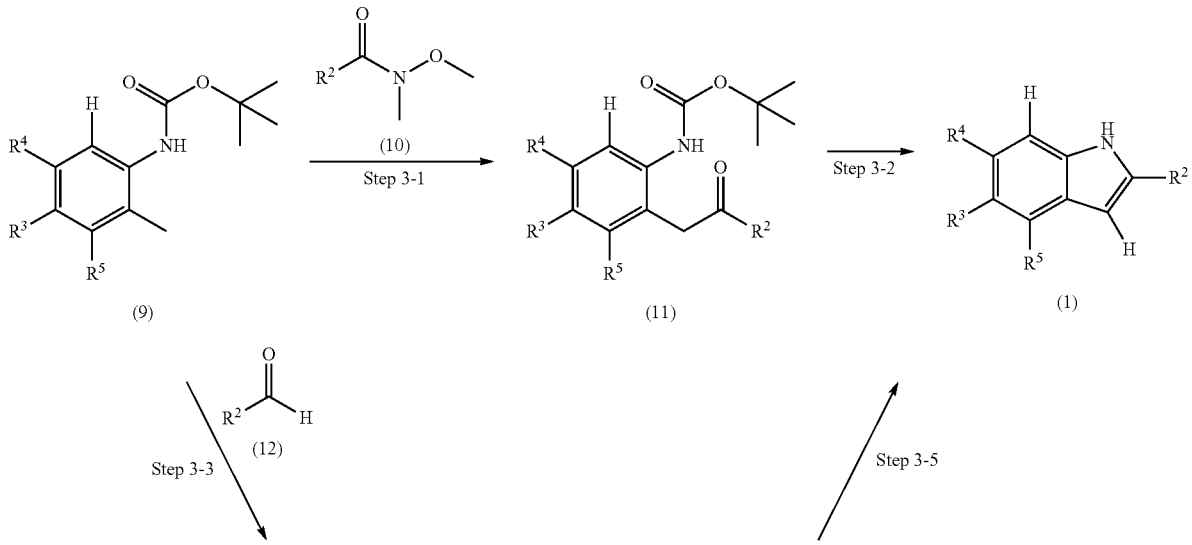

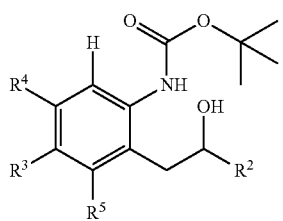

(13)

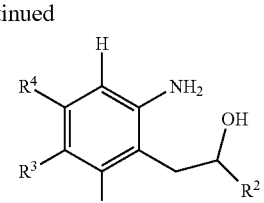

(14)

(wherein $R^2$, $R^3$, $R^4$ and $R^5$ have the same meanings as defined above)

Step 3-1

A compound (11) can be prepared by lithiating a compound (9) in a solvent using alkyllithium or the like and then reacting a compound (10) thereto. As the solvent to be used, tetrahydrofuran, diethyl ether, 1,2-dimethoxyethane, 1,4-dioxane, a mixed solvent thereof and the like can be illustrated. As the alkyllithium to be used, n-butyllithium, sec-butyllithium, tert-butyllithium and the like can be illustrated, and sec-butyllithium is preferable. The reaction temperature is usually from −78° C. to a solvent reflux temperature, and the reaction time varies depending on a starting material and a solvent to be used, a reaction temperature or the like, but it is usually 30 minutes to 1 day. Furthermore, the compounds (9) and (10) used in the present step may be commercially available or can be prepared according to a method described in other literature or a similar method thereto.

Step 3-2

The compound (1) can be prepared by treating the compound (11) with acid in a solvent. As the solvent to be used, dichloromethane, chloroform, methanol, ethanol, tetrahydrofuran, 1,4-dioxane, a mixed solvent thereof and the like can be illustrated. As the acid to be used, trifluoroacetic acid, methanesulfonic acid, concentrated hydrochloric acid, concentrated sulfuric acid and the like can be illustrated. The reaction temperature is usually from −78° C. to a solvent reflux temperature, and the reaction time varies depending on a starting material and a solvent to be used, a reaction temperature or the like, but it is usually 30 minutes to 3 days.

Step 3-3

A compound (13) can be prepared by lithiating the compound (9) in a solvent using alkyllithium or the like and then reacting a compound (12) thereto. As the solvent to be used, tetrahydrofuran, diethyl ether, 1,2-dimethoxyethane, 1,4-dioxane, a mixed solvent thereof and the like can be illustrated. As the alkyllithium to be used, n-butyllithium, sec-butyllithium, tert-butyllithium and the like can be illustrated, and sec-butyllithium is preferable. The reaction temperature is usually from −78° C. to a solvent reflux temperature, and the reaction time varies depending on a starting material and a solvent to be used, a reaction temperature or the like, but it is usually 30 minutes to 1 day. Furthermore, the compound (12) used in the present step may be commercially available or can be prepared according to a method described in other literature or a similar method thereto.

Step 3-4

A compound (14) can be prepared by treating the compound (13) under acidic condition. This reaction is well-known to a skilled person in the art and can be carried out using the method described in "Greene's Protective Groups in Organic Synthesis" edited by Greene & Wuts, fourth edition, Wiley-Interscience, 2006.

Step 3-5

The compound (1) can be prepared by oxidizing the compound (14) in a solvent in the presence of a palladium catalyst, a oxidizing agent and a base. As the solvent to be used, N,N-dimethylformamide, 1-methyl-2-pyrrolidone, a mixed solvent thereof and the like can be illustrated. As the palladium catalyst to be used, for example, tetrakis(triphenylphosphine)palladium (0) can be illustrated. As the oxidizing agent to be used, for example, mesityl bromide can be illustrated. As the base to be used, potassium carbonate, cesium carbonate, sodium hydride and the like can be illustrated. The reaction temperature is usually from room temperature to a solvent reflux temperature, and the reaction time varies depending on a starting material and a solvent to be used, a reaction temperature or the like, but it is usually 30 minutes to 3 days.

These schemes shown above are exemplification of the method for preparing the compound (I) of the present invention or an intermediate for preparation. These are allowed to be modified to such a scheme that can be readily understood by a person skilled in the art.

Also, in the case that there is a need of a protective group according to the kind of the functional group, combinations of introduction and cleavage can be appropriately carried out according to a usual method. The type, introduction, and cleavage of the protective group can be illustrated in reference to the method described in, for example, "Greene's Protective Groups in Organic Synthesis", edited by Theodra W. Greene & Peter G. M. Wuts, fourth edition, Wiley-Interscience, 2006.

The intermediates used for preparation of the compound (I) of the present invention or a pharmaceutically acceptable salt thereof can be isolated/purified, as necessary, by solvent extraction, crystallization/recrystallization, chromatography, preparative high performance liquid chromatography, or the like, that is an isolation/purification means well-known to a skilled person in the art.

Pharmaceutical Composition Comprising Compound (I) of the Present Invention or Pharmaceutically Acceptable Salt Thereof The pharmaceutical composition comprising the compound (I) of the present invention or a pharmaceutically acceptable salt thereof as an active ingredient is used in various dosage forms according to the usages. Examples of the dosage forms include powders, granules, fine granules, dry syrups, tablets, capsules, injections, liquids, ointments, suppositories, plasters, sublinguals, and the like, which are administered orally or parenterally.

These pharmaceutical compositions can be prepared by appropriately mixing or diluting/dissolving with pharmaceutical additives such as an excipient, a disintegrant, a binder, a lubricant, a diluent, a buffering agent, a tonicity agent, a preservative, a wetting agent, an emulsifier, a dispersant, a stabilizer, a solubilizing aid, and the like by a well-known method according to the dosage forms. In addition, when used in combination with agents other than the $EP_1$ receptor antagonist, the pharmaceutical compositions can be prepared by formulating the respective active ingredients simultaneously or separately as described above.

Pharmaceutical Use of Compound (I) of the Present Invention or Pharmaceutically Acceptable Salt Thereof The compound (I) of the present invention or a pharmaceutically acceptable salt thereof exhibits a potent $EP_1$ receptor antagonism in a test for confirmation of an $EP_1$ receptor antagonism. Therefore, the compound (I) of the present invention can suppress or decrease the intracellular calcium concentration. Accordingly, a pharmaceutical composition comprising the compound (I) of the present invention or a pharmaceutically acceptable salt thereof as an active ingredient can be used as an agent for treating or preventing diseases or symptoms caused by activation of the $EP_1$ receptor due to stimulus of a $PGE_2$.

In addition, examples of the diseases with the activation of the $EP_1$ receptor due to the $PGE_2$ stimulus include lower urinary tract symptoms (LUTS), inflammatory diseases, pain diseases, osteoporosis, cancer, and the like. The pharmaceutical composition comprising the compound (I) of the present invention or a pharmaceutically acceptable salt thereof as an active ingredient is preferably used as an agent for treating or preventing LUTS, inflammatory diseases, or pain diseases. It is more preferably LUTS.

Examples of the disease that causes the lower urinary tract symptoms include overactive bladder (OAB), benign prostatic hyperplasia (BPH), cystitis such as interstitial cystitis and the like, prostatitis, and the like.

The "lower urinary tract symptoms" means storage symptoms, voiding symptoms, post micturition symptoms, or the like. The compound (I) of the present invention or a pharmaceutically acceptable salt thereof is preferably used for treatment or prevention of storage symptoms.

Examples of the "storage symptoms" include urinary urgency, increased daytime frequency, nocturia, urinary incontinence (stress urinary incontinence, urge urinary incontinence, mixed urinary incontinence, enuresis, nocturnal enuresis, continuous urinary incontinence, and the like), and bladder sensation (increased bladder sensation, reduced bladder sensation, absent bladder sensation, non-specific bladder sensation, and the like). The compound (I) of the present invention or a pharmaceutically acceptable salt thereof is preferably used for treatment or prevention of urinary urgency, increased daytime frequency, nocturia, urge urinary incontinence, mixed urinary incontinence, enuresis, nocturnal enuresis, increased bladder sensation, or non-specific bladder sensation. It is more preferably urinary urgency, increased daytime frequency, nocturia, urge urinary incontinence, or increased bladder sensation. Further, the compound (I) of the present invention or a pharmaceutically acceptable salt thereof is particularly preferably used for treatment or prevention of OABs.

Combinations or Mixtures of Compound (I) of the Present Invention or Pharmaceutically Acceptable Salt Thereof The compound (I) of the present invention or a pharmaceutically acceptable salt thereof can be appropriately used in combination with at least one agent other than the $EP_1$ receptor antagonist.

Examples of the agent that can be used in combination with the compound (I) of the present invention or a pharmaceutically acceptable salt thereof include agents for the treatment of overactive bladder (OAB), benign prostatic hyperplasia (BPH), cystitis such as interstitial cystitis and the like, prostatitis, and the like, which have different action mechanisms from that of the $EP_1$ receptor antagonist. Examples of the agent include an anticholinergic agent, an $\alpha_1$ antagonist, a $\beta$ agonist, a 5α-reductase inhibitor, a PDE inhibitor, an acetylcholine esterase inhibitor, an anti-androgen, a progesterone-based hormone, an LH-RH analog, a neurokinin inhibitor, an anti-diuretic, a calcium channel blocker, a direct smooth muscle agonist, a tricyclic antidepressant, a K channel modulator, a sodium channel blocker, an $H_1$ blocker, a serotonin reuptake inhibitor, a norepinephrine reuptake inhibitor, a dopamine reuptake inhibitor, a GABA agonist, a TRPV1 modulator, an endothelin antagonist, a $5\text{-}HT_{1A}$ antagonist, an $\alpha_1$ agonist, an opioid agonist, a $P_2X$ antagonist, a COX inhibitor, a σ agonist, a muscarinic agonist, and the like. It is preferably an anticholinergic agent, an $\alpha_1$ antagonist, a $\beta$ agonist, a 5α-reductase inhibitor, a PDE inhibitor, a progesterone-based hormone, an anti-diuretic, a direct smooth muscle agonist, or a tricyclic antidepressant.

Furthermore, concrete examples of the agent that is used in combination are illustrated as below, but the context of the present invention is not limited thereto. Further, examples of the concrete compound include a free form thereof, and other pharmaceutically acceptable salts.

Examples of the "anticholinergic agent" include oxybutynin, propiverine, solifenacin, tolterodine, imidafenacin, temiberin, darifenacin, fesoterodine, trospium, propantheline, and the like.

Examples of the "$\alpha_1$ antagonist" include urapidil, naphthopidil, tamsulosin, silodosin, prazosin, terazosin, alfuzosin, doxazosin, CR-2991, fiduxosin, and the like.

Examples of the "β agonist" include YM-178, KUC-7483, KRP-204, SM-350300, TRK-380, amibegron, clenbuterol, SAR-150640, solabegron, and the like.

Examples of the "5α-reductase inhibitor" include dutasteride, TF-505, finasteride, izonsteride, and the like.

Examples of the "PDE inhibitor" include tadalafil, vardenafil, sildenafil, avanafil, UK-369003, T-0156, AKP-002, etazolate, and the like.

Examples of the "acetylcholine esterase inhibitor" include distigmine, donepezil, Z-338, rivastigmine, ganstigmine, BGC-20-1259, galantamine, itopride, NP-61, SPH-1286, tolserine, ZT-1, and the like.

Examples of the "anti-androgen" include gestonorone, oxendolone, bicalutamide, BMS-641988, CB-03-01, CH-4892789, flutamide, MDV-3100, nilutamide, TAK-700, YM-580, and the like.

Examples of the "progesterone-based hormone" include chlormadinone, allylestrenol, and the like.

Examples of the "LH-RH analog" include AEZS-108, buserelin, deslorelin, goserelin, histrelin, leuprorelin, lutropin, nafarelin, triptorelin, AEZS-019, cetrorelix, degarelix, elagolix, ganirelix, ozarelix, PTD-634, TAK-385, teverelix, TAK-448, TAK-683, and the like.

Examples of the "neurokinin inhibitor" include KRP-103, aprepitant, AV-608, casopitant, CP-122721, DNK-333, fosaprepitant, LY-686017, netupitant, orvepitant, rolapitant, TA-5538, T-2328, vestipitant, AZD-2624, Z-501, 1144814, MEN-15596, MEN-11420, SAR-102779, SAR-102279, saredutant, SSR-241586, and the like.

Examples of the "anti-diuretic" include desmopressin, VA-106483, and the like.

Examples of the "calcium channel blocker" include amlodipine, cilnidipine, propiverine, temiverine, PD-299685, aranidipine, azelnidipine, barnidipine, benidipine, bevantolol, clevidipine, CYC-381, diltiazem, efonidipine, fasudil, felodipine, gabapentin, gallopamil, isradipine, lacidipine, lercanidipine, lomerizine, manidipine, MEM-1003, nicardipine, nifedipine, nilvadipine, nimodipine, nisoldipine, SB-751689, verapamil, YM-58483, ziconotide, and the like.

Examples of the "direct smooth muscle agonist" include flavoxate and the like.

Examples of the "tricyclic antidepressant" include imipramine, clomipramine, amitriptyline, and the like.

Examples of the "K channel modulator" include nicorandil, NIP-141, NS-4591, NS-1643, andolrast, diazoxide, ICA-105665, minoxidil, pinacidil, tilisolol, VRX-698, and the like.

Examples of the "sodium channel blocker" include bepridil, dronedarone, propafenone, safinamide, SUN-N8075, SMP-986, 1014802, 552-02, A-803467, brivaracetam, cibenzoline, eslicarbazepine, F-15845, flecamide, fosphenyloin, lacosamide, lamotrigine, levobupivacaine, M-58373, mexiletine, moracizine, nerispirdine, NW-3509, oxcarbazepine, pilsicamide, pirmenol, propafenone, NW-1029, ropivacaine, vernakalant, and the like.

Examples of the "H1 blocker" include acrivastine, alcaftadine, bepotastine, bilastine, cetirizine, desloratadine, ebastine, efletirizine, epinastine, fexofenadine, GSK-835726, levocabastine, levocetirizine, loratadine, mequitazine, mizolastine, NBI-75043, ReN-1869, terfenadine, UCB-35440, vapitazine, YM-344484, diphenhydramine, chlorpheniramine, and the like.

Examples of the "serotonin reuptake inhibitor" include UCB-46331, 424887, AD-337, BGC-20-1259, BMS-505130, citalopram, dapoxetine, desvenlafaxine, DOV-102677, DOV-216303, DOV-21947, duloxetine, escitalopram, F-2695, F-98214-TA, fluoxetine, fluvoxamine, IDN-5491, milnacipran, minaprine, NS-2359, NSD-644, paroxetine, PF-184298, SD-726, SEP-225289, SEP-227162, SEP-228425, SEP-228432, sertraline, sibutramine, tesofensine, tramadol, trazodone, UCB-46331, venlafaxine, vilazodone, WAY-426, WF-516, and the like.

Examples of the "norepinephrine reuptake inhibitor" include AD-337, desvenlafaxine, DOV-102677, DOV-216303, DOV-21947, duloxetine, F-2695, F-98214-TA, milnacipran, NS-2359, NSD-644, PF-184298, SD-726, SEP-225289, SEP-227162, SEP-228425, SEP-228432, sibutramine, tesofensine, tramadol, venlafaxine, bupropion, radafaxine, atomoxetine, DDP-225, LY-2216684, neboglamine, NRI-193, reboxetine, tapentadol, WAY-256805, WAY-260022, and the like.

Examples of the "dopamine reuptake inhibitor" include DOV-102677, DOV-216303, DOV-21947, IDN-5491, NS-2359, NSD-644, SEP-225289, SEP-228425, SEP-228432, sibutramine, tesofensine, tramadol, brasofensine, bupropion, NS-27100, radafaxine, safinamide, and the like.

Examples of the "GABA agonist" include retigabine, eszopiclone, indiplon, pagoclone, SEP-225441, acamprosate, baclofen, AZD-7325, BL-1020, brotizolam, DP-VPA, progabide, propofol, topiramate, zopiclone, EVT-201, AZD-3043, ganaxolone, NS-11394, arbaclofen, AZD-3355, GS-39783, ADX-71441, ADX-71943, and the like.

Examples of the "TRPV1 modulator" include capsaicin, resiniferatoxin, DE-096, GRC-6211, AMG-8562, JTS-653, SB-705498, A-425619, A-784168, ABT-102, AMG-628, AZD-1386, JNJ-17203212, NGD-8243, PF-3864086, SAR-115740, SB-782443, and the like.

Examples of the "endothelin antagonist" include SB-234551, ACT-064992, ambrisentan, atrasentan, bosentan, clazosentan, darusentan, fandosentan, S-0139, TA-0201, TBC-3711, zibotentan, BMS-509701, PS-433540, and the like.

Examples of the "5-HT$_{1A}$ antagonist" include espindolol, lecozotan, lurasidone, E-2110, REC-0206, SB-649915, WAY-426, WF-516, and the like.

Examples of the "$\alpha_1$ agonist" include CM-2236, armodafinil, midodrine, moclafinil, and the like.

Examples of the "opioid agonist" include morphine, TRK-130, DPI-125, DPI-3290, fentanyl, LIF-301, loperamide, loperamide oxide, remifentanil, tapentadol, WY-16225, oxycodone, PTI-202, PTI-721, ADL-5747, ADL-5859, DPI-221, DPI-353, IPP-102199, SN-11, ADL-10-0101, ADL-10-0116, asimadoline, buprenorphine, CR-665, CR-845, eptazocine, nalbuphine, nalfurafine, pentazocine, XEN-0548, W-212393, ZP-120, nalmefene, and the like.

Examples of the "P$_2$X antagonist" include A-740003, AZ-11657312, AZD-9056, GSK-1482160, GSK-31481A, and the like.

Examples of the "COX inhibitor" include aceclofenac, ST-679, aspirin, bromfenac, dexketoprofen, flurbiprofen, FYO-750, ibuprofen, ketoprofen, ketorolac, licofelone, lornoxicam, loxoprofen, LT-NS001, diclofenac, mofezolac, nabumetone, naproxen, oxaprozin, piroxicam, pranoprofen, suprofen, tenoxicam, tiaprofenic acid, tolfenamic acid, zaltoprofen, 644784, ABT-963, ajulemic acid, apricoxib, celecoxib, cimicoxib, etoricoxib, iguratimod, lumiracoxib, meloxicam, nimesulide, parecoxib, RO-26-2198, valdecoxib, and the like.

Examples of the "σ agonist" include ANAVEX-27-1041, PRS-013, SA-4503, ANAVEX-2-73, siramesine, ANAVEX-7-1037, ANAVEX-1-41, and the like.

Examples of the "muscarinic agonist" include AC-260584, cevimeline, MCD-386, NGX-267, NGX-292, sabcomeline, pilocarpine, bethanechol, and the like.

When the compound (I) of the present invention or a pharmaceutically acceptable salt thereof is used in combination with one or more of the above-described agents, the present invention includes at least one administration method selected from 1) to 5) below:

1) simultaneous administration by a combination preparation, 2) simultaneous administration by the same administration pathway as a separate formulation, 3) simultaneous administration by a different administration pathway as a separate formulation, 4) administration at different times by the same administration pathway as a separate formulation, or 5) administration at different times by a different administration pathway as a separate formulation.

Further, in the case of administration at different times as a separate formulation as in 4) or 5), the order of administration of the compound (I) of the present invention and the above-described agents is not particularly limited.

Furthermore, the compound (I) of the present invention or a pharmaceutically acceptable salt thereof can be used appropriately in combination of one or more of the above-described agents to attain an advantageous effect that is equal to or more than an additive effect in prevention or treatment of the above-described diseases. Alternatively, as compared with a case of being used alone, the amount used can be reduced, the side effects of the agent used together can be reduced, or the side effects of the agent used together can be avoided or mitigated.

Usage/Dose of Compound (I) of the Present Invention

The pharmaceutical of the present invention can be administered systematically or locally, orally or parenterally (nasal, pulmonary, intravenous, rectal, subcutaneous, intramuscular, transdermal routes, and the like).

When the pharmaceutical composition of the present invention is used for practical treatments, the dose of the compound (I) of the present invention or a pharmaceutically acceptable salt thereof that is the active ingredient is appropriately determined by taking the patient's age, gender, weight, medical condition, degree of the treatment, and the like into consideration. For example, in case of oral administration, administration can be conducted appropriately at a daily dose in the range from about 0.01 to 1000 mg for an adult (as a body weight of 60 kg), and in case of parenteral administration, administration can be conducted appropriately at a daily dose in the range from about 0.001 to 300 mg for an adult in one portion or in several divided portions. In addition, the dose of the compound (I) of the present invention or a pharmaceutically acceptable salt thereof can be reduced according to the amount of the agent other than an $EP_1$ receptor antagonist.

Hereinbelow, the present invention is illustrated in detail with reference to Examples, Reference Examples, and Test Examples, but the scope of the present invention is not limited thereto.

EXAMPLES

In the symbols used in each of Reference Examples, Examples, and Tables, Ref. No. means Reference Example No., Ex. No. means Example No., Strc means a chemical structural formula, Physical data means physical property values, $^1$H-NMR means a proton nuclear magnetic resonance spectrum, $CDCl_3$ means chloroform-d, and $DMSO-d_6$ means dimethylsulfoxide-$d_6$. Further, MS means mass spectroscopy, and ESI means measurement by an electrospray ionization method.

Reference Example 1

2-Phenylethynyl-4-trifluoromethoxyaniline

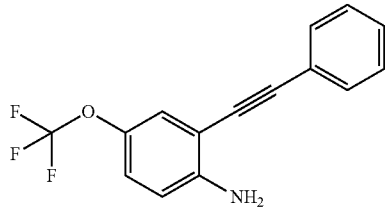

[Chem. 19]

To a mixture of 2-bromo-4-trifluoromethoxyaniline (0.500 g), cupper iodide (I) (18.6 mg), bis(triphenylphosphine)palladium (II) dichloride (68.5 mg), triethylamine (0.817 mL) and tetrahydrofuran (7.8 mL) was added phenylacetylene (0.279 mL) at room temperature under stirring, and the mixture was stirred at 80° C. for 16 hours. The reaction mixture was cooled to room temperature, diluted with diethyl ether (30 mL) and then filtered through celite (registered trademark). The filtrate was concentrated under reduced pressure. The residue was purified by silica gel column chromatography (eluting solvent: ethyl acetate-hexane) to obtain the title compound (206 mg).

$^1$H-NMR ($CDCl_3$) δ ppm:
4.32 (2H, br s), 6.70 (1H, d, J=8.8 Hz), 6.95-7.10 (1H, m), 7.20-7.30 (1H, m), 7.30-7.45 (3H, m), 7.45-7.60 (2H, m).

Reference Example 2

2-Phenyl-5-trifluoromethoxyindole

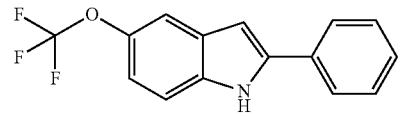

[Chem. 20]

To a solution of potassium tert-butoxide (173 mg) in 1-methyl-2-pyrrolidone (3.7 mL) was added dropwise a solution of 2-phenylethynyl-4-trifluoromethoxyaniline (204 mg) in 1-methyl-2-pyrrolidone (3.7 mL) at room temperature under stirring, and the mixture was stirred for 6 hours. The reaction mixture was diluted with water and extracted with ethyl acetate. The organic layer was washed with water, dried over anhydrous sodium sulfate and concentrated under reduced pressure. The residue was purified by silica gel column chromatography (eluting solvent: ethyl acetate-hexane) to obtain the title compound (171 mg).

$^1$H-NMR ($CDCl_3$) δ ppm:
6.80-6.90 (1H, m), 7.00-7.15 (1H, m), 7.30-7.55 (5H, m), 7.60-7.75 (2H, m), 8.42 (1H, br s).

Reference Example 3

5-Chloro-2-(1-methylpropyl)indole

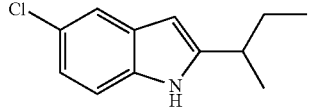

[Chem. 21]

To a solution of tert-butyl (4-chloro-2-methylphenyl)carbamate (338 mg) in tetrahydrofuran (6 mL) was added dropwise sec-butyllithium (1.04 mol/L hexane-cyclohexane solution, 2.69 mL) at −70° C. under an argon atmosphere. The mixture was warmed to −40° C. and then stirred for 10 minutes. Then a solution of N-methoxy-N,2-dimethylbutanamide (203 mg) in tetrahydrofuran (0.5 mL) was added dropwise, and the mixture was stirred at −40° C. for 40 minutes. The mixture was stirred at room temperature for additional 2 hours. 1 mol/L Hydrochloric acid (2.8 mL) was added to the reaction mixture under cooling with ice, and this resulting mixture was extracted with diethyl ether. The organic layer was washed with saturated saline, dried over anhydrous sodium sulfate and concentrated under reduced pressure. The residue (446 mg) was dissolved in dichloromethane (4 mL). Trifluoroacetic acid (0.8 mL) was added and this resulting mixture was stirred at room temperature for 14 hours. The reaction mixture was diluted with dichloromethane, washed successively with water and a saturated aqueous sodium hydrogen carbonate solution, dried over anhydrous sodium sulfate and concentrated under reduced pressure. The residue was purified by silica gel column chromatography (eluting solvent: ethyl acetate-hexane) to obtain the title compound (173 mg).

$^1$H-NMR ($CDCl_3$) δ ppm:
0.91 (3H, t, J=7.4 Hz), 1.33 (3H, d, J=7.0 Hz), 1.55-1.80 (2H, m), 2.75-2.90 (1H, m), 6.15-6.25 (1H, m), 7.06 (1H, dd, J=2.0, 8.5 Hz), 7.21 (1H, d, J=8.5 Hz), 7.45-7.55 (1H, m), 7.90 (1H, br s).

Reference Example 4

5-Fluoro-4-methoxy-2-methylaniline

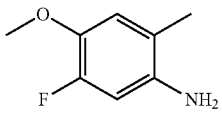
[Chem. 22]

To a solution of 2-fluoro-5-methyl-4-nitroanisole (100 mg) in tetrahydrofuran-ethanol (1/1, 3 mL) was added 10% palladium on carbon powder (56.5 wt % aqueous, 30 mg) under cooling with ice, and the mixture was stirred at room temperature for 5 hours under a hydrogen atmosphere. The reaction mixture was filtered through celite (registered trademark). The filtrate was concentrated under reduced pressure to obtain the title compound (84.8 mg).

$^1$H-NMR (CDCl$_3$) δ ppm:
2.12 (3H, s), 3.42 (2H, br s), 3.81 (3H, s), 6.46 (1H, d, J=12.5 Hz), 6.70 (1H, d, J=9.3 Hz).

Reference Example 5 tert-Butyl (5-fluoro-4-methoxy-2-methylphenyl)carbamate

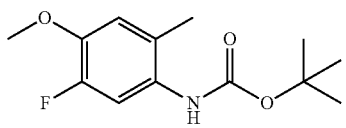
[Chem. 23]

To a solution of 5-fluoro-4-methoxy-2-methylaniline (900 mg) in tetrahydrofuran (12 mL) was added di-tert-butyl dicarbonate (1.27 g) at room temperature, and the mixture was stirred overnight at 60° C. The reaction mixture was concentrated under reduced pressure. The residue was purified by aminopropylated silica gel column chromatography (eluting solvent: ethyl acetate-hexane). The fractions of the target were combined and the solvents were evaporated under reduced pressure. Hexane was added to the residue. The precipitate was collected by filtration, washed with hexane and dried under reduced pressure to obtain the title compound (1.24 g).

$^1$H-NMR (CDCl$_3$) δ ppm:
1.51 (9H, s), 2.20 (3H, s), 3.85 (3H, s), 6.09 (1H, br s), 6.74 (1H, d, J=9.0 Hz), 7.30-7.80 (1H, m).

Reference Example 6-1 tert-Butyl[4-chloro-2-(4-methyl-2-oxopentyl)phenyl]carbamate

To a solution of tert-butyl (4-chloro-2-methyphenyl)carbamate (483 mg) in tetrahydrofuran (7 mL) was added dropwise sec-butyllithium (1.04 mol/L hexane-cyclohexane solution, 4.3 mL) at −40° C. under an argon atmosphere, and the mixture was stirred for 15 minutes. Then a solution of N-methoxy-N,3-methylbutylamide (319 mg) in tetrahydrofuran (1 mL) was added dropwise, and the mixture was stirred at −40° C. for 15 minutes and at room temperature for 2 hours. Water and 1 mol/L hydrochloric acid were added to the reaction mixture and this resulting mixture was extracted with ethyl acetate. The aqueous layer was extracted once again with ethyl acetate. The combined organic layers were washed with saturated saline, dried over anhydrous magnesium sulfate and concentrated under reduced pressure. The residue was purified by silica gel column chromatography (eluting solvent: ethyl acetate-hexane) to obtain the title compound (282 mg).

In addition, structural formula and spectral data of the title compound were shown in Table 1.

Reference Examples 6-2 to 6-8

The compounds shown in Tables 1 to 2 were synthesized in a manner similar to that of Reference Example 6-1 by using the corresponding starting material and reactants.

TABLE 1

| Ref. No. | Strc | Physical data |
| --- | --- | --- |
| 6-1 | | $^1$H-NMR (CDCl$_3$) δ ppm:<br>0.91 (6H, d, J = 6.5 Hz), 1.51 (9H, s),<br>2.05-2.25 (1H, m), 2.45 (2H, d,<br>J = 6.8 Hz), 3.64 (2H, s), 7.12 (1H, d,<br>J = 2.5 Hz), 7.23 (1H, dd, J = 2.5, 8.8 Hz),<br>7.35-7.90 (2H, m). |
| 6-2 | | $^1$H-NMR (CDCl$_3$) δ ppm:<br>0.86 (3H, t, J = 7.5 Hz), 1.11 (3H, d,<br>J = 6.8 Hz), 1.35-1.55 (10H, m),<br>1.65-1.80 (1H, m), 2.55-2.70 (1H, m),<br>3.71 (2H, s), 3.77 (3H, s), 6.67 (1H, d,<br>J = 3.0 Hz), 6.80 (1H, dd, J = 3.0, 8.8 Hz),<br>7.11 (1H, br s), 7.40-7.65 (1H, m). |

TABLE 1-continued

| Ref. No. | Strc | Physical data |
| --- | --- | --- |
| 6-3 | | ¹H-NMR (CDCl₃) δ ppm:<br>0.83 (6H, t, J = 7.5 Hz), 1.40-1.80 (13H, m), 2.45-2.60 (1H, m), 3.70 (2H, s), 3.77 (3H, s), 6.66 (1H, d, J = 2.9 Hz), 6.81 (1H, dd, J = 2.9, 8.8 Hz), 7.11 (1H, br s), 7.40-7.65 (1H, m). |
| 6-4 | | ¹H-NMR (CDCl₃) δ ppm:<br>1.49 (9H, s), 3.76 (3H, s), 4.15 (2H, s), 6.74 (1H, d, J = 2.9 Hz), 6.81 (1H, dd, J = 2.9, 8.8 Hz), 7.20-7.70 (4H, m), 8.15-8.25 (1H, m). |
| 6-5 | | ¹H-NMR (CDCl₃) δ ppm:<br>0.82 (6H, t, J = 7.4 Hz), 1.40-1.75 (13H, m), 2.45-2.60 (1H, m), 3.68 (2H, s), 7.10 (1H, d, J = 2.5 Hz), 7.23 (1H, dd, J = 2.5, 8.8 Hz), 7.40-7.85 (2H, m). |

TABLE 2

| Ref. No. | Strc | Physical data |
| --- | --- | --- |
| 6-6 | | ¹H-NMR (CDCl₃) δ ppm:<br>1.50 (9H, s), 3.76 (3H, s), 4.00 (2H, s), 6.71 (1H, d, J = 2.8 Hz), 6.75-6.85 (2H, m), 7.15-7.70 (3H, m), 8.16 (1H, s). |
| 6-7 | | ¹H-NMR (CDCl₃) δ ppm:<br>0.85-1.00 (2H, m), 1.05-1.15 (2H, m), 1.50 (9H, s), 1.95-2.10 (1H, m), 3.78 (3H, s), 3.80 (2H, s), 6.74 (1H, d, J = 2.9 Hz), 6.81 (1H, dd, J = 2.9, 8.8 Hz), 7.00 (1H, br s), 7.40-7.70 (1H, m). |

TABLE 2-continued

| Ref. No. | Strc | Physical data |
|---|---|---|
| 6-8 | | ¹H-NMR (CDCl₃) δ ppm:<br>1.49 (9H, s), 3.83 (3H, s), 4.24 (2H, s), 6.76 (1H, d, J = 9.0 Hz), 7.40-7.70 (5H, m), 8.00-8.15 (2H, m). |

Reference Example 7-1

5-Chloro-2-isobutylindole

To a solution of tert-butyl[4-chloro-2-(4-methyl-2-oxopentyl)phenyl]carbamate (280 mg) in dichloromethane (4 mL) was added trifluoroacetic acid (0.7 mL) at room temperature, and the mixture was stirred for 7 hours. The reaction mixture was diluted with ethyl acetate and stopped the reaction by addition of a saturated aqueous sodium hydrogen carbonate solution. The organic layer was washed with saturated saline, dried over anhydrous magnesium sulfate and concentrated under reduced pressure. The residue was purified by silica gel column chromatography (eluting solvent: ethyl acetate-hexane) to obtain the title compound (166 mg).

In addition, structural formula and spectral data of the title compound were shown in Table 3.

Reference Examples 7-2 to 7-8

The compounds shown in Tables 3 to 4 were synthesized in a manner similar to that of Reference Example 7-1 by using the corresponding starting material and reactant.

TABLE 3

| Ref. No. | Strc | Physical data |
|---|---|---|
| 7-1 | | ¹H-NMR (CDCl₃) δ ppm:<br>0.97 (6H, d, J = 6.8 Hz), 1.90-2.05 (1H, m), 2.61 (2H, d, J = 7.3 Hz), 6.15-6.25 (1H, m), 7.06 (1H, dd, J = 2.0, 8.5 Hz), 7.20 (1H, d, J = 8.5 Hz), 7.45-7.55 (1H, m), 7.87 (1H, br s). |
| 7-2 | | ¹H-NMR (CDCl₃) δ ppm:<br>0.91 (3H, t, J = 7.4 Hz), 1.32 (3H, d, J = 7.0 Hz), 1.55-1.80 (2H, m), 2.75-2.90 (1H, m), 3.84 (3H, s), 6.15-6.20 (1H, m), 6.77 (1H, dd, J = 2.4, 8.8 Hz), 7.02 (1H, d, J = 2.4 Hz), 7.19 (1H, d, J = 8.8 Hz), 7.77 (1H, br s). |
| 7-3 | | ¹H-NMR (CDCl₃) δ ppm:<br>0.86 (6H, t, J = 7.4 Hz), 1.50-1.85 (4H, m), 2.45-2.65 (1H, m), 3.84 (3H, s), 6.15-6.25 (1H, m), 6.77 (1H, dd, J = 2.3, 8.7 Hz), 7.02 (1H, d, J = 2.3 Hz), 7.20 (1H, d, J = 8.7 Hz), 7.74 (1H, br s). |
| 7-4 | | ¹H-NMR (CDCl₃) δ ppm:<br>3.86 (3H, s), 6.60-6.70 (1H, m), 6.85 (1H, dd, J = 2.4, 8.8 Hz), 7.07 (1H, d, J = 2.4 Hz), 7.00-7.10 (1H, m), 7.20-7.35 (1H, m), 7.35-7.45 (3H, m), 8.11 (1H, br s). |
| 7-5 | | ¹H-NMR (CDCl₃) δ ppm:<br>0.86 (6H, t, J =7.4 Hz), 1.50-1.85 (4H, m), 2.45-2.65 (1H, m), 6.15-6.25 (1H, m), 7.06 (1H, dd, J = 2.0, 8.6 Hz), 7.21 (1H, d, J = 8.6 Hz), 7.49 (1H, d, J = 2.0 Hz), 7.86 (1H, br s). |

TABLE 4

| Ref. No. | Strc | Physical data |
|---|---|---|
| 7-6 | | $^1$H-NMR (CDCl$_3$) δ ppm: 3.86 (3H, s), 6.50-6.60 (1H, m), 6.65-6.75 (1H, m), 6.83 (1H, dd, J = 2.4, 8.7 Hz), 7.05 (1H, d, J = 2.4 Hz), 7.20-7.30 (1H, m), 7.45-7.55 (1H, m), 7.70-7.80 (1H, m), 7.98 (1H, br s). |
| 7-7 | | $^1$H-NMR (CDCl$_3$) δ ppm: 0.70-0.80 (2H, m), 0.90-1.00 (2H, m), 1.90-2.00 (1H, m), 3.83 (3H, s), 6.05-6.15 (1H, m), 6.76 (1H, dd, J = 2.4, 8.7 Hz), 6.98 (1H, d, J = 2.4 Hz), 7.16 (1H, d, J = 8.7 Hz), 7.81 (1H, br s). |
| 7-8 | | $^1$H-NMR (CDCl$_3$) δ ppm: 3.94 (3H, s), 6.70-6.80 (1H, m), 7.10-7.20 (2H, m), 7.25-7.50 (3H, m), 7.55-7.70 (2H, m), 8.23 (1H, br s). |

Reference Example 8

5-Ethoxy-2-nitrobenzaldehyde

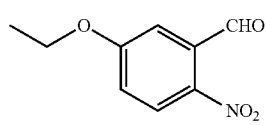
[Chem. 24]

To a suspension of 5-hydroxy-2-nitrobenzaldehyde (500 mg) and cesium carbonate (1.46 g) in N,N-dimethylformamide (10 mL) was added ethyl iodide (0.265 mL) at room temperature, and the mixture was stirred for 2 days. Water was added to the reaction mixture and this resulting mixture was extracted with ethyl acetate. The aqueous layer was extracted with ethyl acetate. The combined organic layers were washed with water and saturated saline, dried over anhydrous magnesium sulfate and concentrated under reduced pressure. The residue was purified by silica gel column chromatography (eluting solvent: ethyl acetate-hexane) to obtain the title compound (519 mg).

$^1$H-NMR (CDCl$_3$) δ ppm:
1.48 (3H, t, J=7.0 Hz), 4.18 (2H, q, J=7.0 Hz), 7.13 (1H, dd, J=2.9, 9.1 Hz), 7.31 (1H, d, J=2.9 Hz), 8.16 (1H, d, J=9.1 Hz), 10.49 (1H, s).

Reference Example 9

2-(2,2-Dibromovinyl)-4-ethoxynitrobenzene

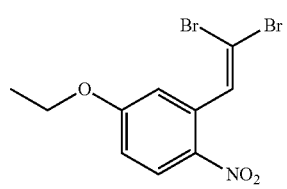
[Chem. 25]

To a solution of 5-ethoxy-2-nitrobenzaldehyde (519 mg) and triphenylphosphine (2.09 g) in dichloromethane (13 mL) was added a solution of carbon tetrabromide (1.32 g) in dichloromethane in three minutes under cooling with ice, and the mixture was stirred overnight at room temperature. Hexane (20 mL) was added to the reaction mixture, and this resulting mixture was stirred for 10 minutes and then filtered through silica gel. The filtrate was concentrated under reduced pressure. The residue was purified by silica gel column chromatography (eluting solvent: ethyl acetate-hexane) to obtain the title compound (712 mg).

$^1$H-NMR (CDCl$_3$) δ ppm:
1.47 (3H, t, J=6.9 Hz), 4.15 (2H, q, J=6.9 Hz), 6.90-7.05 (2H, m), 7.80 (1H, s), 8.17 (1H, d, J=9.1 Hz).

Reference Example 10

2-(2,2-Dibromovinyl)-4-ethoxyaniline

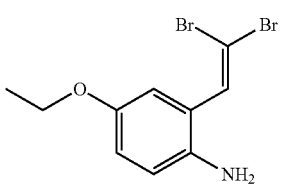
[Chem. 26]

To a suspension of 2-(2,2-dibromovinyl)-4-ethoxynitrobenzene (200 mg) in methanol (3 mL) was added 1% platinum on activated carbon (vanadium doped, 50% hydrous, 27.5 mg) at room temperature, and the mixture was stirred for six and a half hours under a hydrogen atmosphere. 1% Platinum on activated carbon (vanadium doped, 50% hydrous, 27.5 mg) was added, and the mixture was stirred for additional one hour under a hydrogen atmosphere. The reaction mixture was filtered through celite (registered trademark) and the filtrate was concentrated under reduced pressure. The residue was purified by silica gel column chromatography (eluting solvent: ethyl acetate-hexane) to obtain the title compound (155 mg).

$^1$H-NMR (CDCl$_3$) δ ppm:
1.38 (3H, t, J=7.0 Hz), 3.44 (2H, br s), 3.97 (2H, q, J=7.0 Hz), 6.55-7.00 (3H, m), 7.34 (1H, s).

Reference Example 11

Methyl 3-{[2-(2,2-dibromovinyl)-4-ethoxyphenylamino]methyl}benzoate

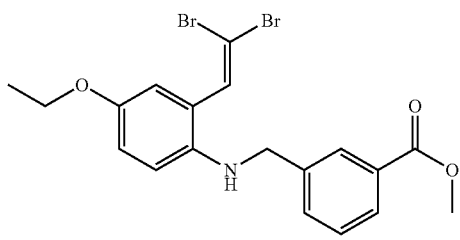

[Chem. 27]

A suspension of 2-(2,2-dibromovinyl)-4-ethoxyaniline (240 mg), methyl 3-(bromomethyl)benzoate (180 mg) and potassium carbonate (124 mg) in N,N-dimethylformamide (2 mL) was stirred overnight at room temperature. Water was added to the reaction mixture and this resulting mixture was extracted with ethyl acetate. The organic layer was washed with saturated saline, dried over anhydrous magnesium sulfate and concentrated under reduced pressure. The residue was purified by silica gel column chromatography (eluting solvent: ethyl acetate-hexane) to obtain the title compound (258 mg).

$^1$H-NMR (CDCl$_3$) δ ppm:
1.37 (3H, t, J=6.9 Hz), 3.70-3.85 (1H, m), 3.85-4.05 (5H, m), 4.38 (2H, d, J=5.5 Hz), 6.52 (1H, d, J=8.8 Hz), 6.70-6.85 (1H, m), 6.90-7.00 (1H, m), 7.34 (1H, s), 7.35-7.50 (1H, m), 7.50-7.65 (1H, m), 7.90-8.15 (2H, m).

Reference Example 12

1-(3-Benzyloxybenzyl)-5-methoxy-2-phenylindole

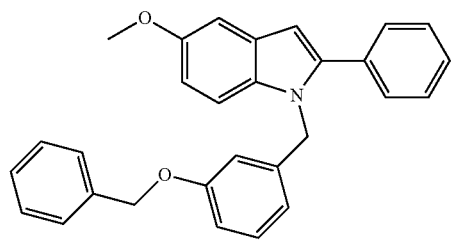

[Chem. 28]

To a solution of 5-methoxy-2-phenylindole (245 mg) in N,N-dimethylformamide (4.5 mL) was added sodium hydride (dispersed in liquid paraffin, minimum 55%, 72 mg) under cooling with ice, and the mixture was stirred at room temperature for 75 minutes. Then a solution of 3-(benzyloxy)benzyl bromide (365 mg) in N,N-dimethylformamide (1 mL) was added dropwise, and the mixture was stirred at 80° C. for 15 hours. The reaction mixture was cooled to room temperature. A saturated aqueous ammonium chloride solution-water (2/1) were added and this resulting mixture was extracted with ethyl acetate. The organic layer was washed with saturated saline, dried over anhydrous sodium sulfate and concentrated under reduced pressure. The residue was purified by aminopropylated silica gel column chromatography to obtain the title compound (202 mg).

$^1$H-NMR (CDCl$_3$) δ ppm:
3.87 (3H, s), 4.94 (2H, s), 5.29 (2H, s), 6.55-6.60 (1H, m), 6.60-6.70 (2H, m), 6.75-6.90 (2H, m), 7.06 (1H, d, J=8.8 Hz), 7.13 (1H, d, J=2.3 Hz), 7.19 (1H, t, J=8.0 Hz), 7.25-7.50 (10H, m).

Reference Example 13

1-(3-Hydroxybenzyl)-5-methoxy-2-phenylindole

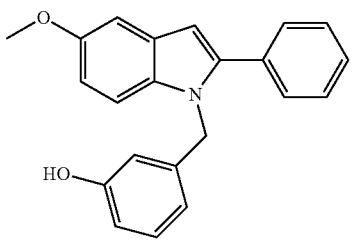

[Chem. 29]

1-(3-Benzyloxybenzyl)-5-methoxy-2-phenylindole (200 mg) was dissolved in trifluoroacetic acid-water-dimethyl sulfide (95/5/10, 4.8 mL), and the solution was stirred at room temperature for 68 hours. The reaction mixture was concentrated under reduced pressure. The residue was dissolved in ethyl acetate. The solution was washed successively with a saturated aqueous sodium hydrogen carbonate solution and saturated saline, dried over anhydrous sodium sulfate and concentrated under reduced pressure. The residue was purified by silica gel column chromatography (eluting solvent: ethyl acetate-hexane) to obtain the title compound (110 mg).

$^1$H-NMR (CDCl$_3$) δ ppm:
3.87 (3H, s), 4.71 (1H, s), 5.28 (2H, s), 6.40-6.50 (1H, m), 6.55-6.60 (1H, m), 6.60-6.75 (2H, m), 6.81 (1H, dd, J=2.5, 8.9 Hz), 7.07 (1H, d, J=8.9 Hz), 7.10-7.20 (2H, m), 7.30-7.50 (5H, m).

Reference Example 14 tert-Butyl[4-methoxy-2-(2-hydroxy-3,3-dimethylbutyl)phenyl]carbamate

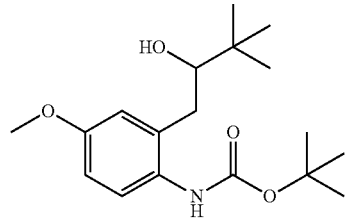 [SMILES: CCC(C)C(=O)Cc1cc(OC)ccc1NC(=O)OC(C)(C)C]

[Chem. 30]

To a solution of tert-butyl (4-methoxy-2-methylphenyl)carbamate (475 mg) in tetrahydrofuran (7 mL) was added dropwise sec-butyllithium (1.04 mol/L hexane-cyclohexane solution, 4.3 mL) at −40° C. under an argon atmosphere, and the mixture was stirred for 15 minutes. Then a solution of trimethylacetaldehyde (0.287 mL) in tetrahydrofuran (1 mL) was added dropwise, and the mixture was stirred at −40° C. for 15 minutes and at room temperature for additional one hour. Water and μmol/L hydrochloric acid were added to the reaction mixture and this resulting mixture was extracted with ethyl acetate. The organic layer was washed with water and saturated saline, dried over anhydrous magnesium sulfate and concentrated under reduced pressure. The residue was purified by silica gel column chromatography (eluting solvent: ethyl acetate-hexane) to obtain the title compound (234 mg).
<sup>1</sup>H-NMR (CDCl<sub>3</sub>) δ ppm:
1.00 (9H, s), 1.50 (9H, s), 1.90-2.20 (1H, br), 2.55-2.75 (2H, m), 3.35-3.50 (1H, m), 3.78 (3H, s), 6.65-6.80 (2H, m), 7.20-7.60 (2H, m).

Reference Example 15

1-(2-Amino-5-methoxyphenyl)-3,3-dimethylbutan-2-ol

[Chem. 31]

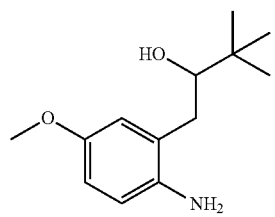

To a solution of tert-butyl[4-methoxy-2-(2-hydroxy-3,3-dimethylbutyl)phenyl]carbamate (234 mg) in dichloromethane (2 mL) was added trifluoroacetic acid (1 mL) at room temperature, and the mixture was stirred for one hour. The reaction mixture was poured into 5% aqueous sodium hydrogen carbonate solution (40 mL) and extracted with ethyl acetate. The organic layer was washed with saturated saline, dried over anhydrous magnesium sulfate and concentrated under reduced pressure to obtain the title compound (157 mg).
$^1$H-NMR (CDCl$_3$) δ ppm:
1.01 (9H, s), 2.40-3.70 (5H, m), 3.75 (3H, s), 6.60-6.70 (3H, m).

Reference Example 16

Methyl 3-{[2-(2-hydroxy-3,3-dimethylbutyl)-4-methoxyphenylamino]methyl}benzoate

[Chem. 32]

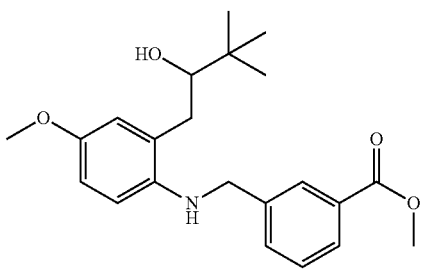

To a solution of 1-(2-amino-5-methoxyphenyl)-3,3-dimethylbutan-2-ol (155 mg) and methyl 3-formylbenzoate (137 mg) in acetic acid (2 mL) was added sodium triacetoxyborohydride (294 mg) at room temperature, and the mixture was stirred for one hour. The reaction mixture was diluted with ethyl acetate and washed with 5% aqueous sodium hydrogen carbonate solution. The organic layer was washed with saturated saline, dried over anhydrous magnesium sulfate and concentrated under reduced pressure. The residue was purified by silica gel column chromatography (eluting solvent: ethyl acetate-hexane) to obtain the title compound (205 mg).
$^1$H-NMR (CDCl$_3$) δ ppm:
1.00 (9H, s), 2.60-2.75 (2H, m), 3.40-3.55 (1H, m), 3.74 (3H, s), 3.91 (3H, s), 4.25-4.40 (2H, m), 6.56 (1H, d, J=8.5 Hz), 6.60-6.75 (2H, m), 7.40 (1H, t, J=7.7 Hz), 7.55-7.65 (1H, m), 7.90-8.00 (1H, m), 8.05-8.15 (1H, m).

Reference Example 17 tert-Butyl[2-(2-cyclopentyl-2-hydroxyethyl)-4-methoxyphenyl]carbamate

[Chem. 33]

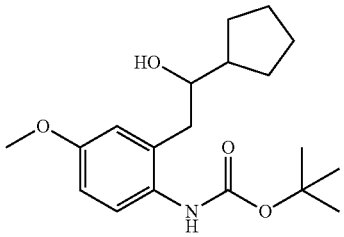 [SMILES: COc1ccc(NC(=O)OC(C)(C)C)c(CC(=O)c2ccoc2)c1]

To a solution of tert-butyl (4-methoxy-2-methylphenyl)carbamate (475 mg) in tetrahydrofuran (7 mL) was added dropwise sec-butyllithium (1.04 mol/L hexane-cyclohexane solution, 4.3 mL) at −40° C. under an argon atmosphere, and the mixture was stirred for 15 minutes. Then a solution of cyclopentanecarboxyaldehyde (0.256 mL) in tetrahydrofuran (1 mL) was added dropwise, and the mixture was stirred at −40° C. for 15 minutes and at room temperature for additional one hour. Water and 1 mol/L hydrochloric acid were added to the reaction mixture and this resulting mixture was extracted with ethyl acetate. The organic layer was washed with water and saturated saline, dried over anhydrous magnesium sulfate and concentrated under reduced pressure. The residue was purified by silica gel column chromatography (eluting solvent: ethyl acetate-hexane) to obtain the title compound (535 mg).
$^1$H-NMR (CDCl$_3$) δ ppm:
1.20-2.10 (19H, m), 2.70 (1H, dd, J=8.3, 14.0 Hz), 2.78 (1H, dd, J=2.9, 14.0 Hz), 3.55-3.70 (1H, m), 3.78 (3H, s), 6.69 (1H, d, J=3.0 Hz), 6.77 (1H, dd, J=3.0, 8.8 Hz), 7.40-7.70 (2H, m).

Reference Example 18

Methyl 3-{[2-(2-Cyclopentyl-2-hydroxyethyl)-4-methoxyphenylamino]methyl}benzoate

[Chem. 34]

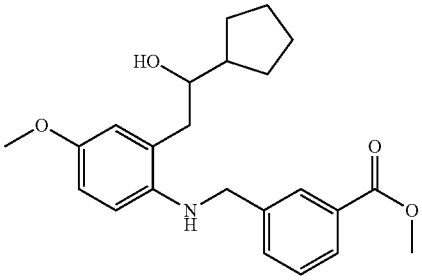

To a solution of tert-butyl[2-(2-cyclopentyl-2-hydroxyethyl)-4-methoxyphenyl]carbamate (530 mg) in dichloromethane (3 mL) was added trifluoroacetic acid (1 mL) at room temperature, and the mixture was stirred for one hour. The reaction mixture was poured into 5% aqueous sodium hydrogen carbonate solution (40 mL) and extracted with ethyl acetate. The organic layer was washed with saturated saline, dried over anhydrous magnesium sulfate and concentrated under reduced pressure. To a solution of the residue and methyl 3-formylbenzoate (318 mg) in acetic acid (3 mL) was added sodium triacetoxyborohydride (684 mg) at room temperature, and the mixture was stirred for one hour. The reaction mixture was diluted with ethyl acetate and washed with 5% aqueous sodium hydrogen carbonate solution. The organic layer was washed with saturated saline, dried over anhydrous magnesium sulfate and concentrated under reduced pressure. The residue was purified by silica gel column chromatography (eluting solvent: ethyl acetate-hexane) to obtain the title compound (362 mg).

$^1$H-NMR (CDCl$_3$) δ ppm:
1.20-1.70 (6H, m), 1.75-1.90 (2H, m), 1.90-2.10 (1H, m), 2.71 (1H, dd, J=8.3, 14.3 Hz), 2.79 (1H, dd, J=3.0, 14.3 Hz), 3.60-3.80 (4H, m), 3.91 (3H, s), 4.25-4.40 (2H, m), 6.55 (1H, d, J=8.6 Hz), 6.66 (1H, dd, J=2.8, 8.6 Hz), 6.70 (1H, d, J=2.8 Hz), 7.40 (1H, t, J=7.7 Hz), 7.55-7.65 m), 7.90-8.00 (1H, m), 8.00-8.10 (1H, m).

Reference Example 19

5-Difluoromethoxy-2-nitrobenzaldehyde

[Chem. 35]

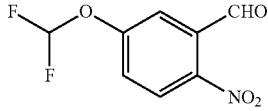

To a solution of 5-hydroxy-2-nitrobenzaldehyde (500 mg) in N,N-dimethylformamide (4.3 mL) were added sodium chlorodifluoroacetate (456 mg), sodium hydroxide (120 mg) and water (0.060 mL) at room temperature, and the mixture was stirred at 125° C. for one hour. The reaction mixture was cooled to room temperature, diluted with water and then extracted with ethyl acetate. The organic layer was washed successively with water and saturated saline, dried over anhydrous sodium sulfate and concentrated under reduced pressure. The residue was purified by silica gel column chromatography (eluting solvent: ethyl acetate-hexane) to obtain the title compound (240 mg).

$^1$H-NMR (CDCl$_3$) δ ppm:
6.68 (1H, t, J=71.5 Hz), 7.46 (1H, dd, J=2.7, 8.9 Hz), 7.64 (1H, d, J=2.7 Hz), 8.21 (1H, d, J=8.9 Hz), 10.46 (1H, s).

Reference Example 20

2-(2,2-Dibromovinyl)-4-difluoromethoxynitrobenzene

[Chem. 36]

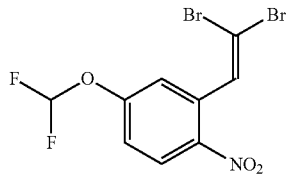

To a solution of 5-difluoromethoxy-2-nitrobenzaldehyde (238 mg) and carbon tetrabromide (545 mg) in dichloromethane (5.4 mL) was added dropwise a solution of triphenylphosphine (863 mg) in dichloromethane (3.6 mL) under cooling with ice. The mixture was gradually warmed to room temperature and stirred for 6 hours. The reaction mixture was concentrated under reduced pressure. The residue was suspended in diethyl ether and this resulting mixture was stirred at room temperature for 16 hours. The precipitate was removed by filtration through celite (registered trademark) and washed with diethyl ether. The filtrate was concentrated under reduced pressure to obtain the title compound (536 mg).

$^1$H-NMR (CDCl$_3$) δ ppm:
6.64 (1H, t, J=71.9 Hz), 7.20-7.30 (1H, m), 7.30-7.35 (1H, m), 7.77 (1H, s), 8.19 (1H, d, J=9.0 Hz).

Reference Example 21

2-(2,2-Dibromovinyl)-4-difluoromethoxyaniline

[Chem. 37]

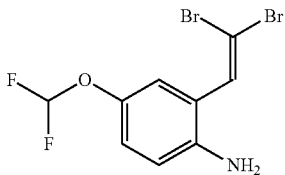

To a suspension of 2-(2,2-dibromovinyl)-4-difluoromethoxynitrobenzene (534 mg) in ethanol (3.7 mL) was added tin (II) chloride dihydrate (742 mg) at room temperature, and the mixture was heated under reflux for 3 hours. The reaction mixture was cooled to room temperature and concentrated under reduced pressure. 1 mol/L Aqueous sodium hydroxide solution was added to the residue and this resulting mixture was extracted with dichloromethane. The aqueous layer was extracted with dichloromethane. The combined organic layers were washed with saturated saline, dried over anhydrous sodium sulfate and concentrated under reduced pressure. The residue was purified by silica gel column chromatography (eluting solvent: ethyl acetate-hexane) to obtain the title compound (168 mg).

$^1$H-NMR (CDCl$_3$) δ ppm:
3.68 (2H, br s), 6.39 (1H, t, J=74.4 Hz), 6.67 (1H, d, J=8.8 Hz), 6.96 (1H, dd, J=2.8, 8.8 Hz), 7.13 (1H, d, J=2.8 Hz), 7.29 (1H, s).

Reference Example 22

5-Difluoromethoxy-2-phenylindole

[Chem. 38]

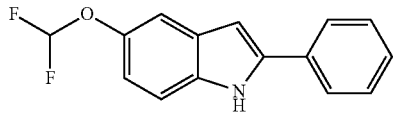

To a mixture of 2-(2,2-dibromovinyl)-4-difluoromethoxyaniline (166 mg), phenylboronic acid (88.5 mg) and potassium phosphate monohydrate (557 mg) was added a mixture of 2-dicyclohexylphosphino-2',6'-dimethoxybiphenyl (11.9 mg), palladium (II) acetate (3.3 mg) and toluene (2.4 mL) at room temperature, and the mixture was stirred at 100° C. for 3 hours. The reaction mixture was cooled to room temperature, diluted with ethyl acetate and then filtered through celite (registered trademark). The filtrate was washed with saturated saline-water (2/1), dried over anhydrous sodium sulfate and concentrated under reduced pressure. The residue was purified by silica gel column chromatography (eluting solvent: ethyl acetate-hexane) to obtain the title compound (91.2 mg).

$^1$H-NMR (CDCl$_3$) δ ppm:

6.51 (1H, t, J=75.1 Hz), 6.75-6.85 (1H, m), 7.00 (1H, dd, J=2.4, 8.7 Hz), 7.30-7.40 (3H, m), 7.40-7.50 (2H, m), 7.60-7.70 (2H, m), 8.37 (1H, br s).

Reference Example 23 tert-Butyl {2-[2-(3-fluorophenyl)-2-oxoethyl]-4-methoxyphenyl}carbamate

[Chem. 39]

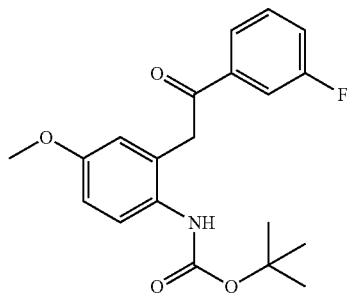

The title compound was synthesized in a manner similar to that of Reference Example 6-1 by using the corresponding starting material and reactants.

$^1$H-NMR (CDCl$_3$) δ ppm:

1.47 (9H, s), 3.76 (3H, s), 4.24 (2H, s), 6.65-7.15 (3H, m), 7.25-7.40 (1H, m), 7.40-7.60 (2H, m), 7.65-7.80 (1H, m), 7.80-7.90 (1H, m).

Reference Example 24

2-(3-Fluorophenyl)-5-methoxyindole

[Chem. 40]

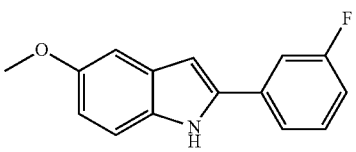

The title compound was synthesized in a manner similar to that of Reference Example 7-1 by using the corresponding starting material.

$^1$H-NMR (CDCl$_3$) δ ppm:

3.87 (3H, s), 6.75-6.80 (1H, m), 6.88 (1H, dd, J=2.4, 8.8 Hz), 6.95-7.05 (1H, m), 7.09 (1H, d, J=2.4 Hz), 7.25-7.50 (4H, m), 7.90-8.50 (1H, br).

Reference Example 25

5-Methylsulfanyl-2-phenylindole

[Chem. 41]

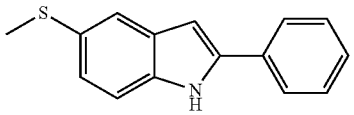

To a solution of 1-benzenesulfonyl-5-methylsulfanyl-2-phenylindole (264 mg) in tetrahydrofuran-methanol (2/1, 6.9 mL) was added cesium carbonate (680 mg) at room temperature, and the mixture was stirred at 50° C. for 26 hours. The reaction mixture was allowed to cool to ambient temperature and concentrated under reduced pressure. 1 mol/L Hydrochloric acid was added to the residue and this resulting mixture was extracted with ethyl acetate. The organic layer was washed successively with a saturated aqueous sodium hydrogen carbonate solution and saturated saline, dried over anhydrous sodium sulfate and concentrated under reduced pressure. The residue was purified by aminopropylated silica gel column chromatography (eluting solvent: ethyl acetate-hexane) to obtain the title compound (149 mg).

$^1$H-NMR (CDCl$_3$) δ ppm:

2.53 (3H, s), 6.75-6.80 (1H, m), 7.22 (1H, dd, J=1.9, 8.4 Hz), 7.30-7.50 (4H, m), 7.60-7.70 (3H, m), 8.35 (1H, br s).

Reference Example 26 tert-Butyl[4-methoxy-2-(2-oxazol-4-yl-2-oxoethyl)phenyl]carbamate

[Chem. 42]

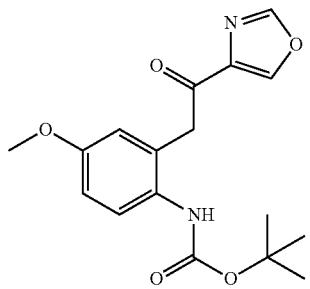

The title compound was synthesized in a manner similar to that of Reference Example 6-1 by using the corresponding starting material and reactants.

$^1$H-NMR (CDCl$_3$) δ ppm:

1.52 (9H, s), 3.76 (3H, s), 4.17 (2H, s), 6.75-6.90 (2H, m), 7.35-8.00 (3H, m), 8.28 (1H, d, J=1.0 Hz).

Reference Example 27

5-Methoxy-2-oxazol-4-ylindole

[Chem. 43]

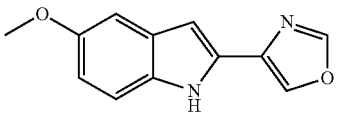 [SMILES: COc1ccc2[nH]c(-c3ccoc3)cc2c1]

The title compound was synthesized in a manner similar to that of Reference Example 7-1 by using the corresponding starting material.

$^1$H-NMR (CDCl$_3$) δ ppm:
3.86 (3H, s), 6.65-6.75 (1H, m), 6.86 (1H, dd, J=2.5, 8.8 Hz), 7.06 (1H, d, J=2.5 Hz), 7.29 (1H, d, J=8.8 Hz), 7.90-8.05 (2H, m), 8.50-9.05 (1H, br).

Reference Example 28 tert-Butyl {2-[2-(2-fluorophenyl)-2-oxoethyl]-4-methoxyphenyl}carbamate

[Chem. 44]

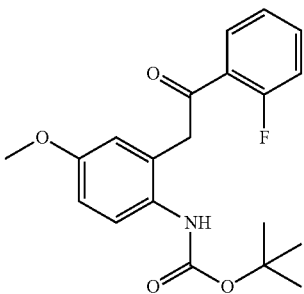

The title compound was synthesized in a manner similar to that of Reference Example 6-1 by using the corresponding starting material and reactants.

$^1$H-NMR (CDCl$_3$) δ ppm:
1.47 (9H, s), 3.76 (3H, s), 4.20-4.35 (2H, m), 6.60-7.10 (3H, m), 7.10-7.30 (2H, m), 7.30-7.70 (2H, m), 7.80-7.90 (1H, m).

Reference Example 29

2-(2-Fluorophenyl)-5-methoxyindole

[Chem. 45]

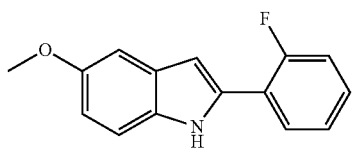

The title compound was synthesized in a manner similar to that of Reference Example 7-1 by using the corresponding starting material and reactant.

$^1$H-NMR (CDCl$_3$) δ ppm:
3.87 (3H, s), 6.80-6.95 (2H, m), 7.05-7.35 (5H, m), 7.70-7.85 (1H, m), 8.40-9.15 (1H, br).

Reference Example 30 tert-Butyl {2-[2-(4-fluorophenyl)-2-oxoethyl]-4-methoxyphenyl}carbamate

[Chem. 46]

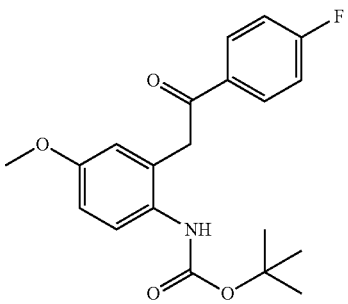

The title compound was synthesized in a manner similar to that of Reference Example 6-1 by using the corresponding starting material and reactants.

$^1$H-NMR (CDCl$_3$) δ ppm:
1.48 (9H, s), 3.75 (3H, s), 4.23 (2H, s), 6.70-7.70 (6H, m), 8.00-8.20 (2H, m).

Reference Example 31

2-(4-Fluorophenyl)-5-methoxyindole

[Chem. 47]

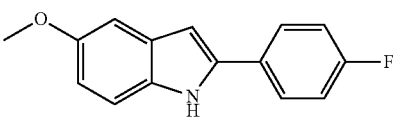

The title compound was synthesized in a manner similar to that of Reference Example 7-1 by using the corresponding starting material and reactant.

$^1$H-NMR (CDCl$_3$) δ ppm:
3.86 (3H, s), 6.65-6.75 (1H, m), 6.86 (1H, dd, J=2.5, 8.8 Hz), 7.00-7.20 (3H, m), 7.28 (1H, d, J=8.8 Hz), 7.55-7.65 (2H, m), 7.90-8.40 (1H, br).

Reference Example 32

Methyl 5-hydroxymethylthiophene-3-carboxylate

[Chem. 48]

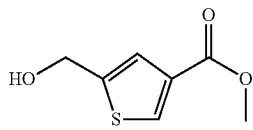

To a solution of methyl 5-formylthiophene-3-carboxylate (500 mg) in ethanol (5.9 mL) was added sodium borohydride (55.6 mg) at room temperature in small portions, and the mixture was stirred for one hour. The reaction mixture was concentrated under reduced pressure. A saturated aqueous sodium hydrogen carbonate solution was added to the residue and this resulting mixture was extracted with ethyl acetate. The aqueous layer was extracted once again with ethyl acetate. The combined organic layers were dried over anhydrous sodium sulfate and concentrated under reduced pressure. The residue was purified by silica gel column chromatography (eluting solvent: ethyl acetate-hexane) to obtain the title compound (403 mg).

$^1$H-NMR (CDCl$_3$) δ ppm:
1.86 (1H, t, J=6.0 Hz), 3.86 (3H, s), 4.75-4.90 (2H, m), 7.35-7.45 (1H, m), 8.04 (1H, d, J=1.3 Hz).

Reference Example 33

Methyl 5-bromomethylthiophene-3-carboxylate

[Chem. 49]

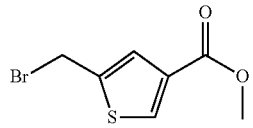

To a solution of methyl 5-hydroxymethylthiophene-3-carboxylate (401 mg) in ethyl acetate (4.7 mL) were added triethylamine (0.390 mL) and methanesulfonyl chloride (0.198 mL) under cooling with ice. The mixture was stirred under cooling with ice for 40 minutes. The reaction mixture was diluted with ethyl acetate (4.7 mL) and filtered through celite (registered trademark). To the filtrate was added lithium bromide monohydrate (733 mg) at room temperature, and the mixture was stirred at 50° C. for 6 hours. The reaction mixture was allowed to cool to ambient temperature, diluted with water and extracted with ethyl acetate. The organic layer was washed successively with water and saturated saline, dried over anhydrous sodium sulfate and concentrated under reduced pressure. The residue was purified by silica gel column chromatography (eluting solvent: ethyl acetate-hexane) to obtain the title compound (495 mg).

$^1$H-NMR (CDCl$_3$) δ ppm:
3.86 (3H, s), 4.68 (2H, s), 7.45-7.55 (1H, m), 8.07 (1H, d, J=1.3 Hz).

Reference Example 34 tert-Butyl {2-[2-(3-chlorophenyl)-2-oxoethyl]-4-methoxyphenyl}carbamate

The title compound was synthesized in a manner similar to that of Reference Example 6-1 by using the corresponding starting material and reactants.

$^1$H-NMR (CDCl$_3$) δ ppm:
1.47 (9H, s), 3.76 (3H, s), 4.24 (2H, s), 6.60-7.20 (3H, m), 7.35-7.65 (3H, m), 7.85-8.10 (2H, m).

Reference Example 35

2-(3-Chlorophenyl)-5-methoxyindole

The title compound was synthesized in a manner similar to that of Reference Example 7-1 by using the corresponding starting material and reactant.

$^1$H-NMR (CDCl$_3$) δ ppm:
3.87 (3H, s), 6.75-6.80 (1H, m), 6.88 (1H, dd, J=2.5, 8.8 Hz), 7.05-7.15 (1H, m), 7.20-7.35 (2H, m), 7.36 (1H, t, J=7.8 Hz), 7.45-7.55 (1H, m), 7.60-7.65 (1H, m), 8.00-8.40 (1H, br).

Reference Example 36

N-(2-Bromo-5-chloro-4-methoxyphenyl)-2,2,2-trifluoroacetamide

To a solution of 2-bromo-5-chloro-4-methoxyaniline (8.97 g) in pyridine (25.3 mL) was added dropwise trifluoroacetic anhydride (2.81 mL) under cooling with ice. The mixture was stirred at room temperature for 30 hours. Methanol (1.5 mL) was added to the reaction mixture and the stirring was continued for additional 40 minutes. The reaction mixture was concentrated under reduced pressure. 1 mol/L Hydrochloric acid was added to the residue and this resulting mixture was extracted with ethyl acetate. The organic layer was washed successively with 1 mol/L hydrochloric acid, a saturated aqueous sodium hydrogen carbonate solution and saturated saline, dried over anhydrous sodium sulfate and concentrated under reduced pressure to obtain the title compound (3.45 g).

$^1$H-NMR (DMSO-d$_6$) δ ppm:
3.92 (3H, s), 7.51 (1H, s), 7.61 (1H, s), 11.21 (1H, s).

Reference Example 37

6-Chloro-5-methoxy-2-phenylindole

To a mixture of N-(2-bromo-5-chloro-4-methoxyphenyl)-2,2,2-trifluoroacetamide (512 mg), phenylacetylene (0.254 mL), copper (I) iodide (17.5 mg), triethylamine (549 mL) and acetonitrile (12.3 mL) was added bis(triphenylphosphine)palladium (II) dichloride (32.5 mg). The mixture was stirred at 120° C. for 2 hours under irradiation of microwave. The reaction mixture was allowed to cool to ambient temperature. Potassium carbonate (532 mg) was added to the reaction mixture. The mixture was stirred at 120° C. for additional 2 hours under irradiation of microwave. The reaction mixture was allowed to cool to ambient temperature and filtered through celite (registered trademark). The filtrate was concentrated under reduced pressure and the residue was purified by aminopropylated silica gel column chromatography (eluting solvent: ethyl acetate-hexane) to obtain the title compound (255 mg).

$^1$H-NMR (CDCl$_3$) δ ppm:
3.95 (3H, s), 6.70-6.80 (1H, m), 7.13 (1H, s), 7.30-7.50 (4H, m), 7.60-7.70 (2H, m), 8.00-8.40 (1H, br).

Reference Example 38

N-(2-Bromo-4-methoxy-5-methylphenyl)-2,2,2-trifluoroacetamide

The title compound was synthesized in a manner similar to that of Reference Example 36 by using the corresponding starting material.

$^1$H-NMR (DMSO-d$_6$) δ ppm:
2.11 (3H, s), 3.83 (3H, s), 7.15-7.30 (2H, m), 11.08 (1H, s).

Reference Example 39

5-Methoxy-6-methyl-2-phenylindole

The title compound was synthesized in a manner similar to that of Reference Example 37 by using the corresponding starting material.

¹H-NMR (CDCl₃) δ ppm:
2.34 (3H, s), 3.88 (3H, s), 6.70-6.80 (1H, m), 7.02 (1H, s), 7.10-7.35 (2H, m), 7.35-7.50 (2H, m), 7.55-7.70 (2H, m), 8.13 (1H, br s).

Reference Example 40

6-Chloro-2-(2-fluorophenyl)-5-methoxyindole

The title compound was synthesized in a manner similar to that of Reference Example 37 by using the corresponding starting material and reactant.
¹H-NMR (CDCl₃) δ ppm:
3.95 (3H, s), 6.80-6.95 (1H, m), 7.10-7.35 (4H, m), 7.40-7.50 (1H, m), 7.70-7.85 (1H, m), 8.76 (1H, br s).

Reference Example 41

6-Chloro-2-(3-fluorophenyl)-5-methoxyindole

The title compound was synthesized in a manner similar to that of Reference Example 37 by using the corresponding starting material and reactant.
¹H-NMR (CDCl₃) δ ppm:
3.95 (3H, s), 6.70-6.80 (1H, m), 6.95-7.10 (1H, m), 7.12 (1H, s), 7.25-7.50 (4H, m), 8.19 (1H, br s).

Reference Example 42

6-Chloro-2-(4-fluorophenyl)-5-methoxyindole

The title compound was synthesized in a manner similar to that of Reference Example 37 by using the corresponding starting material and reactant.
¹H-NMR (CDCl₃) δ ppm:
3.94 (3H, s), 6.60-6.75 (1H, m), 7.10-7.20 (3H, m), 7.35-7.45 (1H, m), 7.55-7.70 (2H, m), 8.13 (1H, br s).

Reference Example 43

Methyl 6-(1-bromoethyl)pyridine-2-carboxylate

To a solution of methyl 6-ethylpyridine-2-carboxylate (587 mg) in carbon tetrachloride (28.4 mL) were added N-bromosuccinimide (696 mg) and benzoyl peroxide (75%, 11.5 mg). The mixture was heated under reflux for 4 hours. The reaction mixture was allowed to cool to ambient temperature. The insoluble material was removed by filtration and the filtrate was concentrated under reduced pressure. The residue was purified by silica gel column chromatography (eluting solvent: ethyl acetate-hexane) to obtain the title compound (702 mg).
¹H-NMR (CDCl₃) δ ppm:
2.08 (3H, d, J=7.0 Hz), 4.01 (3H, s), 5.34 (1H, q, J=7.0 Hz), 7.70-7.95 (2H, m), 8.00-8.10 (1H, m).

Reference Example 44

N-(2-Bromo-5-fluoro-4-methoxyphenyl)-2,2,2-trifluoroacetamide

The title compound was synthesized in a manner similar to that of Reference Example 36 by using the corresponding starting material.

¹H-NMR (DMSO-d₆) δ ppm:
3.90 (3H, s), 7.47 (1H, d, J=11.8 Hz), 7.54 (1H, d, J=8.8 Hz), 11.21 (1H, s).

Reference Example 45

6-Fluoro-(2-fluorophenyl)-5-methoxyindole

The title compound was synthesized in a manner similar to that of Reference Example 37 by using the corresponding starting material and reactant.
¹H-NMR (CDCl₃) δ ppm:
3.94 (3H, s), 6.80-6.90 (1H, m), 7.05-7.40 (5H, m), 7.65-7.85 (1H, m), 8.55-9.00 (1H, br).

Reference Example 46

6-Fluoro-2-(3-fluorophenyl)-5-methoxyindole

The title compound was synthesized in a manner similar to that of Reference Example 37 by using the corresponding starting material and reactants.
¹H-NMR (CDCl₃) δ ppm:
3.94 (3H, s), 6.70-6.80 (1H, m), 6.95-7.10 (1H, m), 7.10-7.20 (2H, m), 7.25-7.45 (3H, m), 8.00-8.40 (1H, br).

Reference Example 47

6-Fluoro-2-(4-fluorophenyl)-5-methoxyindole

The title compound was synthesized in a manner similar to that of Reference Example 37 by using the corresponding starting material and reactants.
¹H-NMR (CDCl₃) δ ppm:
3.94 (3H, s), 6.60-6.75 (1H, m), 7.05-7.20 (4H, m), 7.50-7.65 (2H, m), 8.00-8.30 (1H, br).

Reference Example 48

6-Fluoro-5-methoxy-2-pyridin-3-ylindole

The title compound was synthesized in a manner similar to that of Reference Example 37 by using the corresponding starting material and reactant.
¹H-NMR (CDCl₃) δ ppm:
3.94 (3H, s), 6.75-6.85 (1H, m), 7.10-7.25 (2H, m), 7.30-7.45 (1H, m), 7.85-8.00 (1H, m), 8.40-8.75 (2H, m), 8.85-9.00 (1H, m).

Reference Example 49 tert-Butyl (5-chloro-4-methoxy-2-methylphenyl)carbamate

The title compound was synthesized in a manner similar to that of Reference Example 5 by using the corresponding starting material.
¹H-NMR (CDCl₃) δ ppm:
1.51 (9H, s), 2.23 (3H, s), 3.86 (3H, s), 5.65-6.40 (1H, br), 6.72 (1H, s), 7.40-8.10 (1H, br).

Reference Example 50 tert-Butyl[5-chloro-4-methoxy-2-(2-oxo-2-thiophen-3-ylethyl)phenyl]carbamate

The title compound was synthesized in a manner similar to that of Reference Example 6-1 by using the corresponding starting material and reactants.

¹H-NMR (CDCl₃) δ ppm:
1.49 (9H, s), 3.85 (3H, s), 4.16 (2H, s), 6.73 (1H, s), 6.90-8.00 (4H, m), 8.15-8.30 (1H, m).

Reference Example 51

6-Fluoro-5-methoxy-2-thiophen-3-ylindole

The title compound was synthesized in a manner similar to that of Reference Example 7-1 by using the corresponding starting material and reactant.
¹H-NMR (CDCl₃) δ ppm:
3.94 (3H, s), 6.55-6.70 (1H, m), 7.10 (1H, s), 7.35-7.50 (4H, m), 7.90-8.35 (1H, br).

Reference Example 52

4-Benzyloxy-2-bromo-5-chloroaniline

To a suspension of 4-benzyloxy-3-chloroaniline (674 mg) and potassium carbonate (1.14 g) in dichloromethane (32 mL) was added dropwise a solution of bromine (1.25 g) in dichloromethane (16 mL) at −15° C. in one hour, and the mixture was stirred at −15° C. for 75 minutes. Water was added to the reaction mixture and this resulting mixture was stirred vigorously for additional 10 minutes. The organic layer was separated, dried over anhydrous sodium sulfate and concentrated under reduced pressure. The residue was purified by silica gel column chromatography (eluting solvent: ethyl acetate-hexane) to obtain the title compound (1.13 g).
¹H-NMR (CDCl₃) δ ppm:
3.85 (2H, br s), 5.03 (2H, s), 6.84 (1H, s), 7.07 (1H, s), 7.25-7.55 (5H, m).

Reference Example 53

N-(4-benzyloxy-2-bromo-5-chlorophenyl)-2,2,2-trifluoroacetamide

The title compound was synthesized in a manner similar to that of Reference Example 36 by using the corresponding starting material.
¹H-NMR (DMSO-d₆) δ ppm:
5.29 (2H, s), 7.30-7.55 (5H, m), 7.55-7.70 (2H, m), 11.22 (1H, s).

Reference Example 54

5-Benzyloxy-6-chloro-2-phenylindole

The title compound was synthesized in a manner similar to that of Reference Example 37 by using the corresponding starting material.
¹H-NMR (CDCl₃) δ ppm:
5.19 (2H, s), 6.65-6.80 (1H, m), 7.18 (1H, s), 7.25-7.75 (11H, m), 8.23 (1H, br s).

Reference Example 55

Methyl 6-(5-benzyloxy-6-chloro-2-phenylindol-1-ylmethyl)pyridine-2-carboxylate

To a solution of 5-benzyloxy-6-chloro-2-phenylindole (513 mg) in N,N-dimethylformamide (7.7 mL) was added sodium hydride (in oil, 50 to 72%, 92 mg) under cooling with ice under an argon atmosphere, and the mixture was stirred at room temperature for one hour. Then methyl 6-(chloromethyl)pyridine-2-carboxylate (342 mg) was added, and the mixture was stirred at 80° C. for 18 hours. The reaction mixture was allowed to cool to ambient temperature. A saturated aqueous ammonium chloride solution and water were added to the reaction mixture and this resulting mixture was extracted with ethyl acetate. The organic layer was washed successively with water and saturated saline, dried over anhydrous sodium sulfate and concentrated under reduced pressure. The residue was purified by silica gel column chromatography (eluting solvent: ethyl acetate-hexane) to obtain the title compound (454 mg).
¹H-NMR (CDCl₃) δ ppm:
4.03 (3H, s), 5.20 (2H, s), 5.54 (2H, s), 6.55-6.65 (1H, m), 6.65-6.75 (1H, m), 7.15-7.60 (12H, m), 7.65-7.75 (1H, m), 7.95-8.10 (1H, m).

Reference Example 56

Methyl 6-(6-chloro-5-hydroxy-2-phenylindole-1-ylmethyl)pyridine-2-carboxylate

A solution of methyl 6-(5-benzyloxy-6-chloro-2-phenylindol-1-ylmethyl)pyridine-2-carboxylate (372 mg) in trifluoroacetic acid/water/dimethyl sulfide (95/5/10, 7.7 mL) was stirred at room temperature for 80 hours. The reaction mixture was concentrated under reduced pressure. A saturated aqueous sodium hydrogen carbonate solution (20 mL) was added to the residue and this resulting mixture was extracted with ethyl acetate. The organic layer was dried over anhydrous sodium sulfate and concentrated under reduced pressure. The residue was triturated in dichloromethane/hexane (2/1). The precipitate was collected by filtration, washed with dichloromethane/hexane (2/1), and air-dried to obtain the title compound (213 mg).
¹H-NMR (CDCl₃) δ ppm:
4.03 (3H, s), 5.33 (1H, s), 5.53 (2H, s), 6.57 (1H, s), 6.69 (1H, d, J=7.8 Hz), 7.12 (1H, s), 7.28 (1H, s), 7.30-7.50 (5H, m), 7.65-7.80 (1H, m), 8.01 (1H, d, J=7.5 Hz).

Reference Example 57 tert-Butyl[5-chloro-4-methoxy-2-(2-oxo-2-furan-3-ylethyl)phenyl]carbamate

The title compound was synthesized in a manner similar to that of Reference Example 6-1 by using the corresponding starting material and reactants.
¹H-NMR (CDCl₃) δ ppm:
1.50 (9H, s), 3.85 (3H, s), 4.01 (2H, s), 6.70 (1H, s), 6.75-6.85 (1H, m), 7.00-8.00 (3H, m), 8.15-8.25 (1H, m).

Reference Example 58

6-Chloro-2-furan-3-yl-5-methoxyindole

The title compound was synthesized in a manner similar to that of Reference Example 7-1 by using the corresponding starting material.
¹H-NMR (CDCl₃) δ ppm:
3.94 (3H, s), 6.45-6.60 (1H, m), 6.60-6.75 (1H, m), 7.09 (1H, s), 7.35-7.40 (1H, m), 7.45-7.55 (1H, m), 7.70-7.80 (1H, m), 7.80-8.20 (1H, br).

Reference Example 59 tert-Butyl (4-hydroxy-2,5-dimethylphenyl)carbamate

A mixture of 4-amino-2,5-dimethylphenol (2.00 g), di-tert-butyl dicarbonate (3.50 g) and tetrahydrofuran (29 mL)

was heated under reflux overnight. The reaction mixture was allowed to cool to ambient temperature and concentrated under reduced pressure to obtain the title compound (3.80 g).
$^1$H-NMR (CDCl$_3$) δ ppm:
1.51 (9H, s), 2.16 (3H, s), 2.18 (3H, s), 4.60-5.00 (1H, br), 5.80-6.25 (1H, br), 6.55 (1H, s), 7.20-7.45 (1H, br).

Reference Example 60 tert-Butyl (4-methoxy-2,5-dimethylphenyl)carbamate

To a solution of tert-butyl (4-hydroxy-2,5-dimethylphenyl)carbamate (1.25 g) and methyl iodide (1.12 g) in N,N-dimethylformamide (10.5 mL) was added potassium carbonate (1.46 g), and the mixture was stirred at room temperature for 3 hours. The reaction mixture was diluted with water and extracted with ethyl acetate. The organic layer was washed successively with water and saturated saline, dried over anhydrous sodium sulfate and concentrated under reduced pressure. The residue was purified by silica gel column chromatography (eluting solvent: ethyl acetate-hexane) to obtain the title compound (1.32 g).
$^1$H-NMR (CDCl$_3$) δ ppm:
1.51 (9H, s), 2.17 (3H, s), 2.22 (3H, s), 3.79 (3H, s), 5.75-6.30 (1H, br), 6.62 (1H, s), 7.20-7.55 (1H, br).

Reference Example 61 tert-Butyl[4-methoxy-5-methyl-2-(2-oxo-2-thiophen-3-ylethyl)phenyl]carbamate

The title compound was synthesized in a manner similar to that of Reference Example 6-1 by using the corresponding starting material and reactants.
$^1$H-NMR (CDCl$_3$) δ ppm:
1.49 (9H, s), 2.18 (3H, s), 3.77 (3H, s), 4.15 (2H, s), 6.61 (1H, s), 6.80-7.70 (4H, m), 8.15-8.30 (1H, m).

Reference Example 62

5-Methoxy-6-methyl-2-thiophen-3-ylindole

The title compound was synthesized in a manner similar to that of Reference Example 7-1 by using the corresponding starting material.
$^1$H-NMR (CDCl$_3$) δ ppm:
2.30-2.40 (3H, m), 3.88 (3H, s), 6.55-6.65 (1H, m), 7.00 (1H, s), 7.13 (1H, s), 7.30-7.45 (3H, m), 8.02 (1H, br s).

Reference Example 63 tert-Butyl[5-chloro-4-methoxy-2-(2-oxo-2-pyridin-3-ylethyl)phenyl]carbamate

The title compound was synthesized in a manner similar to that of Reference Example 6-1 by using the corresponding starting material and reactants.
$^1$H-NMR (CDCl$_3$) δ ppm:
1.47 (9H, s), 3.85 (3H, s), 4.29 (2H, s), 6.50-7.20 (2H, m), 7.40-7.90 (2H, m), 8.25-8.35 (1H, m), 8.75-8.90 (1H, m), 9.25-9.35 (1H, m).

Reference Example 64

6-Chloro-5-methoxy-2-pyridin-3-ylindole

The title compound was synthesized in a manner similar to that of Reference Example 7-1 by using the corresponding starting material.

$^1$H-NMR (CDCl$_3$) δ ppm:
3.95 (3H, s), 6.75-6.85 (1H, m), 7.14 (1H, s), 7.38 (1H, dd, J=4.8, 8.0 Hz), 7.45 (1H, s), 7.85-8.00 (1H, m), 8.36 (1H, br s), 8.50-8.65 (1H, m), 8.90-9.00 (1H, m).

Reference Example 65

1-Benzenesulfonyl-5-bromo-2-phenylindole

To a suspension of sodium hydride (in oil, minimum 55%, 801 mg) in N,N-dimethylformamide (30 mL) was added dropwise a solution of 5-bromo-2-phenylindole (3.33 g) in N,N-dimethylformamide (30 mL) under cooling with ice and under an argon atmosphere, and the mixture was stirred at room temperature for one hour and a half. Then benzenesulfonyl chloride (1.88 mL) was added dropwise and the stirring was continued for additional 17 hours. A saturated aqueous ammonium chloride solution and water were added to the reaction mixture and this resulting mixture was extracted with ethyl acetate. The organic layer was washed with water and saturated saline, dried over anhydrous sodium sulfate and concentrated under reduced pressure. The residue was purified by silica gel column chromatography (eluting solvent: ethyl acetate-hexane) to obtain the title compound (1.87 g).
$^1$H-NMR (CDCl$_3$) δ ppm:
6.48 (1H, s), 7.15-7.65 (12H, m), 8.19 (1H, d, J=8.8 Hz).

Reference Example 66

1-Benzenesulfonyl-5-formyl-2-phenylindole

To a solution of 1-benzenesulfonyl-5-bromo-2-phenylindole (958 mg) in tetrahydrofuran (11.6 mL) was added dropwise n-butyllithium (2.76 mol/L hexane solution, 0.84 mL) at −78° C. under an argon atmosphere, and the mixture was stirred for 30 minutes. Then N,N-dimethylformamide (0.535 mL) was added dropwise, and the mixture was stirred at −78° C. for 30 minutes and at room temperature for 2 hours. A saturated aqueous ammonium chloride solution and water were added to the reaction mixture and this resulting mixture was extracted with ethyl acetate. The organic layer was washed with saturated saline, dried over anhydrous sodium sulfate and concentrated under reduced pressure. The residue was purified by silica gel column chromatography (eluting solvent: ethyl acetate-hexane) to obtain the title compound (225 mg).
$^1$H-NMR (CDCl$_3$) δ ppm:
6.60-6.70 (1H, m), 7.20-7.55 (10H, m), 7.91 (1H, dd, J=1.6, 8.7 Hz), 7.95-8.05 (1H, m), 8.47 (1H, d, J=8.7 Hz), 10.07 (1H, s).

Reference Example 67

1-Benzenesulfonyl-5-hydroxymethyl-2-phenylindole

To a suspension of 1-benzenesulfonyl-5-formyl-2-phenylindole (224 mg) in ethanol (2.5 mL) was added sodium borohydride (11.7 mg), and the mixture was stirred at room temperature for one hour. A saturated aqueous ammonium chloride solution was added to the reaction mixture and the resulting mixture was extracted with ethyl acetate. The organic layer was washed with saturated saline, dried over anhydrous sodium sulfate and concentrated under reduced pressure. The residue was purified by silica gel column chromatography (eluting solvent: ethyl acetate-hexane) to obtain the title compound (173 mg).

¹H-NMR (CDCl₃) δ ppm:
1.68 (1H, br s), 4.77 (2H, s), 6.50-6.60 (1H, m), 7.20-7.55 (12H, m), 8.29 (1H, d, J=8.5 Hz).

Reference Example 68

1-Benzenesulfonyl-2-phenyl-5-triisopropylsilanyloxymethylindole

To a solution of 1-benzenesulfonyl-5-hydroxymethyl-2-phenylindole (171 mg) in N,N-dimethylformamide (2.4 mL) were added imidazole (128 mg) and chlorotriisopropylsilane (0.150 mL) under cooling with ice, and the mixture was stirred at room temperature for 20 hours. Water was added to the reaction mixture and this resulting mixture was extracted with ethyl acetate. The organic layer was washed with water, dried over anhydrous sodium sulfate and concentrated under reduced pressure. The residue was purified by silica gel column chromatography (eluting solvent: ethyl acetate-hexane) to obtain the title compound (221 mg).
¹H-NMR (CDCl₃) δ ppm:
0.95-1.30 (21H, m), 4.90 (2H, s), 6.50-6.60 (1H, m), 7.20-7.55 (12H, m), 8.25 (1H, d, J=8.8 Hz).

Reference Example 69

2-Phenyl-5-triisopropylsilanyloxymethylindole

The title compound was synthesized in a manner similar to that of Reference Example 25 by using the corresponding starting material.
¹H-NMR (CDCl₃) δ ppm:
1.00-1.35 (21H, m), 4.93 (2H, s), 6.75-6.85 (1H, m), 7.15-7.25 (1H, m), 7.25-7.40 (2H, m), 7.40-7.50 (2H, m), 7.55-7.75 (3H, m), 8.15-8.45 (1H, br).

Reference Example 70

Methyl 6-(2-phenyl-6-triisopropylsilanyloxymethylindol-1-ylmethyl)pyridine-2-carboxylate The title compound was synthesized in a manner similar to that of Reference Example 55 by using the corresponding starting material and reactants.
¹H-NMR (CDCl₃) δ ppm:
1.05-1.25 (21H, m), 4.03 (3H, s), 4.93 (2H, s), 5.60 (2H, s), 6.65-6.75 (2H, m), 7.08 (1H, d, J=8.3 Hz), 7.10-7.20 (1H, m), 7.30-7.45 (5H, m), 7.60-7.70 (2H, m), 7.95-8.05 (1H, m).

Reference Example 71 tert-Butyl[5-chloro-2-(2-hydroxy-3-methylpentyl)-4-methoxyphenyl]carbamate

The title compound was synthesized in a manner similar to that of Reference Example 14 by using the corresponding starting material and reactants.
¹H-NMR (CDCl₃) δ ppm:
0.50-2.30 (19H, m), 2.45-2.95 (2H, m), 3.55-4.05 (4H, m), 6.60-6.80 (1H, m), 7.20-8.00 (2H, m).

Reference Example 72

1-(2-Amino-4-chloro-5-methoxyphenyl)-3-methylpentan-2-ol

The title compound was synthesized in a manner similar to that of Reference Example 15 by using the corresponding starting material.

¹H-NMR (CDCl₃) δ ppm:
0.75-1.75 (9H, m), 2.45-2.85 (2H, m), 3.30-4.10 (6H, m), 6.60-6.80 (2H, m).
ESI-MS (m/z): 258, 260 (M+H)⁺.

Reference Example 73

6-Chloro-5-methoxy-2-(1-methylpropyl)indole

A mixture of 1-(2-amino-4-chloro-5-methoxyphenyl)-3-methylpentan-2-ol (602 mg), tetrakis(triphenylphosphine)palladium (0) (135 mg), potassium carbonate (646 mg), 2-bromomesitylene (0.420 mL) and N,N-dimethylformamide (11.7 mL) was stirred at 160° C. for one hour under microwave irradiation. The reaction mixture was allowed to cool to ambient temperature. Water was added to the reaction mixture and this resulting mixture was extracted with ethyl acetate. The organic layer was washed with saturated saline, dried over anhydrous sodium sulfate and concentrated under reduced pressure. The residue was purified by silica gel column chromatography (eluting solvent: ethyl acetate-hexane) to obtain the title compound (514 mg).
¹H-NMR (CDCl₃) δ ppm:
0.91 (3H, t, J=7.4 Hz), 1.32 (3H, d, J=6.8 Hz), 1.55-1.80 (2H, m), 2.70-2.90 (1H, m), 3.91 (3H, s), 6.10-6.20 (1H, m), 7.05 (1H, s), 7.25-7.35 (1H, m), 7.50-8.00 (1H, br).

Reference Example 74 tert-Butyl (4-cyclopropyl-2-methylphenyl)carbamate

A mixture of tert-butyl (4-iodo-2-methylphenyl)carbamate (1.04 g), cyclopropylboronic acid monohydrate (422 mg), palladium acetate (35.1 mg), tricyclohexylphosphine (87.5 mg), tripotassium phosphate monohydrate (2.52 g), toluene (8.7 mL) and water (0.87 mL) was stirred at 100° C. for 15 hours. The reaction mixture was allowed to cool to ambient temperature, diluted with ethyl acetate and filtered through celite (registered trademark). The filtrate was washed with water/saturated saline (1/1, 20 mL), dried over anhydrous sodium sulfate and concentrated under reduced pressure. The residue was purified by silica gel column chromatography (eluting solvent: ethyl acetate-hexane) to obtain the title compound (668 mg).
¹H-NMR (CDCl₃) δ ppm:
0.55-0.70 (2H, m), 0.80-1.00 (2H, m), 1.51 (9H, s), 1.75-1.90 (1H, m), 2.21 (3H, s), 5.85-6.45 (1H, br), 6.75-7.00 (2H, m), 7.45-7.75 (1H, m).

Reference Example 75 tert-Butyl[4-cyclopropyl-2-(2-oxo-2-phenylethyl)phenyl]carbamate

The title compound was synthesized in a manner similar to that of Reference Example 6-1 by using the corresponding starting material and reactants.
¹H-NMR (CDCl₃) δ ppm:
0.55-0.70 (2H, m), 0.80-1.00 (2H, m), 1.49 (9H, s), 1.75-1.90 (1H, m), 4.25 (2H, s), 6.85-7.00 (2H, m), 7.20-7.75 (5H, m), 8.00-8.15 (2H, m).

Reference Example 76

5-Cyclopropyl-2-phenylindole

The title compound was synthesized in a manner similar to that of Reference Example 7-1 by using the corresponding starting material and reactant.

¹H-NMR (CDCl₃) δ ppm:
0.65-0.75 (2H, m), 0.85-1.00 (2H, m), 1.95-2.10 (1H, m), 6.70-6.80 (1H, m), 6.90-7.00 (1H, m), 7.25-7.50 (5H, m), 7.60-7.70 (2H, m), 8.24 (1H, br s).

Example 1-1

Methyl 6-(5-chloro-2-phenylindol-1-ylmethyl)pyridine-2-carboxylate

To a solution of 5-chloro-2-phenylindole (154 mg) in N,N-dimethylformamide (1.5 mL) was added sodium hydride (dispersed in liquid paraffin, minimum 55%, 31 mg) at room temperature, and the mixture was stirred for 15 minutes. Methyl 6-(chloromethyl)pyridine-2-carboxylate (126 mg) was added and this resulting mixture was stirred at 50 to 60° C. for additional 18 hours. Water, ethyl acetate and a saturated aqueous ammonium chloride solution were added to the reaction mixture. The organic layer was separated. The aqueous layer was extracted with ethyl acetate. The combined organic layers were washed successively with water and saturated saline, dried over anhydrous sodium sulfate and concentrated under reduced pressure. The residue was purified by aminopropylated silica gel column chromatography (eluting solvent: ethyl acetate-hexane) to obtain the title compound (112 mg).

In addition, structural formula and spectrum data of the title compound are shown in Table 5.

Examples 1-2 to 1-8

The compounds shown in Tables 5 to 6 were synthesized in a manner similar to that of Example 1-1 by using the corresponding starting materials.

TABLE 5

| Ex. No. | Strc | Physical data |
|---|---|---|
| 1-1 | 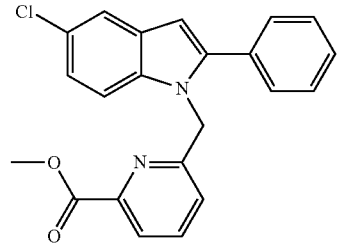 | ¹H-NMR (CDCl₃) δ ppm:<br>4.03 (3H, s), 5.59 (2H, s), 6.60-6.70 (2H, m), 7.00-7.15 (2H, m), 7.35-7.45 (5H, m), 7.60-7.75 (2H, m), 7.95-8.05 (1H, m). |
| 1-2 | 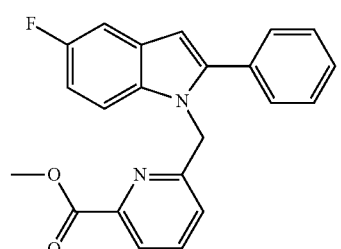 | ¹H-NMR (CDCl₃) δ ppm:<br>4.02 (3H, s), 5.59 (2H, s), 6.60-6.75 (2H, m), 6.85-6.95 (1H, m), 7.04 (1H, dd, J = 4.3, 8.8 Hz), 7.25-7.50 (6H, m), 7.60-7.75 (1H, m), 8.00 (1H, d, J = 7.5 Hz). |
| 1-3 | 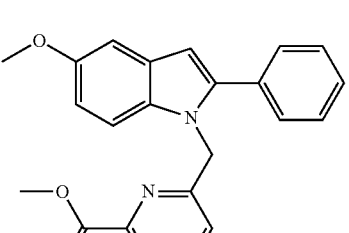 | ¹H-NMR (CDCl₃) δ ppm:<br>3.87 (3H, s), 4.02 (3H, s), 5.58 (2H, s), 6.60-6.75 (2H, m), 6.81 (1H, dd, J = 2.5, 8.8 Hz), 7.02 (1H, d, J = 8.8 Hz), 7.15 (1H, d, J = 2.5 Hz), 7.30-7.45 (5H, m), 7.60-7.70 (1H, m), 7.95-8.05 (1H, m). |
| 1-4 | 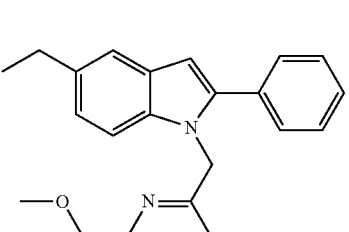 | ¹H-NMR (CDCl₃) δ ppm:<br>1.29 (3H, t, J = 7.5 Hz), 2.75 (2H, q, J = 7.5 Hz), 4.03 (3H, s), 5.59 (2H, s), 6.55-6.80 (2H, m), 6.95-7.10 (2H, m), 7.25-7.60 (6H, m), 7.60-7.75 (1H, m), 7.90-8.05 (1H, m). |

TABLE 5-continued

| Ex. No. | Strc | Physical data |
|---|---|---|
| 1-5 | (structure) | ¹H-NMR (CDCl₃) δ ppm: 3.86 (3H, s), 4.05 (3H, s), 5.63 (2H, s), 6.60-6.70 (1H, m), 6.70-6.80 (1H, m), 6.81 (1H, dd, J = 2.5, 8.8 Hz), 7.03 (1H, d, J = 8.8 Hz), 7.13 (1H, d, J = 2.5 Hz), 7.16 (1H, dd, J = 1.3, 5.0 Hz), 7.23 (1H, dd, J = 1.3, 3.0 Hz), 7.36 (1H, dd, J = 3.0, 5.0 Hz), 7.68 (1H, t, J = 7.8 Hz), 7.95-8.05 (1H, m). |

TABLE 6

| Ex. No. | Strc | Physical data |
|---|---|---|
| 1-6 | (structure) | ¹H-NMR (CDCl₃) δ ppm: 1.27 (6H, d, J = 6.8 Hz), 2.85-3.00 (1H, m), 3.84 (3H, s), 4.05 (3H, s), 5.55 (2H, s), 6.34 (1H, s), 6.40-6.50 (1H, m), 6.74 (1H, dd, J = 2.5, 8.8 Hz), 6.98 (1H, d, J = 8.8 Hz), 7.08 (1H, d, J = 2.5 Hz), 7.55-7.65 (1H, m), 7.95-8.05 (1H, m). |
| 1-7 | (structure) | ¹H-NMR (CDCl₃) δ ppm: 4.03 (3H, s), 5.60 (2H, s), 6.30-6.80 (3H, m), 6.95 (1H, dd, J = 2.3, 8.8 Hz), 7.09 (1H, d, J = 8.8 Hz), 7.35-7.50 (6H, m), 7.65-7.75 (1H, m), 7.95-8.05 (1H, m). |
| 1-8 | (structure) | ¹H-NMR (CDCl₃) δ ppm: 0.93 (6H, d, J = 6.8 Hz), 1.80-1.95 (1H, m), 2.52 (2H, d, J = 7.0 Hz), 3.84 (3H, s), 4.05 (3H, s), 5.51 (2H, s), 6.31 (1H, s), 6.44 (1H, d, J = 7.8 Hz), 6.74 (1H, dd, J = 2.4, 8.9 Hz), 6.99 (1H, d, J = 8.9 Hz), 7.07 (1H, d, J = 2.4 Hz), 7.61 (1H, t, J = 7.8 Hz), 7.99 (1H, d, J = 7.8 Hz). |

Example 2-1

Ethyl 5-(5-chloro-2-isopropylindol-1-ylmethyl)furan-2-carboxylate

To a solution of 5-chloro-2-isopropylindole (136 mg) in N,N-dimethylformamide (2 mL) was added sodium hydride (dispersed in liquid paraffin, minimum 55%, 32 mg) under cooling with ice, and the mixture was stirred for 30 minutes. Then ethyl 5-(chloromethyl)furan-2-carboxylate (0.107 mL) was added, and the mixture was stirred at 60° C. for 20 hours. A saturated aqueous ammonium chloride solution was added to the reaction mixture and this resulting mixture was extracted with ethyl acetate. The aqueous layer was extracted with ethyl acetate. The combined organic layers were washed with saturated saline, dried over anhydrous magnesium sulfate and concentrated under reduced pressure. The residue was purified by silica gel column chromatography (eluting solvent: ethyl acetate-hexane) to obtain the title compound (133 mg).

In addition, structural formula and spectrum data of the title compound are shown in Table 7.

Examples 2-2 to 2-7

The compounds shown in Tables 7 to 8 were synthesized in a manner similar to that of Example 2-1 by using the corresponding starting materials.

TABLE 7

| Ex. No. | Strc | Physical data |
|---|---|---|
| 2-1 | 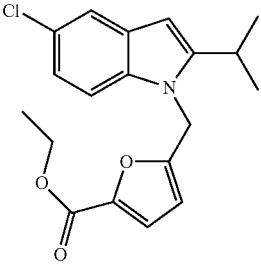 [SMILES: CCOC(=O)c1ccc(Cn2c(C(C)C)cc3cc(Cl)ccc32)o1] | $^1$H-NMR (CDCl$_3$) δ ppm:<br>1.30-1.40 (9H, m), 2.95-3.15 (1H, m), 4.35 (2H, q, J = 7.0 Hz), 5.32 (2H, s), 5.80-5.85 (1H, m), 6.29 (1H, s), 6.95-7.15 (3H, m), 7.45-7.55 (1H, m). |
| 2-2 | 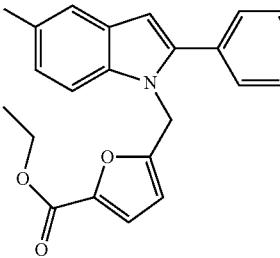 | $^1$H-NMR (CDCl$_3$) δ ppm:<br>1.37 (3H, t, J = 7.1 Hz), 4.34 (2H, q, J = 7.1 Hz), 5.30 (2H, s), 5.97 (1H, d, J = 3.4 Hz), 6.55 (1H, s), 7.04 (1H, d, J = 3.4 Hz), 7.16 (1H, dd, J = 2.0, 8.7 Hz), 7.22 (1H, d, J = 8.7 Hz), 7.35-7.55 (5H, m), 7.55-7.65 (1H, m). |
| 2-3 | 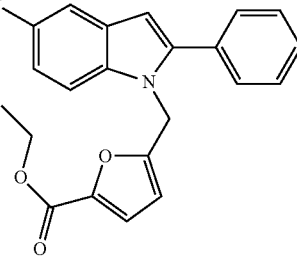 | $^1$H-NMR (CDCl$_3$) δ ppm:<br>1.37 (3H, t, J = 7.1 Hz), 4.35 (2H, q, J = 7.1 Hz), 5.30 (2H, s), 5.95-6.05 (1H, m), 6.55-6.60 (1H, m), 6.95 (1H, dt, J = 2.4, 9.0 Hz), 7.05 (1H, d, J = 3.5 Hz), 7.22 (1H, dd, J =4.4, 9.0 Hz), 7.29 (1H, dd, J = 2.4, 9.4Hz), 7.35-7.55 (5H, m). |
| 2-4 | 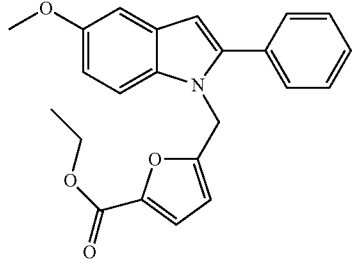 [SMILES: CCOC(=O)c1ccc(Cn2c(-c3ccccc3)cc3cc(OC)ccc32)o1] | $^1$H-NMR (CDCl$_3$) δ ppm:<br>1.37 (3H, t, J = 7.2 Hz), 3.87 (3H, s), 4.35 (2H, q, J = 7.2 Hz), 5.29 (2H, s), 5.95-6.05 (1H, m), 6.50-6.60 (1H, m), 6.87 (1H, dd, J = 2.4, 9.0 Hz), 7.05 (1H, d, J = 3.5 Hz), 7.12 (1H, d, J = 2.4 Hz), 7.19 (1H, d, J = 9.0 Hz), 7.35-7.55 (5H, m). |
| 2-5 | 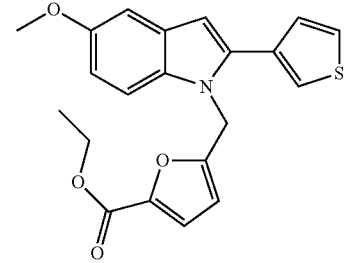 [SMILES: CCOC(=O)c1ccc(Cn2c(-c3ccsc3)cc3cc(OC)ccc32)o1] | $^1$H-NMR (CDCl$_3$) δ ppm:<br>1.37 (3H, t, J =7.2 Hz), 3.86 (3H, s), 4.35 (2H, q, J = 7.2 Hz), 5.34 (2H, s), 6.00-6.05 (1H, m), 6.55-6.60 (1H, m), 6.86 (1H, dd, J = 2.5, 8.8 Hz), 7.06 (1H, d, J = 3.3 Hz), 7.09 (1H, d, J = 2.5 Hz), 7.18 (1H, d, J = 8.8 Hz), 7.24 (1H, dd, J = 1.3, 5.0 Hz), 7.37 (1H, dd, J = 1.3, 2.9 Hz), 7.41 (1H, dd, J = 2.9, 5.0 Hz). |

TABLE 8

| Ex. No. | Strc | Physical data |
|---|---|---|
| 2-6 | 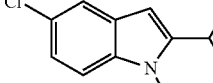 | ¹H-NMR (CDCl₃) δ ppm: 1.32 (6H, d, J = 7.0 Hz), 1.36 (3H, t, J = 7.1 Hz), 2.95-3.10 (1H, m), 3.83 (3H, s), 4.35 (2H, q, J = 7.1 Hz), 5.30 (2H, s), 5.80-5.90 (1H, m), 6.27 (1H, s), 6.78 (1H, dd, J = 2.5, 8.8 Hz), 7.00 (1H, d, J = 3.3 Hz), 7.04 (1H, d, J = 2.5 Hz), 7.10 (1H, d, J = 8.8 Hz). |
| 2-7 | 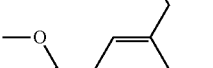 | ¹H-NMR (CDCl₃) δ ppm: 0.98 (6H, d, J = 6.5 Hz), 1.37 (3H, t, J = 7.1 Hz), 1.85-2.05 (1H, m), 2.59 (2H, d, J = 7.3 Hz), 3.84 (3H, s), 4.35 (2H, q, J = 7.1 Hz), 5.27 (2H, s), 5.82 (1H, d, J = 3.5 Hz), 6.24 (1H, s), 6.78 (1H, dd, J = 2.3, 9.0 Hz), 7.00 (1H, d, J = 3.5 Hz), 7.03 (1H, d, J = 2.3 Hz), 7.10 (1H, d, J = 9.0 Hz). |

Example 3-1

Methyl 3-(5-methoxy-2-phenylindol-1-ylmethyl)benzoate

To a solution of 5-methoxy-2-phenylindole (73.0 mg) in N,N-dimethylformamide (1.6 mL) was added sodium hydride (dispersed in liquid paraffin, minimum 55%, 22 mg) under cooling with ice, and the mixture was stirred at room temperature for 70 minutes. Then methyl 3-(bromomethyl) benzoate (89.9 mg) was added, and the mixture was stirred at 100° C. for 6 hours. The reaction mixture was cooled to room temperature. Saturated ammonium chloride-water (2/1) were added and this resulting mixture was extracted with ethyl acetate. The organic layer was washed with saturated saline, dried over anhydrous sodium sulfate and concentrated under reduced pressure. The residue was purified by aminopropylated silica gel column chromatography (eluting solvent: ethyl acetate-hexane) to obtain the title compound (50.6 mg).

In addition, structural formula and spectrum data of the title compound are shown in Table 9.

Examples 3-2 to 3-22

The compounds shown in Tables 9 to 12 were synthesized in a manner similar to that of Example 3-1 by using the corresponding starting materials.

TABLE 9

| Ex. No. | Strc | Physical data |
|---|---|---|
| 3-1 | 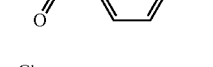 | ¹H-NMR (CDCl₃) δ ppm: 3.86 (3H, s), 3.89 (3H, s), 5.36 (2H, s), 6.55-6.65 (1H, m), 6.80 (1H, dd, J = 2.5, 8.8 Hz), 7.03 (1H, d, J = 8.8 Hz), 7.05-7.20 (2H, m), 7.25-7.50 (6H, m), 7.75-7.85 (1H, m), 7.85-7.95 (1H, m). |
| 3-2 | 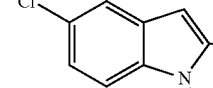 | ¹H-NMR (CDCl₃) δ ppm: 3.89 (3H, s), 5.38 (2H, s), 6.55-6.65 (1H, m), 7.00-7.15 (3H, m), 7.30-7.45 (6H, m), 7.60-7.65 (1H, m), 7.75-7.80 (1H, m), 7.85-7.95 (1H, m). |
| 3-3 |  | ¹H-NMR (CDCl₃) δ ppm: 1.29 (6H, d, J = 7.0 Hz), 2.85-3.05 (1H, m), 3.90 (3H, s), 5.37 (2H, s), 6.33 (1H, s), 6.80-7.10 (3H, m), 7.25-7.35 (1H, m), 7.50-7.60 (1H, m), 7.75-7.95 (2H, m). |
| 3-4 | 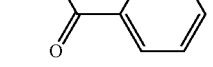 | ¹H-NMR (CDCl₃) δ ppm: 3.89 (3H, s), 5.39 (2H, s), 6.60-6.70 (1H, m), 6.95-7.15 (3H, m), 7.30-7.45 (6H, m), 7.50-7.55 (1H, m), 7.75-7.85 (1H, m), 7.90-8.00 (1H, m). |
| 3-5 | 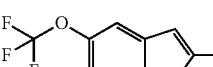 | ¹H-NMR (CDCl₃) δ ppm: 3.89 (3H, s), 5.43 (2H, s), 6.74 (1H, s), 7.05-7.15 (1H, m), 7.22 (1H, d, J = 8.8 Hz), 7.30-7.50 (7H, m), 7.75-7.85 (1H, m), 7.90-8.00 (2H, m). |
| 3-6 | 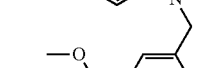 | ¹H-NMR (CDCl₃) δ ppm: 3.89 (3H, s), 5.38 (2H, s), 6.62 (1H, s), 6.89 (1H, dt, J = 2.5, 9.0 Hz), 7.00-7.15 (2H, m), 7.25-7.50 (7H, m), 7.75-7.85 (1H, m), 7.85-7.95 (1H, m). |

TABLE 10

| Ex. No. | Strc | Physical data |
|---|---|---|
| 3-7 | 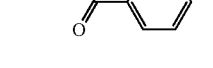 | ¹H-NMR (CDCl₃) δ ppm: 3.98 (3H, s), 5.42 (2H, s), 6.70-6.75 (1H, m), 7.00-7.10 (1H, m), 7.20 (1H, d, J = 8.5 Hz), 7.30-7.50 (7H, m), 7.70-7.80 (1H, m), 7.90-8.05 (2H, m). |

TABLE 10-continued

| Ex. No. | Strc | Physical data |
|---|---|---|
| 3-8 | 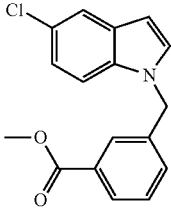 | ¹H-NMR (CDCl₃) δ ppm: 0.86 (3H, t, J = 7.4 Hz), 1.25 (3H, d, J = 7.0 Hz), 1.45-1.80 (2H, m), 2.65-2.80 (1H, m), 3.89 (3H, s), 5.36 (2H, s), 6.30 (1H, s), 6.85-7.10 (3H, m), 7.20-7.35 (1H, m), 7.50-7.60 (1H, m), 7.75-7.95 (2H, m). |
| 3-9 | 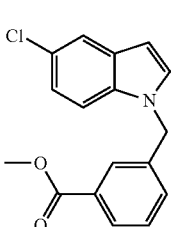 | ¹H-NMR (CDCl₃) δ ppm: 0.95 (6H, d, J = 6.5 Hz), 1.80-2.00 (1H, m), 2.54 (2H, d, J = 7.3 Hz), 3.89 (3H, s), 5.32 (2H, s), 6.30 (1H, s), 6.85-7.10 (3H, m), 7.20-7.40 (1H, m), 7.45-7.60 (1H, m), 7.75-7.85 (1H, m), 7.85-8.00 (1H, m). |
| 3-10 | 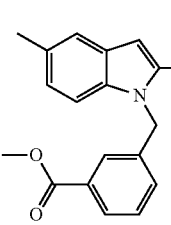 | ¹H-NMR (CDCl₃) δ ppm: 2.45 (3H, s), 3.88 (3H, s), 5.37 (2H, s), 6.55-6.60 (1H, m), 6.90-7.15 (3H, m), 7.25-7.50 (7H, m), 7.80-7.95 (2H, m). |
| 3-11 | 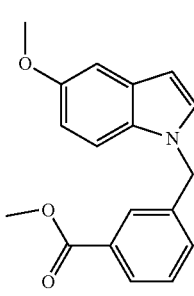 | ¹H-NMR (CDCl₃) δ ppm: 1.28 (6H, d, J = 6.8 Hz), 2.85-3.05 (1H, m), 3.83 (3H, s), 3.90 (3H, s), 5.35 (2H, s), 6.25-6.35 (1H, m), 6.73 (1H, dd, J = 2.3, 8.9 Hz), 6.85-6.95 (1H, m), 6.99 (1H, d, J = 8.9 Hz), 7.07 (1H, d, J = 2.3 Hz), 7.20-7.35 (1H, m), 7.80-7.95 (2H, m). |

TABLE 11

| Ex. No. | Strc | Physical data |
|---|---|---|
| 3-12 | 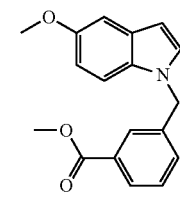 | ¹H-NMR (CDCl₃) δ ppm: 0.86 (3H, t, J = 7.4 Hz), 1.24 (3H, d, J = 6.8 Hz), 1.45-1.85 (2H, m), 2.65-2.80 (1H, m), 3.84 (3H, s), 3.89 (3H, s), 5.34 (2H, s), 6.29 (1H, s), 6.74 (1H, dd, J = 2.5, 8.8 Hz), 6.85-7.00 (1H, m), 7.02 (1H, d, J = 8.8 Hz), 7.07 (1H, d, J = 2.5 Hz), 7.29 (1H, t, J = 7.8 Hz), 7.75-7.95 (2H, m). |
| 3-13 | 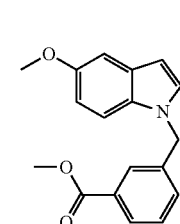 | ¹H-NMR (CDCl₃) δ ppm: 0.95 (6H, d, J = 6.5 Hz), 1.80-2.00 (1H, m), 2.54 (2H, d, J = 7.3 Hz), 3.84 (3H, s), 3.89 (3H, s), 5.31 (2H, s), 6.28 (1H, s), 6.73 (1H, dd, J = 2.5, 8.8 Hz), 6.90-7.10 (3H, m), 7.29 (1H, t, J = 7.8 Hz), 7.80-7.95 (2H, m). |

TABLE 11-continued

| Ex. No. | Strc | Physical data |
|---|---|---|
| 3-14 | 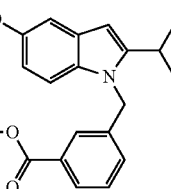 | ¹H-NMR (CDCl₃) δ ppm: 0.79 (6H, t, J = 7.4 Hz), 1.55-1.70 (4H, m), 2.50-2.65 (1H, m), 3.85 (3H, s), 3.89 (3H, s), 5.34 (2H, s), 6.27 (1H, s), 6.74 (1H, dd, J = 2.5, 8.8 Hz), 6.90-7.10 (3H, m), 7.20-7.35 (1H, m), 7.80-7.95 (2H, m). |
| 3-15 | 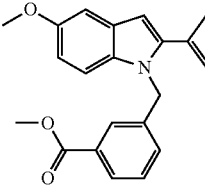 | ¹H-NMR (CDCl₃) δ ppm: 3.86 (3H, s), 3.89 (3H, s), 5.42 (2H, s), 6.60-6.65 (1H, m), 6.81 (1H, dd, J = 2.5, 9.0 Hz), 7.04 (1H, d, J = 9.0 Hz), 7.05-7.25 (4H, m), 7.30-7.40 (2H, m), 7.80-8.00 (2H, m). |
| 3-16 | 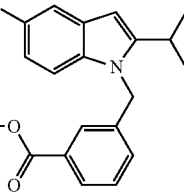 | ¹H-NMR (CDCl₃) δ ppm: 0.79 (6H, t, J = 7.4 Hz), 1.55-1.75 (4H, m), 2.50-2.65 (1H, m), 3.89 (3H, s), 5.36 (2H, s), 6.29 (1H, s), 6.90-7.10 (3H, m), 7.30 (1H, t, J = 7.7 Hz), 7.50-7.60 (1H, m), 7.75-7.85 (1H, m), 7.85-7.95 (1H, m). |

TABLE 12

| Ex. No. | Strc | Physical data |
|---|---|---|
| 3-17 | 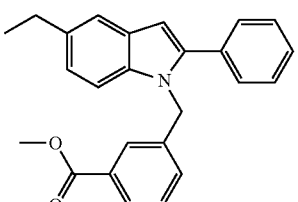 | ¹H-NMR (CDCl₃) δ ppm: 1.29 (3H, t, J = 7.6 Hz), 2.75 (2H, q, J = 7.6 Hz), 3.89 (3H, s), 5.37 (2H, s), 6.55-6.65 (1H, m), 6.95-7.20 (3H, m), 7.25-7.55 (7H, m), 7.80-7.95 (2H, m). |
| 3-18 | 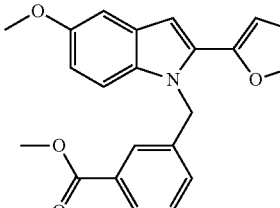 | ¹H-NMR (CDCl₃) δ ppm: 3.86 (3H, s), 3.89 (3H, s), 5.55 (2H, s), 6.35-6.50 (2H, m), 6.78 (1H, s), 6.83 (1H, dd, J = 2.5, 8.8 Hz), 7.05-7.15 (3H, m), 7.25-7.35 (1H, m), 7.40-7.50 (1H, m), 7.85-7.95 (2H, m). |
| 3-19 | 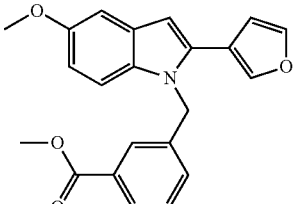 | ¹H-NMR (CDCl₃) δ ppm: 3.86 (3H, s), 3.89 (3H, s), 5.42 (2H, s), 6.45-6.55 (1H, m), 6.55-6.65 (1H, m), 6.81 (1H, dd, J = 2.4, 8.9 Hz), 7.00-7.15 (3H, m), 7.33 (1H, t, J = 7.8 Hz), 7.40-7.50 (2H, m), 7.80-8.00 (2H, m). |

TABLE 12-continued

| Ex. No. | Strc | Physical data |
|---|---|---|
| 3-20 | (5-methoxy-2-cyclopropyl-indole with N-CH2-benzoate-OMe) | ¹H-NMR (CDCl₃) δ ppm: 0.65-0.75 (2H, m), 0.80-0.95 (2H, m), 1.65-1.80 (1H, m), 3.83 (3H, s), 3.90 (3H, s), 5.47 (2H, s), 6.13 (1H, s), 6.75 (1H, dd, J = 2.4, 8.9 Hz), 6.95-7.10 (3H, m), 7.25-7.35 (1H, m), 7.85-7.95 (2H, m). |
| 3-21 | (5-methoxy-6-fluoro-2-phenyl-indole with N-CH2-benzoate-OMe) | ¹H-NMR (CDCl₃) δ ppm: 3.89 (3H, s), 3.94 (3H, s), 5.32 (2H, s), 6.57 (1H, s), 6.86 (1H, d, J = 11.6 Hz), 7.05-7.15 (1H, m), 7.19 (1H, d, J = 8.3 Hz), 7.30-7.50 (6H, m), 7.75-7.80 (1H, m), 7.85-8.00 (1H, m). |
| 3-22 | (5-difluoromethoxy-2-phenyl-indole with N-CH2-benzoate-OMe) | ¹H-NMR (CDCl₃) δ ppm: 3.89 (3H, s), 5.38 (2H, s), 6.50 (1H, t, J = 74.9 Hz), 6.64 (1H, s), 6.95 (1H, dd, J = 2.3, 8.8 Hz), 7.05-7.15 (2H, m), 7.30-7.50 (7H, m), 7.75-8.00 (2H, m). |

Example 4

Methyl 3-(5-ethoxy-2-phenylindol-1-ylmethyl)benzoate

[Chem. 50]

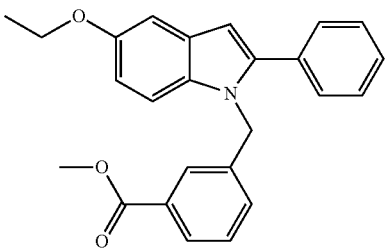

A suspension of methyl 3-{[2-(2,2-dibromovinyl)-4-ethoxyphenylamino]methyl}benzoate (258 mg), phenylboronic acid (134 mg), tris(dibenzylideneacetone)dipalladium (0) (25.1 mg), tris(2-methylphenyl)phosphine and potassium carbonate (381 mg) in toluene (5 mL) was stirred at 85° C. for 3.5 hours under an argon atmosphere. The reaction mixture was cooled to room temperature, diluted with ethyl acetate and filtered through celite (registered trademark). The filtrate was concentrated under reduced pressure. The residue was purified by aminopropylated silica gel column chromatography (eluting solvent: ethyl acetate-hexane) to obtain the title compound (138 mg).

¹H-NMR (CDCl₃) δ ppm:
1.44 (3H, t, J=6.9 Hz), 3.88 (3H, s), 4.08 (2H, q, J=6.9 Hz), 5.36 (2H, s), 6.55-6.60 (1H, m), 6.80 (1H, dd, J=2.5, 8.8 Hz), 7.02 (1H, d, J=8.8 Hz), 7.05-7.45 (8H, m), 7.75-7.85 (1H, m), 7.85-7.95 (1H, m).

Example 5-1

Methyl 2-fluoro-5-(5-methoxy-2-phenylindol-1-ylmethyl)benzoate

To a solution of 5-methoxy-2-phenylindole (90.9 mg) in N,N-dimethylformamide (1.8 mL) was added sodium hydride (dispersed in liquid paraffin, minimum 55%, 18 mg) under cooling with ice and an argon atmosphere, and the mixture was stirred under cooling with ice for 5 minutes and then at room temperature for 15 minutes. Methyl 5-(bromomethyl)-2-fluorobenzoate (101 mg) was added at room temperature, and the mixture was stirred at 80° C. for 13 hours. The reaction mixture was poured into a saturated aqueous ammonium chloride solution and extracted with ethyl acetate. The organic layer was washed with water and saturated saline, dried over anhydrous sodium sulfate and concentrated under reduced pressure. The residue was purified by silica gel column chromatography to obtain the title compound (53.2 mg).

In addition, structural formula and spectrum data of the title compound are shown in Table 13.

Examples 5-2 to 5-6

The compounds shown in Table 13 were synthesized in a manner similar to that of Example 5-1 by using the corresponding reactants.

TABLE 13

| Ex. No. | Strc | Physical data |
|---|---|---|
| 5-1 | (5-methoxy-2-phenyl-indole, N-CH2-(2-fluoro-benzoate-OMe)) | ¹H-NMR (CDCl₃) δ ppm: 3.86 (3H, s), 3.90 (3H, s), 5.31 (2H, s), 6.55-6.60 (1H, m), 6.75-6.90 (1H, m), 6.90-7.45 (9H, m), 7.65-7.70 (1H, m). ESI-MS (m/z): 390 (M + H)⁺ |
| 5-2 | (5-methoxy-2-phenyl-indole, N-CH2-benzoate-OMe with F) | ¹H-NMR (CDCl₃) δ ppm: 3.87 (3H, s), 3.89 (3H, s), 5.34 (2H, s), 6.55-6.65 (1H, m), 6.70-6.90 (2H, m), 7.02 (1H, d, J = 8.8 Hz), 7.14 (1H, d, J = 2.3 Hz), 7.30-7.50 (5H, m), 7.50-7.65 (2H, m). |
| 5-3 | (5-methoxy-2-phenyl-indole, N-CH2-benzoate-OMe with Cl) | ¹H-NMR (CDCl₃) δ ppm: 3.87 (3H, s), 3.96 (3H, s), 5.41 (2H, s), 6.60-6.65 (1H, m), 6.65-6.75 (1H, m), 6.82 (1H, dd, J = 2.5, 8.8 Hz), 6.96 (1H, d, J = 8.8 Hz), 7.05-7.45 (7H, m), 7.60-7.70 (1H, m). |

TABLE 13-continued

| Ex. No. | Strc | Physical data |
|---|---|---|
| 5-4 | | ¹H-NMR (CDCl₃) δ ppm: 3.86 (3H, s), 3.89 (3H, s), 5.38 (2H, s), 6.60 (1H, s), 6.83 (1H, dd, J = 2.5, 8.8 Hz), 7.05 (1H, d, J = 8.8 Hz), 7.13 (1H, d, J = 2.5 Hz), 7.30-7.50 (5H, m), 7.80-7.95 (1H, m), 8.30-8.45 (1H, m), 9.00-9.10 (1H, m). |
| 5-5 | | ¹H-NMR (CDCl₃) δ ppm: 1.32 (3H, t, J = 7.1 Hz), 3.87 (3H, s), 4.29 (2H, q, J = 7.1 Hz), 5.42 (2H, s), 6.50-6.60 (1H, m), 6.65-6.75 (1H, m), 6.86 (1H, dd, J = 2.4, 8.9 Hz), 7.12 (1H, d, J = 2.4 Hz), 7.18 (1H, d, J = 8.9 Hz), 7.35-7.50 (5H, m), 7.58 (1H, d, J = 3.8 Hz). |
| 5-6 | | ¹H-NMR (CDCl₃) δ ppm: 3.87 (3H, s), 3.94 (3H, s), 5.41 (2H, s), 6.60 (1H, s), 6.70-6.90 (2H, m), 6.95-7.10 (2H, m), 7.14 (1H, d, J = 2.5 Hz), 7.30-7.45 (5H, m), 7.75-7.85 (1H, m). |

Example 6

Ethyl[3-(5-methoxy-2-phenylindol-1-ylmethyl)phenoxy]acetate

[Chem. 51]

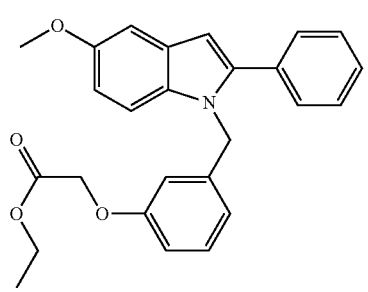

To a solution of 1-(3-hydroxybenzyl)-5-methoxy-2-phenylindole (108 mg) in N,N-dimethylformamide (1.3 mL) was added potassium carbonate (68.2 mg) at room temperature. Then ethyl bromoacetate (0.047 mL) was added, and the mixture was stirred at room temperature for 3 hours. The reaction mixture was diluted with water and extracted with ethyl acetate. The organic layer was washed with saturated saline, dried over anhydrous sodium sulfate and concentrated under reduced pressure. The residue was purified by silica gel column chromatography (eluting solvent: ethyl acetate-hexane) to obtain the title compound (129 mg).

¹H-NMR (CDCl₃) δ ppm:
1.25 (3H, t, J=7.2 Hz), 3.86 (3H, s), 4.20 (2H, q, J=7.2 Hz), 4.51 (2H, s), 5.29 (2H, s), 6.50-6.85 (5H, m), 7.05 (1H, d, J=8.8 Hz), 7.12 (1H, d, J=2.3 Hz), 7.15-7.25 (1H, m), 7.30-7.50 (5H, m).

Example 7

Methyl 3-(2-tert-butyl-5-methoxyindol-1-ylmethyl)benzoate

[Chem. 52]

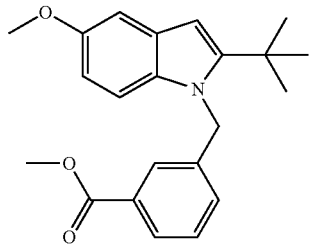

To a suspension of methyl 3-{[2-(2-hydroxy-3,3-dimethylbutyl)-4-methoxyphenylamino]methyl}benzoate (200 mg), 2-bromomesitylene (0.097 mL) and potassium carbonate (148 mg) in N,N-dimethylformamide (5 mL) was added tetrakis(triphenylphosphine)palladium (0) (31.1 mg) at room temperature, and this resulting mixture was stirred at 150° C. for 2 hours under an argon atmosphere. The reaction mixture was cooled to room temperature, diluted with water and extracted with ethyl acetate. The organic layer was washed with saturated saline, dried over anhydrous magnesium sulfate and concentrated under reduced pressure. The residue was purified by silica gel column chromatography (eluting solvent: ethyl acetate-hexane) to obtain the title compound (127 mg).

¹H-NMR (CDCl₃) δ ppm:
1.40 (9H, s), 3.82 (3H, s), 3.90 (3H, s), 5.59 (2H, s), 6.30-6.40 (1H, m), 6.68 (1H, dd, J=2.4, 8.9 Hz), 6.75-6.90 (2H, m), 7.05 (1H, d, J=2.4 Hz), 7.20-7.35 (1H, m), 7.75-7.95 (2H, m).

Example 8

Methyl 3-(2-cyclopentyl-5-methoxyindol-1-ylmethyl)benzoate

[Chem. 53]

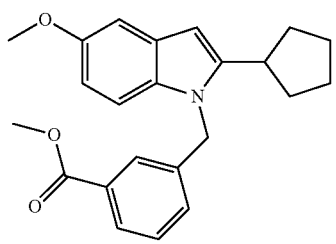

The title compound was synthesized in a manner similar to that of Example 7 by using the corresponding starting material.

¹H-NMR (CDCl₃) δ ppm:
1.55-1.90 (6H, m), 1.90-2.10 (2H, m), 2.95-3.10 (1H, m), 3.83 (3H, s), 3.90 (3H, s), 5.37 (2H, s), 6.31 (1H, s), 6.72 (1H, dd, J=2.5, 8.8 Hz), 6.90-7.10 (3H, m), 7.20-7.35 (1H, m), 7.80-7.95 (2H, m).

Example 9-1

3-(5-Methoxy-2-phenylindol-1-ylmethyl)benzoic acid

To a solution of methyl 3-(5-methoxy-2-phenylindol-1-ylmethyl)benzoate (48.6 mg) in tetrahydrofuran-methanol (7/3, 1.1 mL) was added 2 mol/L aqueous sodium hydroxide solution (0.196 mL) at room temperature, and the mixture was stirred at 60° C. for 2 hours. 1 mol/L Hydrochloric acid (10 mL) was added to the reaction mixture at room temperature and this resulting mixture was extracted with ethyl acetate. The organic layer was washed successively with water and saturated saline, dried over anhydrous sodium sulfate and concentrated under reduced pressure to obtain the title compound (44.7 mg).

In addition, structural formula and spectrum data of the title compound are shown in Table 14.

Examples 9-2 to 9-47

The compounds shown in Tables 14 to 22 were synthesized in a manner similar to that of Example 9-1 by using the corresponding starting materials.

TABLE 14

| Ex. No. | Strc | Physical data |
|---|---|---|
| 9-1 | (structure) | $^1$H-NMR (DMSO-$d_6$) δ ppm: 3.77 (3H, s), 5.50 (2H, s), 6.60 (1H, s), 6.76 (1H, dd, J = 2.5, 8.8 Hz), 7.05-7.15 (2H, m), 7.26 (1H, d, J = 8.8 Hz), 7.30-7.55 (7H, m), 7.70-7.80 (1H, m), 12.95 (1H, s). |
| 9-2 | (structure) | $^1$H-NMR (DMSO-$d_6$) δ ppm: 5.47 (2H, s), 6.20 (1H, d, J = 3.5 Hz), 6.62 (1H, s), 7.05 (1H, d, J = 3.5 Hz), 7.18 (1H, dd, J = 2.1, 8.7 Hz), 7.40-7.70 (7H, m), 12.60-13.50 (1H, br). |
| 9-3 | (structure) | $^1$H-NMR (CDCl$_3$) δ ppm: 5.52 (2H, s), 6.63 (1H, s), 6.85-7.25 (3H, m), 7.30-7.50 (5H, m), 7.55-7.90 (2H, m), 8.00-8.15 (1H, m). |
| 9-4 | (structure) | $^1$H-NMR (CDCl$_3$) δ ppm: 1.32 (6H, d, J = 6.8 Hz), 2.95-3.10 (1H, m), 5.34 (2H, s), 5.80-5.90 (1H, m), 6.30 (1H, s), 7.05-7.20 (3H, m), 7.45-7.55 (1H, m). |

TABLE 14-continued

| Ex. No. | Strc | Physical data |
|---|---|---|
| 9-5 | (structure) | $^1$H-NMR (DMSO-$d_6$) δ ppm: 1.21 (6H, d, J = 6.8 Hz), 2.95-3.15 (1H, m), 5.55 (2H, s), 6.36 (1H, s), 7.02 (1H, dd, J = 2.0, 8.6 Hz), 7.10-7.20 (1H, m), 7.34 (1H, d, J = 8.6 Hz), 7.42 (1H, t, J = 7.7 Hz), 7.50-7.60 (2H, m), 7.75-7.85 (1H, m), 12.98 (1H, br s). |
| 9-6 | (structure) | $^1$H-NMR (DMSO-$d_6$) δ ppm: 5.55 (2H, s), 6.68 (1H, s), 7.00-7.20 (2H, m), 7.30-7.55 (8H, m), 7.65-7.70 (1H, m), 7.70-7.80 (1H, m), 12.96 (1H, br s). |

TABLE 15

| Ex. No. | Strc | Physical data |
|---|---|---|
| 9-7 | (structure) | $^1$H-NMR (DMSO-$d_6$) δ ppm: 5.57 (2H, s), 6.76 (1H, s), 7.05-7.20 (2H, m), 7.30-7.65 (9H, m), 7.70-7.85 (1H, m), 12.98 (1H, s). |
| 9-8 | (structure) | $^1$H-NMR (DMSO-$d_6$) δ ppm: 5.62 (2H, s), 6.87 (1H, s), 7.05-7.15 (1H, m), 7.37 (1H, t, J = 7.8 Hz), 7.40-7.55 (7H, m), 7.62 (1H, d, J = 8.8 Hz), 7.70-7.85 (1H, m), 8.04 (1H, s), 12.98 (1H, br s). |
| 9-9 | (structure) | $^1$H-NMR (DMSO-$d_6$) δ ppm: 5.54 (2H, s), 6.65-6.70 (1H, m), 6.90-7.05 (1H, m), 7.05-7.15 (1H, m), 7.30-7.60 (9H, m), 7.70-7.80 (1H, m), 12.97 (1H, br s). |
| 9-10 | (structure) | $^1$H-NMR (DMSO-$d_6$) δ ppm: 5.62 (2H, s), 6.80-6.90 (1H, m), 7.00-7.15 (1H, m), 7.37 (1H, t, J = 7.8 Hz), 7.40-7.55 (7H, m), 7.63 (1H, d, J = 8.5 Hz), 7.70-7.80 (1H, m), 8.15-8.20 (1H, m), 12.98 (1H, br s). |

TABLE 15-continued

| Ex. No. | Strc | Physical data |
|---|---|---|
| 9-11 | (5-Cl-indole, 2-sec-butyl, N-CH2-3-carboxyphenyl) | ¹H-NMR (DMSO-d₆) δ ppm: 0.77 (3H, t, J = 7.3 Hz), 1.17 (3H, d, J = 6.8 Hz), 1.40-1.75 (2H, m), 2.75-2.90 (1H, m), 5.54 (2H, s), 6.34 (1H, s), 7.02 (1H, dd, J = 2.0, 8.5 Hz), 7.10-7.20 (1H, m), 7.30-7.60 (4H, m), 7.75-7.85 (1H, m), 12.97 (1H, br s). |
| 9-12 | (5-Cl-indole, 2-isobutyl, N-CH2-3-carboxyphenyl) | ¹H-NMR (DMSO-d₆) δ ppm: 0.89 (6H, d, J = 6.5 Hz), 1.75-1.95 (1H, m), 2.57 (2H, d, J = 7.0 Hz), 5.51 (2H, s), 6.34 (1H, s), 7.02 (1H, dd, J = 2.0, 8.7 Hz), 7.10-7.20 (1H, m), 7.30-7.60 (4H, m), 7.75-7.85 (1H, m), 12.98 (1H, br). |

TABLE 16

| Ex. No. | Strc | Physical data |
|---|---|---|
| 9-13 | (5-Me-indole, 2-phenyl, N-CH2-3-carboxyphenyl) | ¹H-NMR (DMSO-d₆) δ ppm: 2.38 (3H, s), 5.50 (2H, s), 6.55-6.60 (1H, m), 6.90-7.00 (1H, m), 7.05-7.15 (1H, m), 7.24 (1H, d, J = 8.3 Hz), 7.30-7.55 (8H, m), 7.70-7.80 (1H, m), 12.91 (1H, br s). |
| 9-14 | (5-F-indole, 2-phenyl, N-CH2-furan-2-carboxylic acid) | ¹H-NMR (DMSO-d₆) δ ppm: 5.45 (2H, s), 6.21 (1H, d, J = 3.5 Hz), 6.62 (1H, s), 6.95-7.10 (2H, m), 7.36 (1H, dd, J = 2.5, 9.8 Hz), 7.40-7.65 (6H, m), 13.04 (1H, br s). |
| 9-15 | (5-OMe-indole, 2-isopropyl, N-CH2-3-carboxyphenyl) | ¹H-NMR (DMSO-d₆) δ ppm: 1.20 (6H, d, J = 6.8 Hz), 2.90-3.10 (1H, m), 3.73 (3H, s), 5.47 (2H, s), 6.26 (1H, s), 6.65 (1H, dd, J = 2.4, 8.8 Hz), 7.01 (1H, d, J = 2.4 Hz), 7.10-7.20 (2H, m), 7.40 (1H, t, J = 7.7 Hz), 7.50-7.60 (1H, m), 7.75-7.85 (1H, m), 12.93 (1H, br s). |

TABLE 16-continued

| Ex. No. | Strc | Physical data |
|---|---|---|
| 9-16 | (5-F-indole, 2-phenyl, N-CH2-pyridine-2-carboxylic acid) | ¹H-NMR (DMSO-d₆) δ ppm: 5.56 (2H, s), 6.69 (1H, s), 6.75-6.85 (1H, m), 6.90-7.05 (1H, m), 7.30-7.65 (7H, m), 7.80-7.95 (2H, m), 12.50-13.80 (1H, br). |
| 9-17 | (5-OEt-indole, 2-phenyl, N-CH2-3-carboxyphenyl) | ¹H-NMR (DMSO-d₆) δ ppm: 1.34 (3H, t, J = 7.0 Hz), 4.02 (2H, q, J = 7.0 Hz), 5.49 (2H, s), 6.58 (1H, s), 6.75 (1H, dd, J = 2.4, 9.0 Hz), 7.05-7.15 (2H, m), 7.24 (1H, d, J = 9.0 Hz), 7.30-7.55 (7H, m), 7.70-7.80 (1H, m), 12.94 (1H, s). |
| 9-18 | (5-OMe-indole, 2-phenyl, N-CH2-furan-2-carboxylic acid) | ¹H-NMR (DMSO-d₆) δ ppm: 3.77 (3H, s), 5.41 (2H, s), 6.18 (1H, d, J = 3.5 Hz), 6.54 (1H, s), 6.81 (1H, dd, J = 2.5, 9.0 Hz), 7.07 (1H, d, J = 3.5 Hz), 7.09 (1H, d, J = 2.5 Hz), 7.40-7.65 (6H, m), 13.04 (1H, br s). |

TABLE 17

| Ex. No. | Strc | Physical data |
|---|---|---|
| 9-19 | (5-OMe-indole, 2-sec-butyl, N-CH2-3-carboxyphenyl) | ¹H-NMR (DMSO-d₆) δ ppm: 0.78 (3H, t, J = 7.3 Hz), 1.17 (3H, d, J = 6.8 Hz), 1.40-1.75 (2H, m), 2.70-2.85 (1H, m), 3.74 (3H, s), 5.47 (2H, s), 6.24 (1H, s), 6.65 (1H, dd, J = 2.5, 8.8 Hz), 7.01 (1H, d, J = 2.5 Hz), 7.10-7.25 (2H, m), 7.40 (1H, t, J = 7.7 Hz), 7.50-7.55 (1H, m), 7.75-7.85 (1H, m), 12.97 (1H, br s). |
| 9-20 | (5-OMe-indole, 2-isobutyl, N-CH2-3-carboxyphenyl) | ¹H-NMR (DMSO-d₆) δ ppm: 0.89 (6H, d, J = 6.5 Hz), 1.70-1.95 (1H, m), 2.54 (2H, d, J = 7.0 Hz), 3.74 (3H, s), 5.44 (2H, s), 6.24 (1H, s), 6.64 (1H, dd, J = 2.4, 8.9 Hz), 7.01 (1H, d, J = 2.4 Hz), 7.10-7.25 (2H, m), 7.41 (1H, t, J = 7.7 Hz), 7.45-7.55 (1H, m), 7.75-7.85 (1H, m), 12.96 (1H, br s). |

TABLE 17-continued

| Ex. No. | Strc | Physical data |
|---|---|---|
| 9-21 | | ¹H-NMR (DMSO-d$_6$) δ ppm: 3.77 (3H, s), 5.53 (2H, s), 6.62 (1H, s), 6.65-6.80 (2H, m), 7.13 (1H, d, J = 2.3 Hz), 7.24 (1H, d, J = 9.0 Hz), 7.30-7.50 (3H, m), 7.50-7.65 (2H, m), 7.75-7.95 (2H, m), 12.85-13.65 (1H, br). |
| 9-22 | | ¹H-NMR (DMSO-d$_6$) δ ppm: 0.71 (6H, t, J = 7.4 Hz), 1.45-1.70 (4H, m), 2.55-2.70 (1H, m), 3.74 (3H, s), 5.47 (2H, s), 6.22 (1H, s), 6.66 (1H, dd, J = 2.3, 8.9 Hz), 7.01 (1H, d, J = 2.3 Hz), 7.15-7.30 (2H, m), 7.40 (1H, t, J = 7.7 Hz), 7.45-7.60 (1H, m), 7.70-7.85 (1H, m), 12.93 (1H, br s). |
| 9-23 | | ¹H-NMR (DMSO-d$_6$) δ ppm: 3.77 (3H, s), 5.45 (2H, s), 6.59 (1H, s), 6.77 (1H, dd, J = 2.4, 8.9 Hz), 7.00-7.60 (10H, m), 13.23 (1H, br s). |

TABLE 18

| Ex. No. | Strc | Physical data |
|---|---|---|
| 9-24 | | ¹H-NMR (DMSO-d$_6$) δ ppm: 3.77 (3H, s), 5.51 (2H, s), 6.62 (1H, s), 6.78 (1H, dd, J = 2.5, 8.8 Hz), 6.90-7.00 (1H, m), 7.13 (1H, d, J = 2.5 Hz), 7.25-7.35 (2H, m), 7.35-7.55 (6H, m), 13.29 (1H, br s). |
| 9-25 | | ¹H-NMR (DMSO-d$_6$) δ ppm: 3.76 (3H, s), 5.58 (2H, s), 6.66 (1H, s), 6.75 (1H, dd, J = 2.5, 9.0 Hz), 7.09 (1H, d, J = 2.5 Hz), 7.10-7.20 (1H, m), 7.20-7.35 (2H, m), 7.39 (1H, t, J = 7.8 Hz), 7.50-7.65 (2H, m), 7.66 (1H, dd, J = 3.0, 5.0 Hz), 7.70-7.80 (1H, m), 12.96 (1H, br s). |
| 9-26 | | ¹H-NMR (DMSO-d$_6$) δ ppm: 0.70 (6H, t, J = 7.3 Hz), 1.45-1.70 (4H, m), 2.60-2.75 (1H, m), 5.54 (2H, s), 6.32 (1H, s), 7.03 (1H, dd, J = 2.1, 8.7 Hz), 7.15-7.25 (1H, m), 7.35-7.60 (4H, m), 7.75-7.85 (1H, m), 12.95 (1H, br s). |

TABLE 18-continued

| Ex. No. | Strc | Physical data |
|---|---|---|
| 9-27 | | ¹H-NMR (DMSO-d$_6$) δ ppm: 3.78 (3H, s), 5.48 (2H, s), 6.25-6.40 (1H, m), 6.60-6.70 (1H, m), 6.77 (1H, dd, J = 2.5, 8.8 Hz), 7.10-7.30 (3H, m), 7.35-7.50 (5H, m), 7.50-7.60 (1H, m), 13.50 (1H, br s). |
| 9-28 | | ¹H-NMR (DMSO-d$_6$) δ ppm: 3.77 (3H, s), 5.57 (2H, s), 6.61 (1H, s), 6.79 (1H, dd, J = 2.4, 8.9 Hz), 7.12 (1H, d, J = 2.4 Hz), 7.35-7.55 (6H, m), 7.60-7.70 (1H, m), 8.25-7.35 (1H, m), 8.80-8.90 (1H, m), 13.42 (1H, s). |
| 9-29 | | ¹H-NMR (DMSO-d$_6$) δ ppm: 3.77 (3H, s), 5.61 (2H, s), 6.57 (1H, s), 6.75-6.85 (2H, m), 7.10 (1H, d, J = 2.5 Hz), 7.35-7.60 (7H, m), 12.80-13.20 (1H, br). |

TABLE 19

| Ex. No. | Strc | Physical data |
|---|---|---|
| 9-30 | | ¹H-NMR (DMSO-d$_6$) δ ppm: 1.22 (3H, t, J = 7.6 Hz), 2.67 (2H, q, J = 7.6 Hz), 5.50 (2H, s), 6.61 (1H, s), 6.95-7.05 (1H, m), 7.05-7.15 (1H, m), 7.26 (1H, d, J = 8.3 Hz), 7.30-7.55 (8H, m), 7.70-7.80 (1H, m), 12.95 (1H, br s). |
| 9-31 | | ¹H-NMR (DMSO-d$_6$) δ ppm: 3.77 (3H, s), 5.69 (2H, s), 6.55-6.70 (2H, m), 6.75-6.85 (2H, m), 7.11 (1H, d, J = 2.5 Hz), 7.15-7.25 (1H, m), 7.30-7.50 (2H, m), 7.50-7.60 (1H, m), 7.70-7.85 (2H, m), 12.96 (1H, br s). |
| 9-32 | | ¹H-NMR (DMSO-d$_6$) δ ppm: 3.76 (3H, s), 5.60 (2H, s), 6.67 (1H, s), 6.70-6.85 (2H, m), 7.08 (1H, d, J = 2.5 Hz), 7.10-7.20 (1H, m), 7.32 (1H, d, J = 9.0 Hz), 7.39 (1H, t, J = 7.7 Hz), 7.50-7.55 (1H, m), 7.70-7.80 (2H, m), 7.85-7.95 (1H, m), 12.96 (1H, br s). |

TABLE 19-continued

| Ex. No. | Strc | Physical data |
|---|---|---|
| 9-33 | 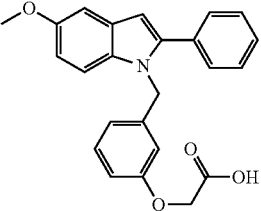 [SMILES: COc1ccc2c(c1)cc(-c1ccccc1)n2Cc1cccc(OCC(=O)O)c1] | ¹H-NMR (DMSO-d₆) δ ppm: 3.76 (3H, s), 4.54 (2H, s), 5.39 (2H, s), 6.40-6.55 (2H, m), 6.57 (1H, s), 6.55-6.80 (2H, m), 7.05-7.20 (2H, m), 7.24 (1H, d, J = 9.0 Hz), 7.35-7.55 (5H, m), 12.99 (1H, br s). |
| 9-34 | 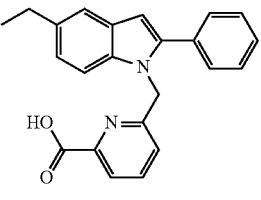 [SMILES: CCc1ccc2c(c1)cc(-c1ccccc1)n2Cc1cccc(C(=O)O)n1] | ¹H-NMR (DMSO-d₆) δ ppm: 1.22 (3H, t, J = 7.6 Hz), 2.67 (2H, q, J = 7.6 Hz), 5.52 (2H, s), 6.55-6.70 (2H, m), 6.90-7.05 (1H, m), 7.21 (1H, d, J = 8.3 Hz), 7.35-7.50 (4H, m), 7.50-7.60 (2H, m), 7.70-7.90 (2H, m), ESI-MS (m/z): 355 (M − H)⁻ |

TABLE 20

| Ex. No. | Strc | Physical data |
|---|---|---|
| 9-35 | 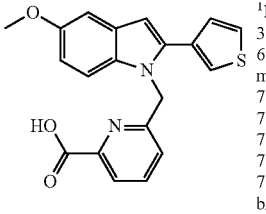 | ¹H-NMR (DMSO-d₆) δ ppm: 3.76 (3H, s), 5.59 (2H, s), 6.67 (1H, s), 6.70-6.85 (2H, m), 7.10 (1H, d, J = 2.5 Hz), 7.28 (1H, d, J = 8.8 Hz), 7.37 (1H, dd, J = 1.3, 5.0 Hz), 7.65 (1H, dd, J = 2.9, 5.0 Hz), 7.77 (1H, dd, J = 1.3, 2.9 Hz), 7.80-7.95 (2H, m), 13.24 (1H, br s). |
| 9-36 | 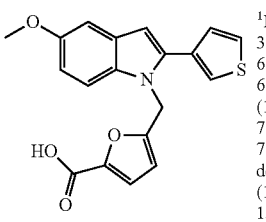 | ¹H-NMR (DMSO-d₆) δ ppm: 3.76 (3H, s), 5.48 (2H, s), 6.25 (1H, d, J = 3.3 Hz), 6.55-6.60 (1H, m), 6.79 (1H, dd, J = 2.5, 8.8 Hz), 7.00-7.15 (2H, m), 7.35-7.50 (2H, m), 7.72 (1H, dd, J = 2.9, 4.9 Hz), 7.76 (1H, dd, J = 1.4, 2.9 Hz), 13.03 (1H, br s). |
| 9-37 | 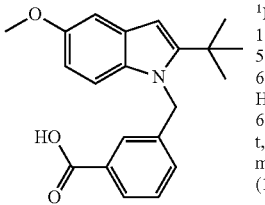 | ¹H-NMR (DMSO-d₆) δ ppm: 1.35 (9H, s), 3.72 (3H, s), 5.68 (2H, s), 6.28 (1H, s), 6.60 (1H, dd, J = 2.5, 8.8 Hz), 6.92 (1H, d, J = 8.8 Hz), 6.95-7.05 (2H, m), 7.37 (1H, t, J = 7.8 Hz), 7.45-7.55 (1H, m), 7.70-7.80 (1H, m), 12.90 (1H, br s). |
| 9-38 | 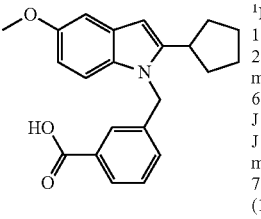 | ¹H-NMR (DMSO-d₆) δ ppm: 1.50-1.80 (6H, m), 1.85-2.00 (2H, m), 3.05-3.15 (1H, m), 3.73 (3H, s), 5.48 (2H, s), 6.27 (1H, s), 6.64 (1H, dd, J = 2.4, 8.7 Hz), 7.00 (1H, d, J = 2.4 Hz), 7.10-7.20 (2H, m), 7.40 (1H, t, J = 7.7 Hz), 7.50-7.60 (1H, m), 7.75-7.85 (1H, m), 12.95 (1H, br s). |

TABLE 20-continued

| Ex. No. | Strc | Physical data |
|---|---|---|
| 9-39 | 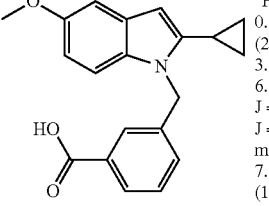 | ¹H-NMR (DMSO-d₆) δ ppm: 0.55-0.70 (2H, m), 0.80-0.95 (2H, m), 1.80-1.95 (1H, m), 3.72 (3H, s), 5.56 (2H, s), 6.08 (1H, s), 6.66 (1H, dd, J = 2.4, 8.8 Hz), 6.96 (1H, d, J = 2.4 Hz), 7.15-7.30 (2H, m), 7.42 (1H, t, J = 7.7 Hz), 7.55-7.65 (1H, m), 7.75-7.85 (1H, m), 12.94 (1H, br s). |

TABLE 21

| Ex. No. | Strc | Physical data |
|---|---|---|
| 9-40 | 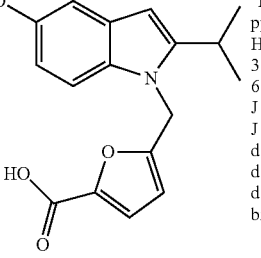 | ¹H-NMR (DMSO-d₆) δ ppm: 1.27 (6H, d, J = 6.8 Hz), 3.10-3.30 (1H, m), 3.72 (3H, s), 5.43 (2H, s), 6.20 (1H, s), 6.33 (1H, d, J = 3.4 Hz), 6.69 (1H, dd, J = 2.4, 8.9 Hz), 6.97 (1H, d, J = 2.4 Hz), 7.09 (1H, d, J = 3.4 Hz), 7.36 (1H, d, J = 8.9 Hz), 13.00 (1H, br s). |
| 9-41 | 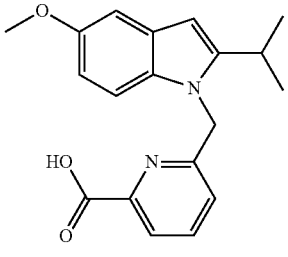 [SMILES: COc1ccc2c(c1)cc(C(C)C)n2Cc1cccc(C(=O)O)n1] | ¹H-NMR (DMSO-d₆) δ ppm: 1.22 (6H, d, J = 6.8 Hz), 3.00-3.20 (1H, m), 3.73 (3H, s), 5.52 (2H, s), 6.27 (1H, s), 6.55-6.75 (2H, m), 7.01 (1H, d, J = 2.5 Hz), 7.20 (1H, d, J = 8.8 Hz), 7.75-7.95 (2H, m), 13.23 (1H, br s). |
| 9-42 | 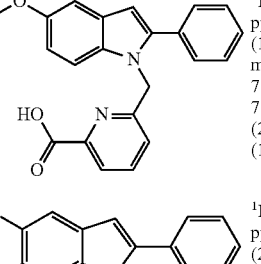 | ¹H-NMR (DMSO-d₆) δ ppm: 5.57 (2H, s), 6.72 (1H, s), 6.75-6.85 (1H, m), 6.90-7.35 (2H, m), 7.35-7.55 (5H, m), 7.55-7.65 (2H, m), 7.75-7.95 (2H, m), 12.80-13.65 (1H, br). |
| 9-43 | 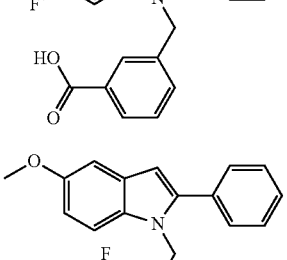 | ¹H-NMR (DMSO-d₆) δ ppm: 3.85 (3H, s), 5.49 (2H, s), 6.62 (1H, s), 7.00-7.10 (1H, m), 7.25-7.55 (9H, m), 7.70-7.80 (1H, m), 12.90 (1H, br s). |
| 9-44 | 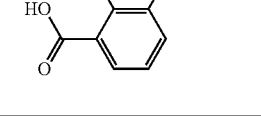 | ¹H-NMR (DMSO-d₆) δ ppm: 3.77 (3H, s), 5.50 (2H, s), 6.50-6.60 (1H, m), 6.60 (1H, s), 6.78 (1H, dd, J = 2.3, 8.9 Hz), 7.07 (1H, t, J = 7.8 Hz), 7.13 (1H, d, J = 2.3 Hz), 7.30 (1H, d, J = 8.9 Hz), 7.35-7.50 (5H, m), 7.60-7.75 (1H, m), 13.27 (1H, br s). |

TABLE 22

| Ex. No. | Strc | Physical data |
|---|---|---|
| 9-45 | | $^1$H-NMR (DMSO-$d_6$) δ ppm:<br>0.90 (6H, d, J = 6.5 Hz), 1.75-1.95 (1H, m), 2.59 (2H, d, J = 7.0 Hz), 3.74 (3H, s), 5.50 (2H, s), 6.25 (1H, s), 6.55-6.75 (2H, m), 7.02 (1H, d, J = 2.3 Hz), 7.21 (1H, d, J = 8.8 Hz), 7.75-7.95 (2H, m), 13.24 (1H, br s). |
| 9-46 | | $^1$H-NMR (DMSO-$d_6$) δ ppm:<br>5.55 (2H, s), 6.71 (1H, s), 6.90-7.60 (12H, m), 7.70-7.85 (1H, m), 12.94 (1H, br s). |
| 9-47 | | $^1$H-NMR (DMSO-$d_6$) δ ppm:<br>0.95 (6H, d, J = 6.5 Hz), 1.85-2.05 (1H, m), 2.66 (2H, d, J = 7.3 Hz), 3.73 (3H, s), 5.40 (2H, s), 6.18 (1H, s), 6.32 (1H, d, J = 3.3 Hz), 6.69 (1H, dd, J = 2.4, 8.9 Hz), 6.97 (1H, d, J = 2.4 Hz), 7.09 (1H, d, J = 3.3 Hz), 7.36 (1H, d, J = 8.9 Hz), 13.00 (1H, br s). |

Examples 10-1 to 10-12

The compounds shown in Tables 23 to 25 were synthesized in a manner similar to that of Example 1-1 by using the corresponding starting materials.

TABLE 23

| Ex. No. | Strc | Physical data |
|---|---|---|
| 10-1 | | $^1$H-NMR (CDCl$_3$) δ ppm:<br>2.45 (3H, s), 4.02 (3H, s), 5.59 (2H, s), 6.61 (1H, s), 6.70 (1H, d, J = 8.0 Hz), 6.90-7.10 (2H, m), 7.30-7.55 (6H, m), 7.80-7.70 (1H, m), 7.98 (1H, d, J = 7.5 Hz). |
| 10-2 | | $^1$H-NMR (CDCl$_3$) δ ppm:<br>3.86 (3H, s), 4.05 (3H, s), 5.62 (2H, s), 6.45-6.55 (1H, m), 6.62 (1H, s), 6.65-6.75 (1H, m), 6.82 (1H, dd, J = 2.3, 8.9 Hz), 7.06 (1H, d, J = 8.9 Hz), 7.12 (1H, d, J = 2.3 Hz), 7.40-7.55 (2H, m), 7.60-7.70 (1H, m), 7.95-8.05 (1H, m). |

TABLE 23-continued

| Ex. No. | Strc | Physical data |
| --- | --- | --- |
| 10-3 | | ¹H-NMR (CDCl₃) δ ppm: 0.85 (t, 3H, J = 7.4 Hz), 1.23 (3H, d, J = 6.8 Hz), 1.45-1.80 (2H, m), 2.60-2.80 (1H, m), 3.84 (3H, s), 4.05 (3H, s), 5.54 (2H, s), 6.32 (1H, s), 6.40-6.50 (1H, m), 6.75 (1H, dd, J = 2.3, 8.8 Hz), 7.00 (1H, d, J = 8.8 Hz), 7.08 (1H, d, J = 2.3 Hz), 7.61 (1H, t, J = 7.8 Hz), 7.95-8.05 (1H, m). |
| 10-4 | | ¹H-NMR (CDCl₃) δ ppm: 3.76 (3H, s), 3.86 (3H, s), 5.54 (2H, s), 6.67 (1H, s), 6.77 (1H, dd, J = 2.4, 8.8 Hz), 6.85-6.95 (1H, m), 7.13 (1H, d, J = 2.4 Hz), 7.15-7.35 (2H, m), 7.35-7.60 (3H, m), 7.80-7.95 (2H, m). |
| 10-5 | | ¹H-NMR (CDCl₃) δ ppm: 4.03 (3H, s), 5.64 (2H, s), 6.60-6.80 (2H, m), 7.21 (1H, d, J = 8.3 Hz), 7.30-7.50 (6H, m), 7.69 (1H, t, J = 7.8 Hz), 7.95-8.05 (2H, m). |

TABLE 24

| Ex. No. | Strc | Physical data |
| --- | --- | --- |
| 10-6 | | ¹H-NMR (CDCl₃) δ ppm: 4.02 (3H, s), 5.59 (2H, s), 6.60-6.70 (2H, m), 7.00 (1H, d, J = 8.7 Hz), 7.22 (1H, dd, J = 1.8, 8.7 Hz), 7.30-7.50 (5H, m), 7.60-7.75 (1H, m), 7.81 (1H, d, J = 1.8 Hz), 7.95-8.05 (1H, m). |
| 10-7 | | ¹H-NMR (CDCl₃) δ ppm: 2.52 (3H, s), 4.02 (3H, s), 5.59 (2H, s), 6.60-6.75 (2H, m), 7.06 (1H, d, J = 8.5 Hz), 7.16 (1H, dd, J = 1.8, 8.5 Hz), 7.30-7.45 (5H, m), 7.60-7.70 (2H, m), 7.95-8.05 (1H, m). |

TABLE 24-continued
| Ex. No. | Strc | Physical data |
|---|---|---|
| 10-8 | 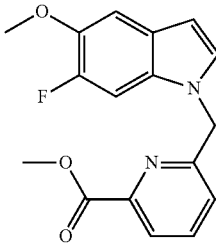 | ¹H-NMR (CDCl₃) δ ppm: 3.94 (3H, s), 4.03 (3H, s), 5.53 (2H, s), 6.55-6.75 (2H, m), 6.80-6.95 (1H, m), 7.20 (1H, d, J = 8.3 Hz), 7.30-7.45 (5H, m), 7.68 (1H, t, J = 7.8 Hz), 7.95-8.05 (1H, m). |
| 10-9 | 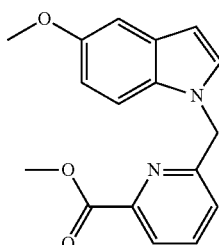 | ¹H-NMR (CDCl₃) δ ppm: 3.86 (3H, s), 4.05 (3H, s), 5.83 (2H, s), 6.75-6.90 (3H, m), 7.05-7.20 (2H, m), 7.60-7.70 (1H, m), 7.80-7.95 (2H, m), 7.95-8.05 (1H, m). |
| 10-10 | 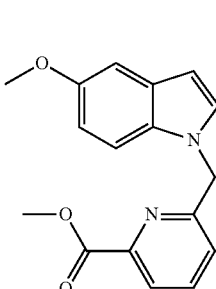 | ¹H-NMR (CDCl₃) δ ppm 3.86 (3H, s), 4.01 (3H, s), 5.47 (2H, s), 6.60-6.70 (2H, m), 6.82 (1H, dd, J = 2.4, 8.9 Hz), 7.01 (1H, d, J = 8.9 Hz), 7.05-7.20 (3H, m), 7.30-7.45 (2H, m), 7.55-7.70 (1H, m), 7.90-8.00 (1H, m). |
TABLE 25
| Ex. No. | Strc | Physical data |
|---|---|---|
| 10-11 | 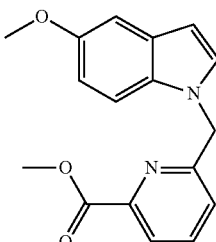 | ¹H-NMR (CDCl₃) δ ppm: 3.86 (3H, s), 4.03 (3H, s), 5.54 (2H, s), 6.50-6.75 (2H, m), 6.82 (1H, dd, J = 2.5, 8.8 Hz), 6.95-7.20 (4H, m), 7.30-7.45 (2H, m), 7.60-7.75 (1H, m), 7.90-8.10 (1H, m). |
| 10-12 | 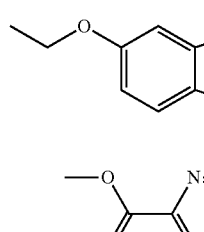 | ¹H-NMR (CDCl₃) δ ppm: 1.44 (3H, t, J = 7.0 Hz), 4.02 (3H, s), 4.09 (2H, q, J = 7.0 Hz), 5.58 (2H, s), 6.55-6.65 (1H, m), 6.65-6.75 (1H, m), 6.80 (1H, dd, J = 2.4, 8.9 Hz), 7.01 (1H, d, J = 8.9 Hz), 7.10-7.20 (1H, m), 7.30-7.45 (5H, m), 7.66 (1H, t, J = 7.8 Hz), 7.95-8.05 (1H, m). |

Examples 11-1 to 11-7

The compounds shown in Tables 26 to 27 were synthesized in a manner similar to that of Example 2-1 by using the corresponding starting materials.

TABLE 26

| Ex. No. | Strc | Physical data |
| --- | --- | --- |
| 11-1 | 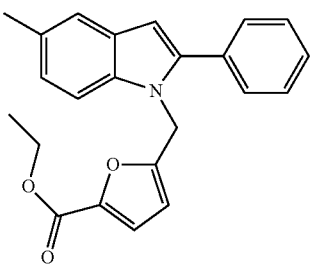 [SMILES: CCOC(=O)c1ccc(Cn2c(-c3ccccc3)cc3cc(C)ccc32)o1] | ¹H-NMR (CDCl₃) δ ppm:<br>1.37 (3H, t, J = 7.1 Hz), 2.46 (3H, s), 4.34 (2H, q, J = 7.1 Hz), 5.30 (2H, s), 5.97 (1H, d, J = 3.5 Hz), 6.54 (1H, s), 7.00-7.10 (2H, m), 7.18 (1H, d, J = 8.3 Hz), 7.35-7.55 (6H, m). |
| 11-2 | 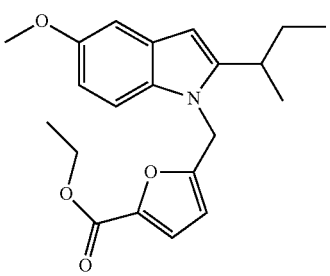 [SMILES: CCOC(=O)c1ccc(Cn2c(C(C)CC)cc3cc(OC)ccc32)o1] | ¹H-NMR (CDCl₃) δ ppm:<br>0.91 (3H, t, J = 7.4 Hz), 1.28 (3H, d, J = 6.8 Hz), 1.36 (3H, t, J = 7.1 Hz), 1.50-1.85 (2H, m), 2.75-2.90 (1H, m), 3.83 (3H, s), 4.35 (2H, q, J = 7.1 Hz), 5.30 (2H, s), 5.84 (1H, d, J = 3.5 Hz), 6.25 (1H, s), 6.78 (1H, dd, J = 2.4, 8.8 Hz), 7.00 (1H, d, J = 3.5 Hz), 7.04 (1H, d, J = 2.4 Hz), 7.11 (1H, d, J = 8.8 Hz). |
| 11-3 | 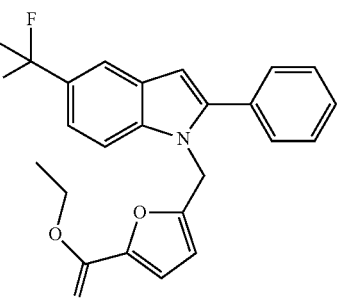 | ¹H-NMR (CDCl₃) δ ppm:<br>1.37 (3H, t, J = 7.1 Hz), 4.35 (2H, q, J = 7.1 Hz), 5.35 (2H, s), 5.99 (1H, d, J = 3.5 Hz), 6.69 (1H, s), 7.05 (1H, d, J = 3.5 Hz), 7.35-7.55 (7H, m), 7.94 (1H, s). |
| 11-4 | 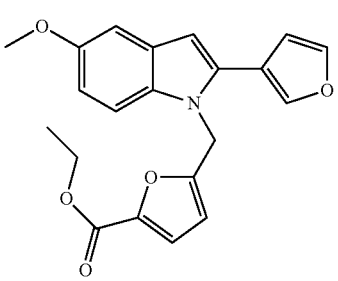 [SMILES: CCOC(=O)c1ccc(Cn2c(-c3ccoc3)cc3cc(OC)ccc32)o1] | ¹H-NMR (CDCl₃) δ ppm:<br>1.37 (3H, t, J = 7.1 Hz), 3.86 (3H, s), 4.36 (2H, q, J = 7.1 Hz), 5.34 (2H, s), 5.95-6.05 (1H, m), 6.50-6.65 (2H, m), 6.86 (1H, dd, J = 2.5, 8.9 Hz), 7.05 (1H, d, J = 3.5 Hz), 7.08 (1H, d, J = 2.5 Hz), 7.18 (1H, d, J = 8.9 Hz), 7.45-7.55 (1H, m), 7.55-7.65 (1H, m). |
| 11-5 | 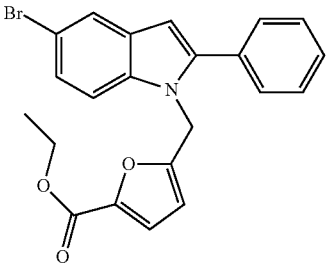 [SMILES: CCOC(=O)c1ccc(Cn2c(-c3ccccc3)cc3cc(Br)ccc32)o1] | ¹H-NMR (CDCl₃) δ ppm:<br>1.37 (3H, t, J = 7.1 Hz), 4.34 (2H, q, J = 7.1 Hz), 5.30 (2H, s), 5.97 (1H, d, J = 3.5 Hz), 6.50-6.60 (1H, m), 7.04 (1H, d, J = 3.5 Hz), 7.18 (1H, d, J = 8.7 Hz), 7.29 (1H, dd, J = 1.9, 8.7 Hz), 7.35-7.55 (5H, m), 7.75-7.80 (1H, m). |

TABLE 27

| Ex. No. | Strc | Physical data |
| --- | --- | --- |
| 11-6 | | $^1$H-NMR (CDCl$_3$) δ ppm:<br>1.37 (3H, t, J = 7.1 Hz), 3.94 (3H, s), 4.35 (2H, q, J = 7.1 Hz), 5.24 (2H, s), 5.95-6.05 (1H, m), 6.50-6.55 (1H, m), 7.00-7.10 (2H, m), 7.17 (1H, d, J = 8.3 Hz), 7.35-7.55 (5H, m). |
| 11-7 | | $^1$H-NMR (CDCl$_3$) δ ppm:<br>1.37 (3H, t, J = 7.2 Hz), 3.86 (3H, s), 4.34 (2H, q, J = 7.2 Hz), 5.25 (2H, s), 5.95-6.05 (1H, m), 6.45-6.55 (1H, m), 6.87 (1H, dd, J = 2.5, 9.0 Hz), 7.00-7.25 (5H, m), 7.40-7.50 (2H, m). |

Examples 12-1 to 12-2

The compounds shown in Table 28 were synthesized in a manner similar to that of Example 3-1 by using the corresponding starting materials.

TABLE 28

| Ex. No. | Strc | Physical data |
| --- | --- | --- |
| 12-1 | | $^1$H-NMR (CDCl$_3$) δ ppm:<br>3.88 (3H, s), 5.37 (2H, s), 6.59 (1H, s), 6.95-7.15 (2H, m), 7.22 (1H, dd, J = 1.9, 8.7 Hz), 7.25-7.50 (6H, m), 7.70-7.85 (2H, m), 7.85-8.00 (1H, m). |
| 12-2 | | $^1$H-NMR (CDCl$_3$) δ ppm:<br>2.52 (3H, s), 3.89 (3H, s), 5.37 (2H, s), 6.55-6.65 (1H, m), 7.00-7.15 (2H, m), 7.16 (1H, dd, J = 1.8, 8.5 Hz), 7.25-7.50 (6H, m), 7.60-7.70 (1H, m), 7.75-7.85 (1H, m), 7.85-7.95 (1H, m). |

Example 13
Methyl 2-fluoro-3-(2-furan-3-yl-5-methoxyindol-1-ylmethyl)benzoate

[Chem. 54]

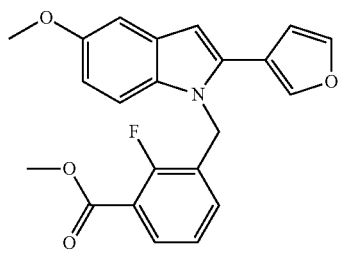

To a solution of 2-furan-3-yl-5-methoxyindole (200 mg) in N,N-dimethylformamide (4.7 mL) was added sodium hydride (dispersed in liquid paraffin, minimum 55%, 62 mg) under cooling with ice, and the mixture was stirred at room temperature for one hour. Then a solution of methyl 3-bromomethyl-2-fluorobenzoate (278 mg) in N,N-dimethylformamide (0.2 mL) was added, and the mixture was stirred at 80° C. for 15 hours. The reaction mixture was allowed to cool to ambient temperature. A saturated aqueous ammonium chloride solution-water (2/1) were added to the reaction mixture and this resulting mixture was extracted with ethyl acetate. The organic layer was washed successively with water and saturated saline, dried over anhydrous sodium sulfate and concentrated under reduced pressure. The residue was purified by aminopropylated silica gel column chromatography (eluting solvent: ethyl acetate-hexane) to obtain the title compound (72 mg).

$^1$H-NMR (CDCl$_3$) δ ppm:
3.86 (3H, s), 3.96 (3H, s), 5.45 (2H, s), 6.40-6.50 (1H, m), 6.55-6.75 (2H, m), 6.83 (1H, dd, J=2.4, 8.9 Hz), 6.95-7.15 (3H, m), 7.40-7.50 (2H, m), 7.75-7.85 (1H, m).

Example 14
Methyl 5-(5-methoxy-2-phenylindol-1-ylmethyl)thiophene-3-carboxylate

[Chem. 55]

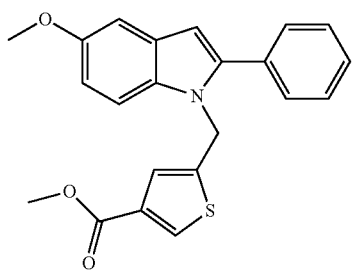

The title compound was synthesized in a manner similar to that of Example 5-1 by using the corresponding reactant.

$^1$H-NMR (CDCl$_3$) δ ppm:

3.81 (3H, s), 3.86 (3H, s), 5.35-5.45 (2H, m), 6.50-6.60 (1H, m), 6.86 (1H, dd, J=2.5, 8.8 Hz), 7.05-7.15 (1H, m), 7.15-7.25 (2H, m), 7.35-7.55 (5H, m), 7.91 (1H, d, J=1.5 Hz).

Example 15-1
Ethyl 2-(6-fluoro-5-methoxy-2-phenylindol-1-ylmethyl)thiazole-4-carboxylate To a solution of 6-fluoro-5-methoxy-2-phenylindole (200 mg) in N,N-dimethylformamide (4.1 mL) was added sodium hydride (dispersed in liquid paraffin, minimum 55%, 54 mg) under cooling with ice, and the mixture was stirred at room temperature for 70 minutes. Then a solution of ethyl 2-bromomethylthiazole-4-carboxylate (249 mg) in N,N-dimethylformamide (0.2 mL) was added, and the mixture was stirred at 80° C. for 25 hours. The reaction mixture was allowed to cool to ambient temperature. A saturated aqueous ammonium chloride solution-water (2/1) were added to the reaction mixture and this resulting mixture was extracted with ethyl acetate. The organic layer was washed successively with water and saturated saline, dried over anhydrous sodium sulfate and concentrated under reduced pressure. The residue was purified by silica gel column chromatography (eluting solvent: ethyl acetate-hexane) to obtain the title compound (125 mg).

In addition, structural formula and spectrum data of the title compound are shown in Table 29.

Examples 15-2 to 15-4

The compounds shown in Table 29 were synthesized in a manner similar to that of Example 15-1 by using the corresponding starting materials.

TABLE 29

| Ex. No. | Strc | Physical data |
|---|---|---|
| 15-1 | | $^1$H-NMR (CDCl$_3$) δ ppm: 1.41 (3H, t, J = 7.1 Hz), 3.94 (3H, s), 4.43 (2H, q, J = 7.1 Hz), 5.58 (2H, s), 6.60 (1H, s), 7.00 (1H, d, J = 11.3 Hz), 7.18 (1H, d, J = 8.3 Hz), 7.35-7.50 (5H, m), 8.03 (1H, s). |

TABLE 29-continued

| Ex. No. | Strc | Physical data |
|---|---|---|
| 15-2 | | ¹H-NMR (CDCl₃) δ ppm:<br>1.40 (3H, t, J = 7.1 Hz), 3.86 (3H, s), 4.42 (2H, q, J = 7.1 Hz), 5.62 (2H, s), 6.55-6.65 (1H, m), 6.85 (1H, dd, J = 2.5, 8.8 Hz), 7.10-7.20 (2H, m), 7.35-7.55 (5H, m), 8.02 (1H, s). |
| 15-3 | | ¹H-NMR (CDCl₃) δ ppm:<br>0.89 (3H, t, J = 7.4 Hz), 1.27 (3H, d, J = 6.8 Hz), 1.42 (3H, t, J = 7.1 Hz), 1.50-1.85 (2H, m), 2.70-2.85 (1H, m), 3.84 (3H, s), 4.45 (2H, q, J = 7.1 Hz), 5.60 (2H, s), 6.31 (1H, s), 6.79 (1H, dd, J = 2.4, 8.8 Hz), 7.06 (1H, d, J = 2.4 Hz), 7.10 (1H, d, J = 8.8 Hz), 8.01 (1H, s). |
| 15-4 | | ¹H-NMR (CDCl₃) δ ppm:<br>1.42 (3H, t, J = 7.1 Hz), 3.86 (3H, s), 4.45 (2H, q, J = 7.1 Hz), 5.66 (2H, s), 6.50-6.65 (2H, m), 6.86 (1H, dd, J = 2.4, 9.0 Hz), 7.05-7.15 (1H, m), 7.16 (1H, d, J = 9.0 Hz), 7.45-7.60 (2H, m), 8.04 (1H, s). |

Examples 16-1 to 16-27

The compounds shown in Tables 30 to 34 were synthesized in a manner similar to that of Example 9-1 by using the corresponding starting materials.

TABLE 30

| Ex. No. | Strc | Physical data |
|---|---|---|
| 16-1 | | ¹H-NMR (DMSO-d₆) δ ppm:<br>2.38 (3H, s), 5.41 (2H, s), 6.16 (1H, d, J = 3.5 Hz), 6.53 (1H, s), 6.95-7.05 (1H, m), 7.06 (1H, d, J = 3.5 Hz), 7.30-7.70 (7H, m), 13.01 (1H, br s). |
| 16-2 | | ¹H-NMR (DMSO-d₆) δ ppm:<br>2.38 (3H, s), 5.53 (2H, s), 6.61 (1H, s), 6.65-6.75 (1H, m), 6.90-7.00 (1H, m), 7.21 (1H, d, J = 8.5 Hz), 7.30-7.65 (6H, m), 7.75-7.95 (2H, m), 12.50-13.90 (1H, br). |

TABLE 30-continued

| Ex. No. | Strc | Physical data |
| --- | --- | --- |
| 16-3 | | ¹H-NMR (DMSO-d₆) δ ppm:<br>0.85 (3H, t, J = 7.4 Hz), 1.23 (3H, d,<br>J = 6.8 Hz), 1.45-1.80 (2H, m), 2.95-3.10<br>(1H, m), 3.73 (3H, s), 5.43 (2H, s), 6.18<br>(1H, s), 6.34 (1H, d, J = 3.5 Hz), 6.69 (1H,<br>dd, J = 2.3, 8.8 Hz), 6.97 (1H, d, J = 2.3 Hz),<br>7.09 (1H, d, J = 3.5 Hz), 7.37 (1H, d,<br>J = 8.8 Hz), 12.99 (1H, br s). |
| 16-4 | | ¹H-NMR (DMSO-d₆) δ ppm:<br>3.76 (3H, s), 5.60 (2H, s), 6.66 (1H, s),<br>6.70-6.90 (3H, m), 7.09 (1H, d, J = 2.5 Hz),<br>7.35 (1H, d, J = 9.0 Hz), 7.70-8.10 (4H, m),<br>12.50-14.00 (1H, br). |
| 16-5 | | ¹H-NMR (DMSO-d₆) δ ppm:<br>0.79 (3H, t, J = 7.4 Hz), 1.18 (3H, d,<br>J = 6.8 Hz), 1.40-1.75 (2H, m), 2.80-2.95<br>(1H, m), 3.73 (3H, s), 5.45-5.60 (2H, m),<br>6.25 (1H, s), 6.55-6.75 (2H, m), 7.01 (1H,<br>d, J = 2.5 Hz), 7.23 (1H, d, J = 9.0 Hz),<br>7.75-7.95 (2H, m), 12.50-14.00 (1H, br). |

TABLE 31

| Ex. No. | Strc | Physical data |
| --- | --- | --- |
| 16-6 | | ¹H-NMR (DMSO-d₆) δ ppm:<br>5.54 (2H, s), 6.22 (1H, d, J = 3.5 Hz), 6.80<br>(1H, s), 7.06 (1H, d, J = 3.5 Hz), 7.40-7.70<br>(6H, m), 7.79 (1H, d, J = 8.5 Hz), 8.01 (1H,<br>br s), 13.05 (1H, br s). |
| 16-7 | | ¹H-NMR (DMSO-d₆) δ ppm:<br>5.55 (2H, s), 6.68 (1H, s), 7.00-7.15 (1H,<br>m), 7.24 (1H, dd, J = 2.0, 8.8 Hz), 7.30-7.60<br>(8H, m), 7.70-7.90 (2H, m), 12.94 (1H, br<br>s). |

TABLE 31-continued

| Ex. No. | Strc | Physical data |
|---|---|---|
| 16-8 | | $^1$H-NMR (DMSO-d$_6$) δ ppm: 3.77 (3H, s), 5.53 (2H, s), 6.65-6.70 (1H, m), 6.77 (1H, dd, J = 2.4, 9.0 Hz), 6.80-6.90 (1H, m), 7.10-7.15 (1H, m), 7.20-7.30 (2H, m), 7.40-7.55 (3H, m), 7.80-7.90 (2H, m). ESI-MS (m/z): 377 (M + H)$^+$ |
| 16-9 | | $^1$H-NMR (DMSO-d$_6$) δ ppm: 5.63 (2H, s), 6.80-6.95 (2H, m), 7.35-7.70 (7H, m), 7.80-7.95 (2H, m), 8.00-8.10 (1H, m), 13.21 (1H, br s). |
| 16-10 | | $^1$H-NMR (DMSO-d$_6$) δ ppm: 3.76 (3H, s), 5.49 (2H, s), 6.32 (1H, d, J = 3.4 Hz), 6.58 (1H, s), 6.79 (1H, dd, J = 2.4, 9.0 Hz), 6.85-6.95 (1H, m), 7.05 (1H, d, J = 2.4 Hz), 7.09 (1H, d, J = 3.4 Hz), 7.47 (1H, d, J = 9.0 Hz), 7.80-7.90 (1H, m), 8.00-8.10 (1H, m), 13.04 (1H, s). |
| 16-11 | | $^1$H-NMR (DMSO-d$_6$) δ ppm: 5.57 (2H, s), 6.69 (1H, s), 6.75-6.85 (1H, m), 7.23 (H, dd, J = 1.9, 8.7 Hz), 7.30-7.65 (6H, m), 7.80-7.95 (3H, m), 13.21 (1H, br s). |

TABLE 32

| Ex. No. | Strc | Physical data |
|---|---|---|
| 16-12 | | $^1$H-NMR (DMSO-d$_6$) δ ppm: 5.47 (2H, s), 6.20 (1H, d, J = 3.4 Hz), 6.62 (1H, s), 7.06 (1H, d, J = 3.4 Hz), 7.30 (1H, dd, J = 1.9, 8.8 Hz), 7.40-7.70 (6H, m), 7.79 (1H, d, J = 1.9 Hz), 12.60-13.45 (1H, br). |

TABLE 32-continued

| Ex. No. | Strc | Physical data |
|---|---|---|
| 16-13 | | ¹H-NMR (DMSO-d₆) δ ppm:<br>2.48 (3H, s), 5.55 (2H, s), 6.60-6.70 (1H, m), 6.75-6.85 (1H, m), 7.09 (1H, dd, J = 1.8, 8.5 Hz), 7.31 (1H, d, J = 8.5 Hz), 7.35-7.65 (6H, m), 7.80-7.95 (2H, m).<br>ESI-MS (m/z): 375 (M + H)⁺ |
| 16-14 | | ¹H-NMR (DMSO-d₆) δ ppm:<br>2.48 (3H, s), 5.52 (2H, s), 6.60-6.70 (1H, m), 7.05-7.15 (2H, m), 7.25-7.65 (9H, m), 7.70-7.80 (1H, m), 12.93 (1H, br s). |
| 16-15 | | ¹H-NMR (DMSO-d₆) δ ppm:<br>3.85 (3H, s), 5.52 (2H, s), 6.60-6.80 (2H, m), 7.25-7.65 (7H, m), 7.75-7.95 (2H, m), 11.90-14.50 (1H, br). |
| 16-16 | | ¹H-NMR (DMSO-d₆) δ ppm:<br>3.85 (3H, s), 5.41 (2H, s), 6.18 (1H, d, J = 3.5 Hz), 6.50-6.60 (1H, m), 7.06 (1H, d, J = 3.5 Hz), 7.28 (1H, d, J = 8.5 Hz), 7.40-7.65 (6H, m), 13.02 (1H, br s). |
| 16-17 | | ¹H-NMR (DMSO-d₆) δ ppm:<br>3.78 (3H, s), 5.72 (2H, s), 6.60-6.70 (1H, m), 6.82 (1H, dd, J = 2.5, 9.0 Hz), 7.10-7.20 (1H, m), 7.35-7.65 (6H, m), 8.25 (1H, s), 12.00-14.00 (1H, br). |

TABLE 33

| Ex. No. | Strc | Physical data |
|---|---|---|
| 16-18 | | ¹H-NMR (DMSO-d₆) δ ppm: 3.77 (3H, s), 5.82 (2H, s), 6.65-6.75 (1H, m), 6.78 (1H, dd, J = 2.5, 8.8 Hz), 6.85 (1H, s), 7.13 (1H, d, J = 2.5 Hz), 7.35 (1H, d, J = 8.8 Hz), 7.75-7.95 (2H, m), 8.45-8.65 (2H, m), 12.00-14.40 (1H, br). |
| 16-19 | | ¹H-NMR (DMSO-d₆) δ ppm: 3.86 (3H, s), 5.73 (2H, s), 6.60-6.70 (1H, m), 7.32 (1H, d, J = 8.5 Hz), 7.35-7.60 (6H, m), 8.25 (1H, s), 13.01 (1H, br s). |
| 16-20 | | ¹H-NMR (DMSO-d₆) δ ppm: 3.77 (3H, s), 5.42 (2H, s), 6.55-6.70 (2H, m), 6.79 (1H, dd, J = 2.5, 8.8 Hz), 7.15 (1H, d, J = 2.5 Hz), 7.20-7.40 (3H, m), 7.40-7.60 (2H, m), 7.75-7.90 (2H, m), 12.60-13.80 (1H, br). |
| 16-21 | | ¹H-NMR (DMSO-d₆) δ ppm: 3.77 (3H, s), 5.59 (2H, s), 6.40-6.55 (1H, m), 6.60-6.80 (3H, m), 7.00-7.15 (2H, m), 7.32 (1H, d, J = 9.0 Hz), 7.65-7.80 (2H, m), 7.85-7.95 (1H, m), 13.32 (1H, br s). |
| 16-22 | | ¹H-NMR (DMSO-d₆) δ ppm: 3.77 (3H, s), 5.50 (2H, s), 6.60 (1H, s), 6.70-6.85 (2H, m), 7.12 (1H, d, J = 2.3 Hz), 7.20-7.35 (3H, m), 7.55-7.70 (2H, m), 7.75-795 (2H, m), 13.23 (1H, br s). |

TABLE 34

| Ex. No. | Strc | Physical data |
|---|---|---|
| 16-23 | | $^1$H-NMR (DMSO-d$_6$) δ ppm: 0.81 (3H, t, J = 7.3 Hz), 1.20 (3H, d, J = 6.8 Hz), 1.45-1.75 (2H, m), 2.85-3.00 (1H, m), 3.74 (3H, s), 5.72 (2H, s), 6.25 (1H, s), 6.71 (1H, dd, J = 2.4, 8.9 Hz), 7.01 (1H, d, J = 2.4 Hz), 7.33 (1H, d, J = 8.9 Hz), 8.28 (1H, s), 13.04 (1H, br s). |
| 16-24 | | $^1$H-NMR (DMSO-d$_6$) δ ppm: 3.77 (3H, s), 5.58 (2H, s), 6.56 (1H, s), 6.81 (1H, dd, J = 2.4, 8.8 Hz), 6.95-7.05 (1H, m), 7.09 (1H, d, J = 2.4 Hz), 7.40-7.60 (6H, m), 7.98 (1H, d, J = 1.5 Hz), 12.66 (2H, br s). |
| 16-25 | | $^1$H-NMR (DMSO-d$_6$) δ ppm: 3.76 (3H, s), 5.39 (2H, s), 6.20 (1H, d, J = 3.4 Hz), 6.53 (1H, s), 6.81 (1H, dd, J = 2.4, 9.0 Hz), 7.06 (1H, d, J = 3.4 Hz), 7.09 (1H, d, J = 2.4 Hz), 7.25-7.40 (2H, m), 7.45 (1H, d, J = 9.0 Hz), 7.55-7.70 (2H, m), 13.03 (1H, br s). |
| 16-26 | | $^1$H-NMR (DMSO-d$_6$) δ ppm: 3.77 (3H, s), 5.82 (2H, s), 6.68 (1H, s), 6.75-6.90 (2H, m), 7.08 (1H, d, J = 2.3 Hz), 7.48 (1H, d, J = 8.8 Hz), 7.75-7.85 (1H, m), 8.00-8.10 (1H, m), 8.27 (1H, s), 13.07 (1H, br s). |
| 16-27 | | $^1$H-NMR (DMSO-d$_6$) δ ppm: 1.34 (3H, t, J = 6.9 Hz), 4.02 (2H, q, J = 6.9 Hz), 5.52 (2H, s), 6.60 (1H, s), 6.65-6.80 (2H, m), 7.12 (1H, d, J = 2.5 Hz), 7.22 (1H, d, J = 8.8 Hz), 7.35-7.50 (3H, m), 7.50-7.65 (2H, m), 7.75-7.95 (2H, m), 12.00-14.40 (1H, br). |

Examples 17-1 to 17-23

The compounds shown in Tables 35 to 38 were synthesized in a manner similar to that of Example 1-1 by using the corresponding starting materials.

Examples 18-1 to 18-7

The compounds shown in Tables 39 to 40 were synthesized in a manner similar to that of Example 2-1 by using the corresponding starting materials.

Examples 19-1 to 19-8

The compounds shown in Tables 41 to 42 were synthesized in a manner similar to that of Example 3-1 by using the corresponding starting materials.

Example 20

Ethyl 4-(5-methoxy-2-phenylindol-1-ylmethyl)thiazole-2-carboxylate

[Chem. 56]

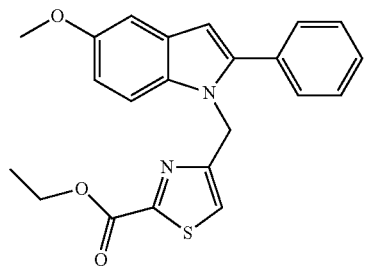 [SMILES: CCOC(=O)c1ccc(Cn2c(-c3ccccc3)cc3cc(OC)c(F)cc32)o1]

The title compound was synthesized in a manner similar to that of Example 5-1 by using the corresponding reactant.
$^1$H-NMR (CDCl$_3$) δ ppm:
1.44 (3H, t, J=7.1 Hz), 3.87 (3H, s), 4.49 (2H, q, J=7.1 Hz), 5.56 (2H, s), 6.60 (1H, s), 6.78 (1H, s), 6.84 (1H, d, J=2.4, 8.9 Hz), 7.08 (1H, d, J=8.9 Hz), 7.14 (1H, d, J=2.4 Hz), 7.30-7.50 (5H, m).

Example 21-1

Methyl 2-(5-methoxy-2-phenylindol-1-ylmethyl)oxazole-4-carboxylate

To a solution of 5-methoxy-2-phenylindole (205 mg) in N,N-dimethylformamide (4.6 mL) was added sodium hydride (in oil, 50 to 72%, 55 mg) under cooling with ice and an argon atmosphere, and the mixture was stirred at room temperature for 2 hours. Then methyl 2-(chloromethyl)-1,3-oxazole-4-carboxylate (193 mg) was added, and the mixture was stirred at 80° C. for 22 hours. The reaction mixture was allowed to cool to ambient temperature. A saturated aqueous ammonium chloride solution and water were added to the reaction mixture and this resulting mixture was extracted with ethyl acetate. The organic layer was washed successively with water and saturated saline, dried over anhydrous sodium sulfate and concentrated under reduced pressure. The residue was purified by silica gel column chromatography (eluting solvent: ethyl acetate-hexane) to obtain the title compound (229 mg).

In addition, structural formula and spectrum data of the title compound are shown in Table 42.
$^1$H-NMR (CDCl$_3$) δ ppm:
3.85 (3H, s), 3.92 (3H, s), 5.39 (2H, s), 6.55 (1H, s), 6.87 (1H, dd, J=2.5, 8.8 Hz), 7.10 (1H, d, J=2.5 Hz), 7.30 (1H, d, J=8.8 Hz), 7.35-7.65 (5H, m), 8.12 (1H, s).

Examples 21-2 to 21-3

The compounds shown in Table 42 were synthesized in a manner similar to that of Example 21-1 by using the corresponding starting materials.

Example 22

Methyl 6-[1-(5-methoxy-2-phenylindol-1-yl)ethyl]pyridine-2-carboxylate

[Chem. 57]

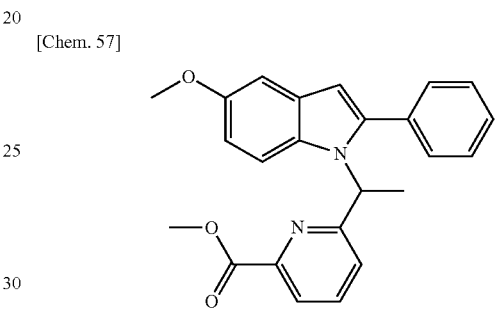

The title compound was synthesized in a manner similar to that of Example 5-1 by using the corresponding reactant.
$^1$H-NMR (CDCl$_3$) δ ppm:
2.06 (3H, d, J=7.1 Hz), 3.84 (3H, s), 4.01 (3H, s), 5.83 (1H, q, J=7.1 Hz), 6.54 (1H, s), 6.68 (1H, dd, J=2.5, 8.9 Hz), 6.86 (1H, d, J=8.9 Hz), 6.95-7.05 (1H, m), 7.05-7.20 (1H, m), 7.30-7.55 (5H, m), 7.65 (1H, t, J=7.8 Hz), 7.90-8.05 (1H, m).

Example 23

Methyl 6-(6-chloro-5-ethoxy-2-phenylindol-1-ylmethyl)pyridine-2-carboxylate

[Chem. 58]

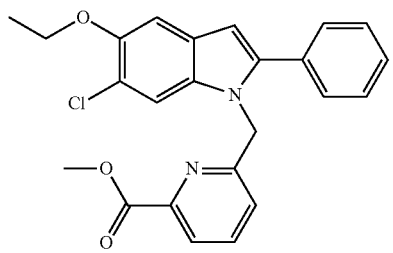

To a solution of methyl 6-(6-chloro-5-hydroxy-2-phenylindol-1-ylmethyl)pyridine-2-carboxylate (100 mg) in N,N-dimethylformamide (1 mL) were added, potassium carbonate (70.4 mg) and ethyl iodide (0.031 mL) and the mixture was stirred at room temperature for 22 hours. The reaction mixture was diluted with water and extracted with ethyl acetate. The organic layer was washed successively with water and saturated saline, dried over anhydrous sodium sulfate and concentrated under reduced pressure. The residue was purified by silica gel column chromatography (eluting solvent: ethyl acetate-hexane) to obtain the title compound (83.9 mg).

$^1$H-NMR (CDCl$_3$) δ ppm:
1.50 (3H, t, J=7.0 Hz), 4.03 (3H, s), 4.15 (2H, q, J=7.0 Hz), 5.53 (2H, s), 6.55-6.75 (2H, m), 7.15-7.25 (2H, m), 7.30-7.50 (5H, m), 7.65-7.75 (1H, m), 7.95-8.05 (1H, m).

Example 24

Methyl 6-(5-hydroxymethyl-2-phenylindol-1-ylmethyl)pyridine-2-carboxylate

[Chem. 59]

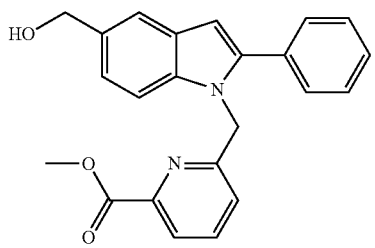

To a solution of methyl 6-(2-phenyl-5-triisopropylsilanyloxymethylindol-1-ylmethyl)pyridine-2-carboxylate (77.0 mg) in tetrahydrofuran (0.728 mL) was added tetrabutylammonium fluoride (1.0 mol/L tetrahydrofuran solution, 0.190 mL) under cooling with ice. The mixture was stirred under cooling with ice for one hour and then at room temperature for additional 2 hours. A saturated aqueous ammonium chloride solution was added to the reaction mixture and this resulting mixture was extracted with ethyl acetate. The organic layer was washed with saturated saline, dried over anhydrous sodium sulfate and concentrated under reduced pressure. The residue was purified by silica gel column chromatography (eluting solvent: ethyl acetate-hexane) to obtain the title compound (44.4 mg).

$^1$H-NMR (CDCl$_3$) δ ppm:
1.58 (1H, t, J=5.9 Hz), 4.03 (3H, s), 4.78 (2H, d, J=5.9 Hz), 5.62 (2H, s), 6.65-6.75 (2H, m), 7.12 (1H, d, J=8.4 Hz), 7.18 (1H, dd, J=1.6, 8.4 Hz), 7.30-7.45 (5H, m), 7.60-7.75 (2H, m), 7.95-8.05 (1H, m).

Examples 25-1 to 25-45

The compounds shown in Tables 43 to 48 were synthesized in a manner similar to that of Example 9-1 by using the corresponding starting materials.

TABLE 35

| Ex. No. | Strc | Physical Data |
|---|---|---|
| 17-1 | | $^1$H-NMR (CDCl$_3$) δ ppm:<br>3.87 (3H, s), 4.03 (3H, s), 5.57 (2H, s), 6.60-6.70 (2H, m), 6.83 (1H, dd, J = 2.5, 8.9 Hz), 7.04 (1H, d, J = 8.9 Hz), 7.10-7.20 (1H, m), 7.20-7.40 (3H, m), 7.40-7.50 (1H, m), 7.67 (1H, t, J = 7.8 Hz), 7.95-8.05 (1H, m). |
| 17-2 | | $^1$H-NMR (CDCl$_3$) δ ppm:<br>2.33 (3H, s), 3.86 (3H, s), 4.02 (3H, s), 5.59 (2H, s), 6.60 (1H, s), 6.66 (1H, d, J = 7.8 Hz), 6.80 (1H, d, J = 2.5, 8.8 Hz), 7.01 (1H, d, J = 8.8 Hz), 7.10-7.30 (5H, m), 7.60-7.70 (1H, m), 7.98 (1H, d, J = 7.5 Hz). |
| 17-3 | | $^1$H-NMR (CDCl$_3$) δ ppm:<br>3.87 (3H, s), 4.00 (3H, s), 5.42 (2H, s), 6.50-6.65 (2H, m), 6.83 (1H, dd, J = 2.5, 9.0 Hz), 7.05 (1H, d, J = 9.0 Hz), 7.17 (1H, d, J = 2.5 Hz), 7.20-7.40 (3H, m), 7.40-7.50 (1H, m), 7.60 (1H, t, J = 7.8 Hz), 7.85-8.00 (1H, m). |

TABLE 35-continued

| Ex. No. | Strc | Physical Data |
| --- | --- | --- |
| 17-4 | | $^1$H-NMR (CDCl$_3$) δ ppm:<br>2.21 (3H, s), 3.87 (3H, s), 4.00 (3H, s), 5.35 (2H, s), 6.45-6.60 (2H, m), 6.80 (1H, dd, J = 2.5, 8.8 Hz), 7.03 (1H, d, J = 8.8 Hz), 7.10-7.35 (5H, m), 7.61 (1H, t, J = 7.8 Hz), 7.90-8.00 (1H, m). |
| 17-5 | | $^1$H-NMR (CDCl$_3$) δ ppm:<br>3.87 (3H, s), 4.03 (3H, s), 5.55 (2H, s), 6.65-6.75 (2H, m), 6.85 (1H, dd, J = 2.4, 8.9 Hz), 7.06 (1H, d, J = 8.9 Hz), 7.10-7.20 (1H, m), 7.25-7.40 (1H, m), 7.60-7.80 (2H, m), 7.95-8.05 (1H, m), 8.59 (1H, dd, J = 1.6, 4.9 Hz), 8.65-8.75 (1H, m). |
| 17-6 | | $^1$H-NMR (CDCl$_3$) δ ppm:<br>3.96 (3H, s), 4.03 (3H, s), 5.54 (2H, s), 6.55-6.75 (2H, m), 7.15-7.25 (2H, m), 7.30-7.45 (5H, m), 7.69 (1H, t, J = 7.8 Hz), 7.95-8.05 (1H, m). |

TABLE 36

| Ex. No. | Strc | Physical Data |
| --- | --- | --- |
| 17-7 | | $^1$H-NMR (CDCl$_3$) δ ppm:<br>3.87 (3H, s), 4.04 (3H, s), 5.61 (2H, s), 6.65-6.85 (2H, m), 6.87 (1H, dd, J = 2.5, 9.0 Hz), 7.06 (1H, d, J = 9.0 Hz), 7.10-7.20 (1H, m), 7.25-7.40 (2H, m), 7.70 (1H, t, J = 7.8 Hz), 7.95-8.10 (1H, m), 8.55-8.65 (2H, m). |
| 17-8 | | $^1$H-NMR (CDCl$_3$) δ ppm:<br>2.25 (3H, s), 3.89 (3H, s), 4.03 (3H, s), 5.56 (2H, s), 6.55-6.65 (1H, m), 6.65-6.75 (1H, m), 6.89 (1H, s), 7.08 (1H, s), 7.25-7.45 (5H, m), 7.66 (1H, t, J = 7.8 Hz), 7.95-8.05 (1H, m). |

TABLE 36-continued

| Ex. No. | Strc | Physical Data |
| --- | --- | --- |
| 17-9 | | ¹H-NMR (CDCl₃) δ ppm:<br>3.95 (3H, s), 4.02 (3H, s), 5.43 (2H, s),<br>6.55-6.70 (2H, m), 7.05-7.25 (4H, m),<br>7.30-7.45 (2H, m), 7.65 (1H, t, J = 7.8 Hz),<br>7.95-8.05 (1H, m). |
| 17-10 | | ¹H-NMR (CDCl₃) δ ppm:<br>3.95 (3H, s), 4.03 (3H, s), 5.53 (2H, s),<br>6.55-6.75 (2H, m), 7.00-7.25 (5H, m),<br>7.25-7.45 (1H, m), 7.70 (1H, t, J = 7.8 Hz),<br>7.95-8.10 (1H, m). |
| 17-11 | | ¹H-NMR (CDCl₃) δ ppm:<br>3.95 (3H, s), 4.03 (3H, s), 5.49 (2H, s),<br>6.50-6.75 (2H, m), 7.00-7.15 (2H, m),<br>7.15-7.25 (2H, m), 7.30-7.45 (2H, m), 7.69<br>(1H, t, J = 7.8 Hz), 7.95-8.05 (1H, m). |
| 17-12 | | ¹H-NMR (CDCl₃) δ ppm:<br>2.29 (3H, s), 2.35 (3H, s), 4.03 (3H, s), 5.57<br>(2H, s), 6.50-6.75 (2H, m), 6.90 (1H, s),<br>7.25-7.50 (6H, m), 7.65 (1H, t, J = 7.8 Hz),<br>7.90-8.05 (1H, m). |

TABLE 37

| Ex. No. | Strc | Physical Data |
| --- | --- | --- |
| 17-13 | | ¹H-NMR (CDCl₃) δ ppm:<br>3.94 (3H, s), 4.02 (3H, s), 5.42 (2H, s),<br>6.55-6.70 (2H, m), 6.87 (1H, d, J = 11.3<br>Hz), 7.05-7.25 (3H, m), 7.30-7.45 (2H, m),<br>7.65 (1H, t, J = 7.8 Hz), 7.90-8.05 (1H, m). |

TABLE 37-continued
| Ex. No. | Strc | Physical Data |
| --- | --- | --- |
| 17-14 | 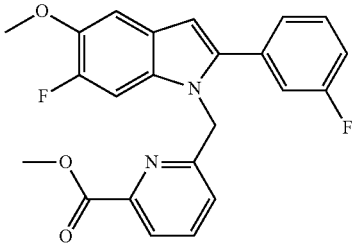 | ¹H-NMR (CDCl₃) δ ppm: 3.94 (3H, s), 4.03 (3H, s), 5.53 (2H, s), 6.55-6.75 (2H, m), 6.89 (1H, d, J = 11.3 Hz), 7.00-7.25 (4H, m), 7.25-7.45 (1H, m), 7.70 (1H, t, J = 7.8 Hz), 7.95-8.10 (1H, m). |
| 17-15 | 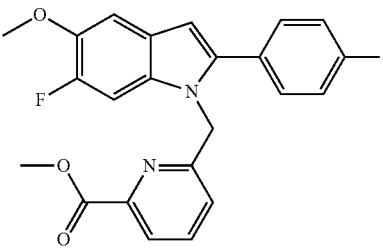 | ¹H-NMR (CDCl₃) δ ppm: 3.94 (3H, s), 4.03 (3H, s), 5.49 (2H, s), 6.50-6.75 (2H, m), 6.88 (1H, d, J = 11.3 Hz), 7.00-7.15 (2H, m), 7.19 (1H, d, J = 8.3 Hz), 7.30-7.45 (2H, m), 7.69 (1H, t, J = 7.8 Hz), 7.95-8.10 (1H, m). |
| 17-16 | 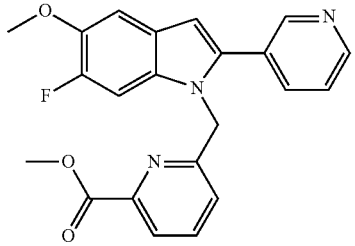 | ¹H-NMR (CDCl₃) δ ppm: 3.95 (3H, s), 4.03 (3H, s), 5.50 (2H, s), 6.60-6.80 (2H, s), 6.92 (1H, d, J = 11.3 Hz), 7.22 (1H, d, J = 8.0 Hz), 7.25-7.40 (1H, m), 7.65-7.80 (2H, m), 7.95-8.10 (1H, m), 8.55-8.65 (1H, m), 8.65-8.75 (1H, m). |
| 17-17 | 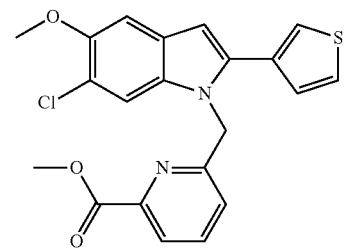 [SMILES: COC(=O)c1cccc(Cn2c(-c3ccsc3)cc3cc(OC)c(C)cc32)n1] | ¹H-NMR (CDCl₃) δ ppm: 3.95 (3H, s), 4.05 (3H, s), 5.59 (2H, s), 6.60-6.80 (2H, m), 7.10-7.35 (4H, m), 7.37 (1H, dd, J = 3.0, 5.0 Hz), 7.71 (1H, t, J = 7.8 Hz), 8.00-8.10 (1H, m). |
| 17-18 | 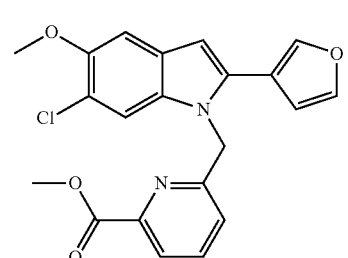 | ¹H-NMR (CDCl₃) δ ppm: 3.95 (3H, s), 4.06 (3H, s), 5.58 (2H, s), 6.45-6.55 (1H, m), 6.55-6.75 (2H, m), 7.16 (1H, s), 7.20-7.25 (1H, m), 7.40-7.55 (2H, m), 7.69 (1H, t, J = 7.8 Hz), 8.00-8.10 (1H, m). |

TABLE 38
| Ex. No. | Strc | Physical Data |
|---|---|---|
| 17-19 | 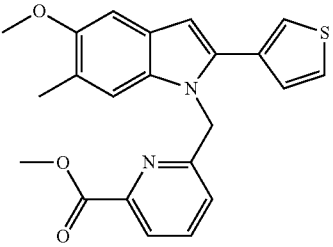 | ¹H-NMR (CDCl₃) δ ppm: 2.25 (3H, s), 3.89 (3H, s), 4.05 (3H, s), 5.61 (2H, s), 6.60-6.80 (2H, m), 6.90 (1H, br s), 7.06 (1H, s), 7.10-7.25 (2H, m), 7.30-7.40 (1H, m), 7.67 (1H, t, J = 7.8 Hz), 7.95-8.10 (1H, m). |
| 17-20 | 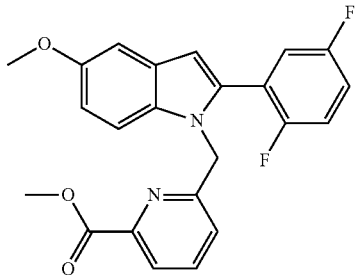 [SMILES: COC(=O)c1cccc(Cn2c(-c3cc(F)ccc3F)cc3cc(OC)ccc32)n1] | ¹H-NMR (CDCl₃) δ ppm: 3.86 (3H, s), 4.02 (3H, s), 5.47 (2H, s), 6.55-6.70 (2H, m), 6.80-6.90 (1H, m), 6.95-7.20 (5H, m), 7.64 (1H, t, J = 7.8 Hz), 7.97 (1H, d, J = 7.8 Hz). |
| 17-21 | 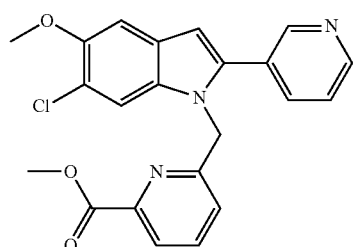 | ¹H-NMR (CDCl₃) δ ppm: 3.96 (3H, s), 4.03 (3H, s), 5.50 (2H, s), 6.60-6.80 (2H, m), 7.20 (1H, s), 7.23 (1H, s), 7.25-7.40 (1H, m), 7.65-7.80 (2H, m), 8.02 (1H, d, J = 7.8 Hz), 8.55-8.65 (1H, m), 8.65-8.75 (1H, m). |
| 17-22 | 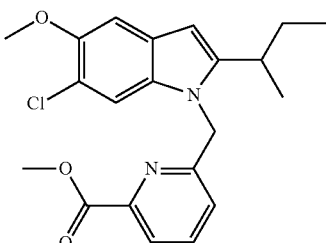 | ¹H-NMR (CDCl₃) δ ppm: 0.84 (3H, t, J = 7.4 Hz), 1.23 (3H, d, J = 6.9 Hz), 1.45-1.80 (2H, m), 2.60-2.75 (1H, m), 3.93 (3H, s), 4.06 (3H, s), 5.50 (2H, s), 6.31 (1H, s), 6.40-6.50 (1H, m), 7.12 (1H, s), 7.15 (1H, s), 7.64 (1H, t, J = 7.9 Hz), 7.95-8.05 (1H, m). |
| 17-23 | 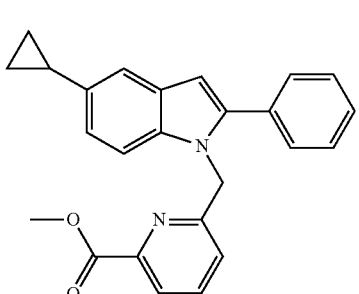 | ¹H-NMR (CDCl₃) δ ppm: 0.65-0.75 (2H, m), 0.85-1.00 (2H, m), 1.95-2.10 (1H, m), 4.02 (3H, s), 5.58 (2H, s), 6.55-6.65 (1H, m), 6.65-6.75 (1H, m), 6.91 (1H, dd, J = 1.9, 8.5 Hz), 7.01 (1H, d, J = 8.5 Hz), 7.30-7.45 (6H, m), 7.65 (1H, t, J = 7.9 Hz), 7.90-8.05 (1H, m). |

TABLE 39

| Ex. No. | Strc | Physical Data |
|---|---|---|
| 18-1 | | ¹H-NMR (CDCl₃) δ ppm:<br>1.35 (3H, t, J = 7.1 Hz), 3.86 (3H, s), 4.32 (2H, q, J = 7.1 Hz), 5.23 (2H, s), 5.87 (1H, d, J = 3.5 Hz), 6.57 (1H, s), 6.88 (1H, dd, J = 2.4, 8.9 Hz), 6.98 (1H, d, J = 3.5 Hz), 7.10-7.30 (4H, m), 7.35-7.50 (2H, m). |
| 18-2 | | ¹H-NMR (CDCl₃) δ ppm:<br>1.37 (3H, t, J = 7.1 Hz), 3.86 (3H, s), 4.35 (2H, q, J = 7.1 Hz), 5.29 (2H, s), 5.95-6.05 (1H, m), 6.50-6.60 (1H, m), 6.89 (1H, dd, J = 2.5, 8.8 Hz), 7.00-7.15 (3H, m), 7.15-7.30 (3H, m), 7.35-7.45 (1H, m). |
| 18-3 | | ¹H-NMR (CDCl₃) δ ppm:<br>1.37 (3H, t, J = 7.1 Hz), 3.87 (3H, s), 4.34 (2H, q, J = 7.1 Hz), 5.27 (2H, s), 6.00-6.05 (1H, m), 6.55-6.65 (1H, m), 6.91 (1H, dd, J = 2.4, 8.9 Hz), 7.04 (1H, d, J = 3.5 Hz), 7.10-7.15 (1H, m), 7.22 (1H, d, J = 8.9 Hz), 7.35-7.45 (1H, m), 7.75-7.85 (1H, m), 8.60-8.70 (1H, m), 8.70-8.80 (1H, m). |
| 18-4 | | ¹H-NMR (CDCl₃) δ ppm:<br>1.37 (3H, t, J = 7.1 Hz), 3.95 (3H, s), 4.35 (2H, q, J = 7.1 Hz), 5.25 (2H, s), 5.95-6.05 (1H, m), 6.50-6.60 (1H, m), 7.06 (1H, d, J = 3.5 Hz), 7.15 (1H, s), 7.30-7.55 (6H, m). |

TABLE 40

| Ex. No. | Strc | Physical Data |
|---|---|---|
| 18-5 | | ¹H-NMR (CDCl₃) δ ppm:<br>1.36 (3H, t, J = 7.2 Hz), 3.94 (3H, s), 4.33 (2H, q, J = 7.2 Hz), 5.17 (2H, s), 5.90 (1H, d, J = 3.5 Hz), 6.56 (1H, s), 6.95-7.35 (5H, m), 7.35-7.50 (2H, m). |

TABLE 40-continued

| Ex. No. | Strc | Physical Data |
| --- | --- | --- |
| 18-6 | | ¹H-NMR (CDCl₃) δ ppm:<br>1.37 (3H, t, J = 7.1 Hz), 2.32 (3H, s), 3.88 (3H, s), 4.35 (2H, q, J = 7.1 Hz), 5.27 (2H, s), 5.90-6.05 (1H, m), 6.50-6.55 (1H, m), 7.00-7.10 (3H, m), 7.30-7.55 (5H, m). |
| 18-7 | | ¹H-NMR (CDCl₃) δ ppm:<br>1.38 (3H, t, J = 7.2 Hz), 3.94 (3H, s), 4.36 (2H, q, J = 7.2 Hz), 5.30 (2H, s), 6.00-6.10 (1H, m), 6.50-6.65 (2H, m), 7.07 (1H, d, J = 3.3 Hz), 7.12 (1H, s), 7.30-7.35 (1H, m), 7.45-7.65 (2H, m). |

TABLE 41

| Ex. No. | Strc | Physical Data |
| --- | --- | --- |
| 19-1 | | ¹H-NMR (CDCl₃) δ ppm:<br>3.86 (3H, s), 3.89 (3H, s), 5.35 (2H, s), 6.55-6.65 (1H, m), 6.83 (1H, dd, J = 2.5, 8.8 Hz), 7.00-7.15 (3H, m), 7.20-7.40 (4H, m), 7.40-7.45 (1H, m), 7.75-7.85 (1H, m), 7.85-7.95 (1H, m). |
| 19-2 | | ¹H-NMR (CDCl₃) δ ppm:<br>3.80-3.90 (6H, m), 5.21 (2H, s), 6.50-6.60 (1H, m), 6.83 (1H, dd, J = 2.4, 8.9 Hz), 6.95-7.05 (1H, m), 7.05-7.40 (6H, m), 7.45-7.55 (1H, m), 7.60-7.70 (1H, m), 7.80-7.90 (1H, m). |
| 19-3 | | ¹H-NMR (CDCl₃) δ ppm:<br>3.69 (3H, s), 3.86 (3H, s), 3.89 (3H, s), 5.38 (2H, s), 6.55-6.65 (1H, m), 6.81 (1H, dd, J = 2.4, 8.9 Hz), 6.85-7.20 (6H, m), 7.20-7.40 (2H, m), 7.75-7.95 (2H, m). |

TABLE 41-continued
| Ex. No. | Strc | Physical Data |
|---|---|---|
| 19-4 | 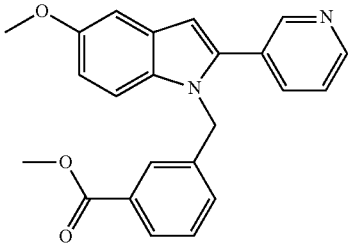 | ¹H-NMR (CDCl₃) δ ppm: 3.80-3.95 (6H, m), 5.36 (2H, s), 6.60-6.70 (1H, m), 6.85 (1H, dd, J = 2.5, 8.8 Hz), 7.00-7.20 (3H, m), 7.25-7.40 (2H, m), 7.60-7.75 (1H, m), 7.75-7.85 (1H, m), 7.85-7.95 (1H, m), 8.55-8.65 (1H, m), 8.65-8.75 (1H, m). |
| 19-5 | 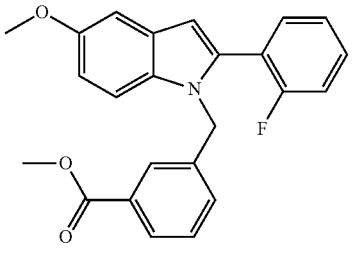 [SMILES: COC(=O)c1cccc(Cn2c(-c3ccccc3Cl)cc3cc(OC)ccc32)c1] | ¹H-NMR (CDCl₃) δ ppm: 3.80-3.90 (6H, m), 5.27 (2H, s), 6.60 (1H, s), 6.81 (1H, dd, J = 2.5, 8.8 Hz), 6.95-7.10 (2H, m), 7.10-7.30 (4H, m), 7.30-7.45 (2H, m), 7.70-7.90 (2H, m). |
| 19-6 | 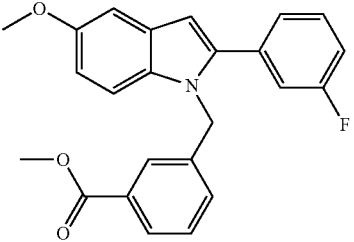 [SMILES: COC(=O)c1cccc(Cn2c(-c3cccc(F)c3)cc3cc(OC)ccc32)c1] | ¹H-NMR (CDCl₃) δ ppm: 3.80-3.95 (6H, m), 5.37 (2H, s), 6.55-6.65 (1H, m), 6.82 (1H, dd, J = 2.5, 8.8 Hz), 7.00-7.25 (6H, m), 7.25-7.40 (2H, m), 7.75-7.95 (2H, m). |
TABLE 42
| Ex. No. | Strc | Physical Data |
|---|---|---|
| 19-7 | 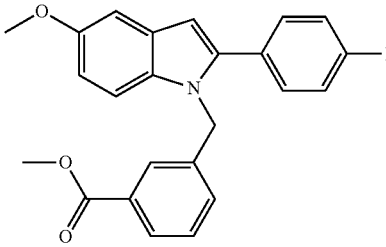 | ¹H-NMR (CDCl₃) δ ppm: 3.80-3.95 (6H, m), 5.32 (2H, s), 6.55 (1H, s), 6.81 (1H, dd, J = 2.5, 8.8 Hz), 7.00-7.15 (5H, m), 7.25-7.40 (3H, m), 7.75-7.95 (2H, m). |
| 19-8 | 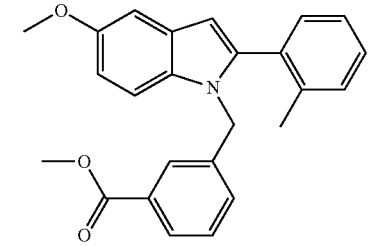 | ¹H-NMR (CDCl₃) δ ppm: 2.16 (3H, s), 3.86 (6H, s), 5.13 (2H, s), 6.40-6.50 (1H, m), 6.81 (1H, dd, J = 2.5, 8.8 Hz), 6.90-7.05 (1H, m), 7.05-7.40 (7H, m), 7.60-7.70 (1H, m), 7.75-7.90 (1H, m). |

TABLE 42-continued

| Ex. No. | Strc | Physical Data |
| --- | --- | --- |
| 21-1 | | ¹H-NMR (CDCl₃) δ ppm:<br>3.85 (3H, s), 3.92 (3H, s), 5.39 (2H, s), 6.55 (1H, s), 6.87 (1H, dd, J = 2.5, 8.8 Hz), 7.10 (1H, d, J = 2.5 Hz), 7.30 (1H, d, J = 8.8 Hz), 7.35-7.65 (5H, m), 8.12 (1H, s). |
| 21-2 | | ¹H-NMR (CDCl₃) δ ppm:<br>3.85-4.00 (6H, m), 5.34 (2H, s), 6.50-6.60 (1H, m), 7.10-7.20 (2H, m), 7.35-7.65 (5H, m), 8.14 (1H, s). |
| 21-3 | | ¹H-NMR (CDCl₃) δ ppm:<br>2.31 (3H, s), 3.87 (3H, s), 3.92 (3H, s), 5.37 (2H, s), 6.53 (1H, s), 7.03 (1H, s), 7.15 (1H, s), 7.35-7.65 (5H, m), 8.11 (1H, s). |

TABLE 43

| Ex. No. | Strc | Physical Data |
| --- | --- | --- |
| 25-1 | | ¹H-NMR (DMSO-d₆) δ ppm:<br>3.77 (3H, s), 5.51 (2H, s), 6.67 (1H, s), 6.78 (1H, dd, J = 2.5, 8.8 Hz), 6.80-6.90 (1H, m), 7.13 (1H, d, J = 2.5 Hz), 7.28 (1H, d, J = 8.8 Hz), 7.40-7.60 (3H, m), 7.65-7.75 (1H, m), 7.80-7.95 (2H, m), 13.00-13.50 (1H, br). |
| 25-2 | | ¹H-NMR (DMSO-d₆) δ ppm:<br>3.77 (3H, s), 5.51 (2H, s), 6.68 (1H, s), 6.79 (1H, dd, J = 2.4, 8.9 Hz), 7.05-7.15 (2H, m), 7.25-7.55 (7H, m), 7.70-7.80 (1H, m), 12.95 (1H, br s). |

TABLE 43-continued

| Ex. No. | Strc | Physical Data |
|---|---|---|
| 25-3 | | ¹H-NMR (DMSO-d₆) δ ppm: 2.31 (3H, s), 3.77 (3H, s), 5.51 (2H, s), 6.50-6.80 (3H, m), 7.05-7.45 (6H, m), 7.75-7.95 (2H, m), 12.85-13.65 (1H, br). |
| 25-4 | | ¹H-NMR (DMSO-d₆) δ ppm: 3.78 (3H, s), 5.34 (2H, s), 6.56 (1H, s), 6.60-6.70 (1H, m), 6.79 (1H, dd, J = 2.3, 8.9 Hz), 7.15 (1H, d, J = 2.3 Hz), 7.25-7.65 (5H, m), 7.70-7.90 (2H, m), 12.85-13.50 (1H, br). |
| 25-5 | | ¹H-NMR (DMSO-d₆) δ ppm: 3.77 (3H, s), 5.29 (2H, s), 6.50-6.55 (1H, m), 6.79 (1H, dd, J = 2.4, 8.9 Hz), 6.95-7.05 (1H, m), 7.10-7.15 (1H, m), 7.25-7.55 (6H, m), 7.55-7.65 (1H, m), 7.65-7.75 (1H, m), 12.60-13.20 (1H, br). |
| 25-6 | | ¹H-NMR (DMSO-d₆) δ ppm: 3.77 (3H, s), 5.32 (2H, s), 6.06 (1H, d, J = 3.5 Hz), 6.55 (1H, s), 6.84 (1H, dd, J = 2.5, 8.8 Hz), 7.01 (1H, d, J = 3.5 Hz), 7.05-7.15 (1H, m), 7.25-7.60 (5H, m), 12.99 (1H, br s). |
| 25-7 | | ¹H-NMR (DMSO-d₆) δ ppm: 2.17 (3H, s), 3.77 (3H, s), 5.28 (2H, s), 6.47 (1H, s), 6.55-6.65 (1H, m), 6.75 (1H, dd, J = 2.5, 8.8 Hz), 7.13 (1H, d, J = 2.5 Hz), 7.15-7.40 (5H, m), 7.70-7.90 (2H, m), 13.00-13.35 (1H, br). |
| 25-8 | | ¹H-NMR (DMSO-d₆) δ ppm: 3.77 (3H, s), 5.53 (2H, s), 6.72 (1H, s), 6.79 (1H, dd, J = 2.5, 8.9 Hz), 6.85-6.95 (1H, m), 7.15 (1H, d, J = 2.5 Hz), 7.32 (1H, d, J = 8.9 Hz), 7.40-7.50 (1H, m), 7.80-7.95 (2H, m), 8.00-8.15 (1H, m), 8.58 (1H, dd, J = 1.5, 4.8 Hz), 8.75-8.85 (1H, m), 13.24 (1H, br s). |

TABLE 44

| Ex. No. | Strc | Physical Data |
|---|---|---|
| 25-9 | | ¹H-NMR (DMSO-d₆) δ ppm: 3.87 (3H, s), 5.55 (2H, s), 6.60-6.80 (2H, m), 7.32 (1H, s), 7.35-7.50 (3H, m), 7.50-7.60 (3H, m), 7.75-7.95 (2H, m), 12.80-13.70 (1H, br). |
| 25-10 | | ¹H-NMR (DMSO-d₆) δ ppm: 3.69 (3H, s), 3.77 (3H, s), 5.50 (2H, s), 6.55-6.65 (1H, m), 6.76 (1H, dd, J = 2.5, 8.8), 6.90-7.20 (5H, m), 7.26 (1H, d, J = 8.8 Hz), 7.30-7.45 (2H, m), 7.45-7.55 (1H, m), 7.70-7.80 (1H, m), 12.96 (1H, br s). |
| 25-11 | | ¹H-NMR (DMSO-d₆) δ ppm: 3.77 (3H, s), 5.44 (2H, s), 6.23 (1H, d, J = 3.5 Hz), 6.61 (1H, s), 6.83 (1H, dd, J = 2.5, 8.8 Hz), 7.00-7.15 (2H, m), 7.20-7.35 (1H, m), 7.35-7.60 (4H, m), 13.04 (1H, br s). |
| 25-12 | | ¹H-NMR (DMSO-d₆) δ ppm: 3.76 (3H, s), 5.50 (2H, s), 6.57 (1H, s), 6.77 (1H, dd, J = 2.5, 8.8 Hz), 7.11 (1H, d, J = 2.5 Hz), 7.33 (1H, d, J = 8.8 Hz), 7.35-7.55 (4H, m), 7.55-7.70 (2H, m), 13.60-14.50 (1H, br). |
| 25-13 | | ¹H-NMR (DMSO-d₆) δ ppm: 3.78 (3H, s), 5.57 (2H, s), 6.75-6.90 (2H, m), 7.00-7.20 (2H, m), 7.30-7.50 (3H, m), 7.70-7.85 (2H, m), 8.15-8.30 (1H, m), 8.65-8.90 (2H, m). |
| 25-14 | | ¹H-NMR (DMSO-d₆) δ ppm: 3.77 (3H, s), 5.61 (2H, s), 6.75-6.90 (3H, m), 7.16 (1H, d, J = 2.5 Hz), 7.33 (1H, d, J = 9.0 Hz), 7.60-7.70 (2H, m), 7.80-7.95 (2H, m), 8.55-8.65 (2H, m), 13.25 (1H, br s). |

TABLE 44-continued
| Ex. No. | Strc | Physical Data |
|---|---|---|
| 25-15 | 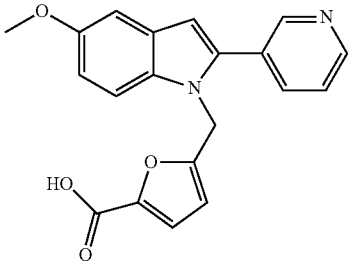 | $^1$H-NMR (DMSO-d$_6$) δ ppm: 3.77 (3H, s), 5.44 (2H, s), 6.24 (1H, d, J = 3.4 Hz), 6.65 (1H, s), 6.84 (1H, dd, J = 2.3, 8.9 Hz), 7.06 (1H, d, J = 3.4 Hz), 7.11 (1H, d, J = 2.3 Hz), 7.45-7.60 (2H, m), 7.95-8.05 (1H, m), 8.60-8.70 (1H, m), 8.75-8.85 (1H, m), 13.03 (1H, br s). |
| 25-16 | 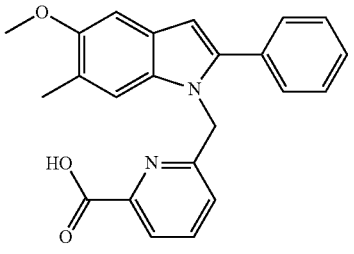 | $^1$H-NMR (DMSO-d$_6$) δ ppm: 2.18 (3H, s), 3.81 (3H, s), 5.51 (2H, s), 6.55-6.70 (2H, m), 7.10 (1H, s), 7.15 (1H, s), 7.30-7.60 (5H, m), 7.75-7.90 (2H, m), 12.95-13.50 (1H, br). |
TABLE 45
| Ex. No. | Strc | Physical Data |
|---|---|---|
| 25-17 | 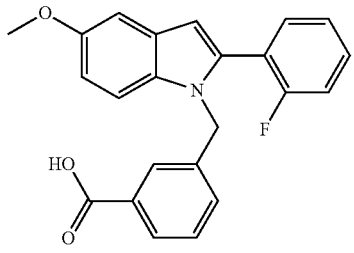 | $^1$H-NMR (DMSO-d$_6$) δ ppm: 3.77 (3H, s), 5.36 (2H, s), 6.59 (1H, s), 6.78 (1H, dd, J = 2.3, 8.9 Hz), 7.00-7.10 (1H, m), 7.13 (1H, d, J = 2.3 Hz), 7.20-7.55 (7H, m), 7.65-7.80 (1H, m), 12.91 (1H, br s). |
| 25-18 | 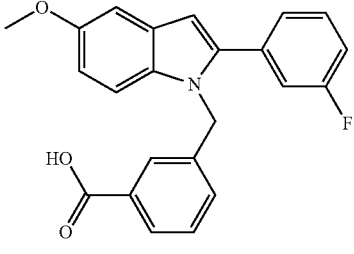 [SMILES: COc1ccc2c(c1)cc(-c1cccc(F)c1)n2Cc1cccc(C(=O)O)c1] | $^1$H-NMR (DMSO-d$_6$) δ ppm: 3.77 (3H, s), 5.52 (2H, s), 6.67 (1H, s), 6.79 (1H, dd, J = 2.4, 8.9 Hz), 7.05-7.15 (2H, m), 7.15-7.55 (7H, m), 7.70-7.80 (1H, m), 12.94 (1H, s). |
| 25-19 | 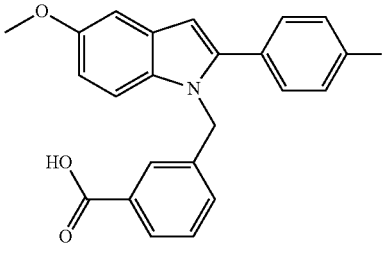 | $^1$H-NMR (DMSO-d$_6$) δ ppm: 3.77 (3H, s), 5.48 (2H, s), 6.55-6.65 (1H, m), 6.77 (1H, dd, J = 2.5, 8.8 Hz), 7.00-7.15 (2H, m), 7.20-7.60 (7H, m), 7.70-7.80 (1H, m), 12.94 (1H, br s). |

TABLE 45-continued
| Ex. No. | Strc | Physical Data |
|---|---|---|
| 25-20 | 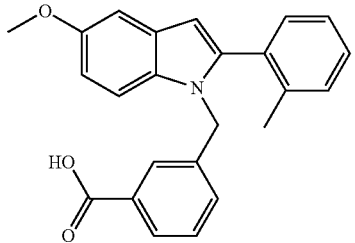 | ¹H-NMR (DMSO-d₆) δ ppm: 2.11 (3H, s), 3.77 (3H, s), 5.24 (2H, s), 6.40-6.50 (1H, m), 6.76 (1H, dd, J = 2.5, 8.8 Hz), 6.95-7.15 (2H, m), 7.20-7.40 (7H, m), 7.65-7.80 (1H, m), 12.90 (1H, s). |
| 25-21 | 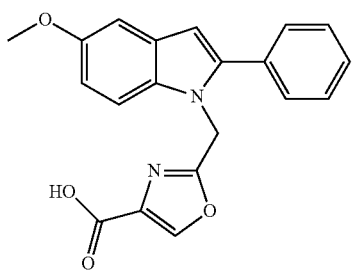 [SMILES: COc1ccc2c(c1)cc(-c1ccccc1)n2Cc1nc(C(=O)O)co1] | ¹H-NMR (DMSO-d₆) δ ppm: 3.77 (3H, s), 5.52 (2H, s), 6.50-6.60 (1H, m), 6.83 (1H, dd, J = 2.5, 8.8 Hz), 7.05-7.15 (1H, m), 7.30-7.65 (6H, m), 8.66 (1H, s), 12.50-13.55 (1H, br). |
| 25-22 | 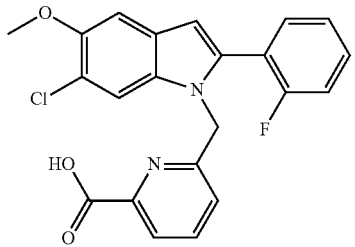 [SMILES: COc1cc2cc(-c3ccccc3F)n(Cc3cccc(C(=O)O)n3)c2cc1Cl] | ¹H-NMR (DMSO-d₆) δ ppm: 3.87 (3H, s), 5.44 (2H, s), 6.60-6.75 (2H, m), 7.20-7.70 (6H, m), 7.75-7.90 (2H, m), 12.50-14.00 (1H, br). |
| 25-23 | 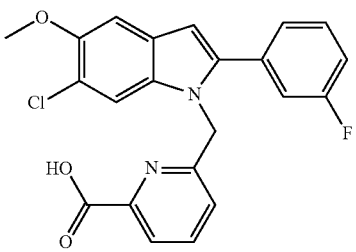 [SMILES: COc1cc2cc(-c3cccc(F)c3)n(Cc3cccc(C(=O)O)n3)c2cc1Cl] | ¹H-NMR (DMSO-d₆) δ ppm: 3.86 (3H, s), 5.55 (2H, s), 6.65-6.75 (1H, m), 6.80-6.95 (1H, m), 7.15-7.30 (1H, m), 7.32 (1H, s), 7.35-7.65 (4H, m), 7.80-7.95 (2H, m), 12.50-14.00 (1H, br). |
| 25-24 | 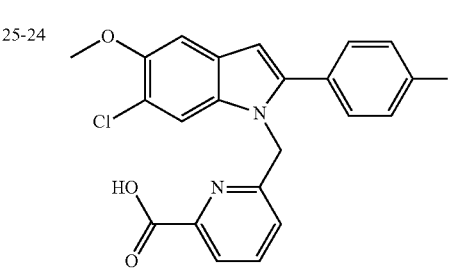 | ¹H-NMR (DMSO-d₆) δ ppm: 3.86 (3H, s), 5.52 (2H, s), 6.60-6.70 (1H, m), 6.75-6.90 (1H, m), 7.20-7.40 (3H, m), 7.50-7.70 (3H, m), 7.80-7.95 (2H, m), 13.20 (1H, br s). |

TABLE 46

| Ex. No. | Strc | Physical Data |
| --- | --- | --- |
| 25-25 | | ¹H-NMR (DMSO-d₆) δ ppm:<br>1.93 (3H, d, J = 7.0 Hz), 3.73 (3H, s), 5.72 (1H, q, J = 7.0 Hz), 6.45-6.70 (2H, m), 6.90 (1H, d, J = 9.0 Hz), 7.05-7.20 (2H, m), 7.35-7.70 (5H, m), 7.80-8.00 (2H, m).<br>ESI-MS (m/z): 373 (M + H)⁺ |
| 25-26 | | ¹H-NMR (DMSO-d₆) δ ppm:<br>3.86 (3H, s), 5.44 (2H, s), 6.16 (1H, d, J = 3.3 Hz), 6.55-6.65 (1H, m), 7.05 (1H, d, J = 3.3 Hz), 7.28 (1H, s), 7.40-7.65 (5H, m), 7.72 (1H, s), 12.50-13.50 (1H, br). |
| 25-27 | | ¹H-NMR (DMSO-d₆) δ ppm:<br>2.25 (3H, s), 2.28 (3H, s), 5.51 (2H, s), 6.55-6.70 (2H, m), 7.13 (1H, s), 7.30-7.60 (6H, m), 7.75-7.95 (2H, m), 12.50-14.00 (1H, br). |
| 25-28 | | ¹H-NMR (DMSO-d₆) δ ppm:<br>3.86 (3H, s), 5.41 (2H, s), 6.50-6.70 (2H, m), 7.15-7.60 (6H, m), 7.70-7.90 (2H, m).<br>ESI-MS (m/z): 395 (M + H)⁺ |
| 25-29 | | ¹H-NMR (DMSO-d₆) δ ppm:<br>3.85 (3H, s), 5.53 (2H, s), 6.65-6.75 (1H, m), 6.75-6.90 (1H, m), 7.15-7.60 (6H, m), 7.75-7.95 (2H, m).<br>ESI-MS (m/z): 395 (M + H)⁺ |
| 25-30 | | ¹H-NMR (DMSO-d₆) δ ppm:<br>3.85 (3H, s), 5.32 (2H, s), 6.07 (1H, d, J = 3.5 Hz), 6.58 (1H, s), 7.01 (1H, d, J = 3.5 Hz), 7.25-7.45 (3H, m), 7.45-7.65 (3H, m), 13.02 (1H, br s). |

TABLE 46-continued

| Ex. No. | Strc | Physical Data |
|---|---|---|
| 25-31 | 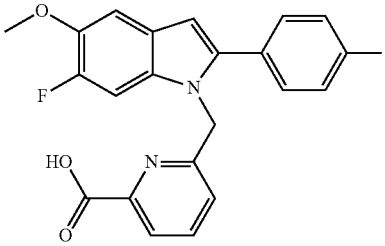 | $^1$H-NMR (DMSO-$d_6$) δ ppm:<br>3.85 (3H, s), 5.49 (2H, s), 6.55-6.80 (2H, m),<br>7.20-7.45 (4H, m), 7.55-7.70 (2H, m),<br>7.70-7.95 (2H, m).<br>ESI-MS (m/z): 395 (M + H)$^+$ |
| 25-32 | 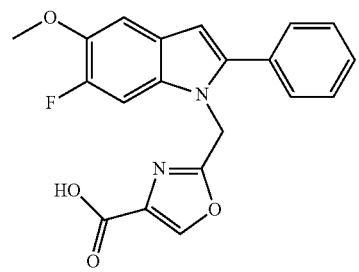 | $^1$H-NMR (DMSO-$d_6$) δ ppm:<br>3.85 (3H, s), 5.52 (2H, s), 6.58 (1H, s), 7.30 (1H, d, J = 8.5 Hz), 7.35-7.60 (6H, m), 8.62 (1H, s).<br>ESI-MS (m/z): 367 (M + H)$^+$ |

TABLE 47

| Ex. No. | Strc | Physical Data |
|---|---|---|
| 25-33 | 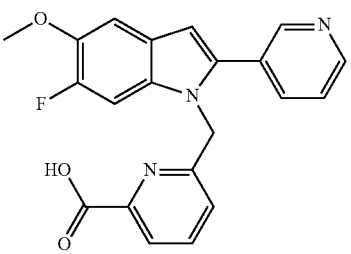 | $^1$H-NMR (DMSO-$d_6$) δ ppm:<br>3.86 (3H, s), 5.55 (2H, s), 6.82 (1H, s), 7.05-7.20 (1H, m), 7.35 (1H, d, J = 8.5 Hz), 7.49 (1H, d, J = 12.0 Hz), 7.65-8.00 (3H, m), 8.40-8.55 (1H, m), 8.65-8.80 (1H, m), 9.00-9.15 (1H, m).<br>ESI-MS (m/z): 378 (M + H)$^+$ |
| 25-34 | 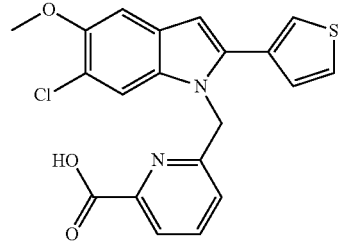 [SMILES: COc1cc2cc(-c3ccsc3)n(Cc3cccc(C(=O)O)n3)c2cc1Cl] | $^1$H-NMR (DMSO-$d_6$) δ ppm:<br>3.86 (3H, s), 5.60 (2H, s), 6.42 (1H, d, J = 7.8 Hz), 6.70-6.80 (1H, m), 7.25-7.50 (3H, m), 7.60-7.90 (4H, m).<br>ESI-MS (m/z): 399, 401 (M + H)$^+$ |
| 25-35 | 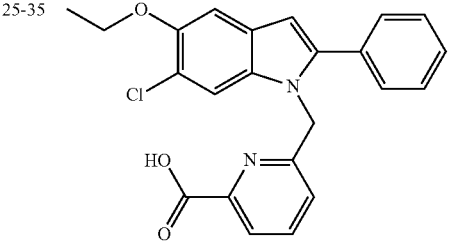 | $^1$H-NMR (DMSO-$d_6$) δ ppm:<br>1.38 (3H, t, J = 6.9 Hz), 4.11 (2H, q, J = 6.9 Hz), 5.52 (2H, s), 6.45-6.60 (1H, m), 6.60-6.70 (1H, m), 7.32 (1H, s), 7.35-7.60 (6H, m), 7.65-7.85 (2H, m). |

TABLE 47-continued

| Ex. No. | Strc | Physical Data |
| --- | --- | --- |
| 25-36 | | $^1$H-NMR (DMSO-d$_6$) δ ppm:<br>2.24 (3H, s), 3.80 (3H, s), 5.38 (2H, s), 6.13 (1H, d, J = 3.5 Hz), 6.45-6.55 (1H, m), 7.00-7.15 (2H, m), 7.33 (1H, s), 7.35-7.65 (5H, m), 12.50-13.50 (1H, br). |
| 25-37 | | $^1$H-NMR (DMSO-d$_6$) δ ppm:<br>3.86 (3H, s), 5.63 (2H, s), 6.65-6.90 (3H, m), 7.27 (1H, s), 7.60-8.10 (5H, m).<br>ESI-MS (m/z): 383, 385 (M + H)$^+$ |
| 25-38 | | $^1$H-NMR (DMSO-d$_6$) δ ppm:<br>3.84 (3H, s), 5.53 (2H, s), 6.32 (1H, d, J = 3.5 Hz), 6.60-6.70 (1H, m), 6.85-6.95 (1H, m), 7.09 (1H, d, J = 3.5 Hz), 7.24 (1H, s), 7.70-7.90 (2H, m), 8.05-8.15 (1H, m), 13.07 (1H, br s). |
| 25-39 | | $^1$H-NMR (DMSO-d$_6$) δ ppm:<br>2.19 (3H, s), 3.81 (3H, s), 5.56 (2H, s), 6.55-6.75 (2H, m), 7.07 (1H, s), 7.15 (1H, s), 7.25-7.40 (1H, m), 7.55-7.90 (4H, m).<br>ESI-MS (m/z): 379 (M + H)$^+$ |
| 25-40 | | $^1$H-NMR (DMSO-d$_6$) δ ppm:<br>2.24 (3H, s), 3.80 (3H, s), 5.45 (2H, s), 6.52 (1H, s), 7.07 (1H, s), 7.25 (1H, s), 7.35-7.70 (5H, m), 8.42 (1H, s).<br>ESI-MS (m/z): 363 (M + H)$^+$ |

TABLE 48

| Ex. No. | Strc | Physical Data |
|---|---|---|
| 25-41 | | ¹H-NMR (DMSO-d$_6$) δ ppm: 3.77 (3H, s), 5.43 (2H, s), 6.66 (1H, s), 6.75-6.90 (2H, m), 7.14 (1H, d, J = 2.5 Hz), 7.25-7.70 (4H, m), 7.75-7.95 (2H, m). ESI-MS (m/z): 395 (M + M)⁺ |
| 25-42 | | ¹H-NMR (DMSO-d$_6$) δ ppm: 3.87 (3H, s), 5.55 (2H, s), 6.75 (1H, s), 6.85-7.00 (1H, m), 7.33 (1H, s), 7.35-7.55 (1H, m), 7.63 (1H, s), 7.80-7.95 (2H, m), 8.00-8.15 (1H, m), 8.50-8.65 (1H, m), 8.70-8.85 (1H, m), 12.80-13.60 (1H, br). |
| 25-43 | | ¹H-NMR (DMSO-d$_6$) δ ppm: 4.55 (2H, d, J = 4.7 Hz), 4.95-5.15 (1H, m), 5.56 (2H, s), 6.65-6.75 (2H, m), 7.05-7.15 (1H, m), 7.28 (1H, d, J = 8.2 Hz), 7.35-7.50 (3H, m), 7.50-7.65 (3H, m), 7.75-7.95 (2H, m), 13.23 (1H, br s). |
| 25-44 | | ¹H-NMR (DMSO-d$_6$) δ ppm: 0.77 (3H, t, J = 7.4 Hz), 1.17 (3H, d, J = 6.9 Hz), 1.40-1.70 (2H, m), 2.80-2.95 (1H, m), 3.83 (3H, s), 5.45-5.65 (2H, m), 6.30 (1H, s), 6.70 (1H, d, J = 7.3 Hz), 7.20 (1H, s), 7.55 (1H, s), 7.80-7.95 (2H, m), 13.00-13.50 (1H, br). |
| 25-45 | | ¹H-NMR (DMSO-d$_6$) δ ppm: 0.55-0.70 (2H, m), 0.85-0.95 (2H, m), 1.90-2.05 (1H, m), 5.52 (2H, s), 6.60 (1H, s), 6.72 (1H, d, J = 7.6 Hz), 6.86 (1H, dd, J = 1.6, 8.5 Hz), 7.20 (1H, d, J = 8.5 Hz), 7.25-7.65 (6H, m), 7.75-7.90 (2H, m), 12.00-14.50 (1H, br). |

Test Example 1

Test for Confirmation of EP$_1$ Receptor Antagonism (1) Preparation of Rat EP$_1$ Expression Vector Using Rat Kidney BD Marathon-Ready cDNA (Nippon Becton Dickinson Company, Ltd.) as a template, a forward primer shown in SEQ ID NO. 1, and a reverse primer shown in SEQ ID NO. 2, a first run of PCR was carried out using KOD-Plus-Ver 2.0 (Toyobo Co., Ltd.). Further, using this amplification product as a template, a forward primer shown in SEQ ID NO. 3, and a reverse primer shown in SEQ ID NO. 4, a second run of PCR was carried out in the same manner. The amplification product obtained by the second run of PCR was incorporated into a vector (pcDNA3.1 D/V5-His-TOPO (registered trademark), Invitrogen Japan K. K.). By a conventional method, the vector containing this amplification product was introduced to *E. coli* (One Shot TOP10 Competent Cells, Invitrogen Corporation) to transform. This transformed *E. coli* was cultured in an LB agar medium for one day. After the culture, colonies were selected and cultured in an LB liquid medium containing 50 μg/mL of ampicillin. After the culture, the vector was purified using a QIAprep Spin Miniprep Kit (Qiagen K. K.). The base sequence of the insertion site of this vector (SEQ ID NO. 5) was compared with the rat $EP_1$ base sequence (Ptger1) registered as an accession number NM_013100 in well-known database (NCBI), and as a result, they all matched except for a single base. Further, the amino acid sequence translated by the base sequence completely matched the amino acid sequence of the rat $EP_1$ receptor registered as an NCBI accession number NP_037232. Therefore, it was confirmed that the cloned gene sequence was a base sequence of the rat $EP_1$ receptor and the obtained amino acid sequence was that of the rat $EP_1$ receptor. The pcDNA3.1 D/V5-His-TOPO (registered trademark) to which the nucleic acid shown in SEQ ID NO. 5 had been inserted was taken as a rat $EP_1$-expressing vector.

(2) Preparation of Rat $EP_1$ Receptor-Expressing Cells (2-1) COS-1 Cell Culture COS-1 cells (Dainippon Sumitomo Pharma Co., Ltd.) were cultured until it reached confluence in an incubator at 37° C. under a 5% $CO_2$ gas condition, using a D-MEM liquid medium (high glucose and L-glutamine contained, Invitrogen Corporation) to which a penicillin-streptomycin solution (Invitrogen Corporation, final concentration: 100 U/mL as benzylpenicillin; 100 μg/mL as streptomycin) as an antibiotic, MEM nonessential amino acids (Invitrogen Corporation, final Concentration: 0.1 mM), and fetal calf serum (Sanko Junyaku Co., Ltd., final concentration: 10%) were added.

(2-2) COS-1 Cell Subculture

The cells that had reached confluence were stripped with 0.05% trypsin/0.53 mM EDTA 4Na (Invitrogen Japan K. K.) and resuspended in the liquid medium. The resuspended cells were diluted and cultured in the liquid medium at a spread ratio from 1:4 to 1:8.

(2-3) Preparation of Cells for Introduction of Rat $EP_1$-Expressing Vector

The cells that had reached confluence were stripped with 0.05% trypsin/0.53 mM EDTA.4Na, and resuspended in a D-MEM liquid medium (high glucose and L-glutamine contained, Invitrogen Corporation) to which an MEM nonessential amino acid (final concentration: 0.1 mM) and fetal calf serum (final concentration: 10%) were added. In each well of a Poly D-lysine-coated 96-well microplate (BD BioCoat (registered trademark), Nippon Becton Dickinson Company, Ltd.), this resuspended cell suspension culture was prepared to be $5 \times 10^4$ cells/well in 100 μL of the liquid medium, and seeded thereon. After seeding, the cells were cultured in an incubator at 37° C. under a 5% $CO_2$ gas condition. At a point when the cells for introduction of a rat $EP_1$-expressing vector were adhered (about 2 hours after seeding), introduction of the rat $EP_1$-expressing vector was carried out in the following order.

(2-4) Introduction of Rat $EP_1$-Expressing Vector

For introduction of the rat $EP_1$-expressing vector, Lipofectamine 2000 (Invitrogen Japan K. K.) was used. The rat $EP_1$-expressing vector was diluted with OPTI-MEM (registered trademark) I Reduced-Serum Medium (Invitrogen Japan K. K.) to 200 ng/25 μL/well, and at the same time, Lipofectamine 2000 (Invitrogen Japan K. K.n) was also diluted with OPTI-MEM (registered trademark) I Reduced-Serum Medium (Invitrogen Japan K. K.) to 0.5 μL/25 μL/well, followed by incubation at room temperature for 5 minutes. After the incubation for 5 minutes, in order to form a complex of the rat $EP_1$-expressing vector/Lipofectamine 2000, the diluted rat $EP_1$-expressing vector and the diluted Lipofectamine 2000 were mixed and incubated at room temperature for 30 minutes. After the incubation for 30 minutes, the complex of the rat $EP_1$-expressing vector/Lipofectamine 2000 was distributed to the cells for introduction of the rat $EP_1$-expressing vector at 50 μL/well. The cells to which the complex of the rat $EP_1$-expressing vector/Lipofectamine 2000 had been distributed were cultured in an incubator at 37° C. for 20 hours under a 5% $CO_2$ gas condition. After the culture for 20 hours, the cells were used for measurement of an intracellular calcium concentration as rat $EP_1$ receptor-expressing cells.

(3) Study on Inhibitory Effect on Increase in Intracellular Calcium Concentration Using the rat $EP_1$ receptor-expressing cells, the inhibitory effect of each test compound on the increased intracellular calcium concentration induced by prostaglandin $E_2$ was studied in Method A or Method B as shown below.

Method A:

A 10 mM solution of each test compound in dimethyl sulfoxide was diluted with an assay buffer (20 mM HEPES/Hank's Balanced Salt Solution (HBSS), pH 7.2).

The rat $EP_1$ receptor-expressing cells were washed with the assay buffer. 100 μL of a fluorescent calcium indicator (Fluo-4 NW Calcium Assay Kit (Molecular Probes): prepared by the protocol of the same product, Invitrogen Corporation, 2.5 mM probenecid contained) was added to each well, followed by incubation in an incubator at 37° C. for 60 minutes. Then, all the cell supernatants were aspirated and washed with the assay buffer. After the washing, 100 μL of an assay buffer containing 2.5 mM probenecid was added to each well, and the intracellular calcium concentration was measured immediately.

The intracellular calcium concentration was measured as a fluorescent signal using FlexStation (registered trademark) (manufactured by Molecular Devices). 50 μL of each test compound that had been diluted with the assay buffer (final concentrations: 1 nM to 10 μM) was added to each well after 20 seconds from initiating the reading of the fluorescent signal, and the fluorescence signal was measured for 60 seconds. Then, 50 μL of a prostaglandin $E_2$ buffer solution was added to each well (final concentration 10 nM) and the fluorescence signal was measured for 60 seconds.

Method B:

A 10 mM solution of each test compound in dimethyl sulfoxide was diluted in an assay buffer (20 mM HEPES/Hank's Balanced Salt Solution (HBSS), pH 7.2).

The rat $EP_1$ receptor-expressing cells were washed with the assay buffer. 100 μL of a fluorescent calcium indicator (Calcium kit II, Fluo 4 (Dojindo Laboratories): prepared by the protocol of the same product, Invitrogen Japan K. K., 2.5 mM probenecid contained) was added to each well, followed by incubation in an incubator at 37° C. for 60 minutes. Then, the intracellular calcium concentration was measured immediately.

The intracellular calcium concentration was measured as a fluorescent signal using FDSS (registered trademark) 7000 (manufactured by Hamamatsu Photonics K. K.). 50 μL of each test compound (final concentrations: 1 nM to 10 μM) was added to each well after 20 seconds from initiating the reading of the fluorescent signal, and the fluorescence signal was measured for 60 seconds. Then, 50 μL of a prostaglandin $E_2$ buffer solution was added to each well (final concentration 10 nM) and the fluorescence signal was measured for 60 seconds.

In Method A or Method B, as a fluorescent signal obtained by the addition of the prostaglandin $E_2$ with the addition of the assay buffer instead of the test compound was taken as 100% and a signal obtained without the addition of any of the test compound and the prostaglandin $E_2$ was taken as 0%, the concentration of the test compound showing 50% inhibition from the concentration-response curve was taken as an $IC_{50}$ value. As the values of the $EP_1$ receptor antagonism, the obtained $IC_{50}$ values of each test compound were shown in Table 49 below. As Comparative Example 1,3-(5-methyl-2-phenylindol-1-yl)carboxylic acid (Compound 27) described in Patent literature 1 was tested in the similar way. Further, as Comparative Example 2, sodium 6-(6-chloro-3-isobutylindol-1-yl)pyridine-2-carboxylate (Compound 12g) described in Non-Patent literature 5 was tested in the similar way. The results of Comparative Example 1 and Comparative Example 2 were shown in Table 49.

TABLE 49

| Ex. No | $IC_{50}$ (nM) | Method |
|---|---|---|
| 9-1 | 21 | A |
| 9-13 | 89 | A |
| 9-15 | 22 | A |
| 9-21 | 13 | A |
| 9-25 | 35 | A |
| 9-32 | 11 | A |
| 9-35 | 23 | A |
| 9-43 | 13 | A |
| 9-44 | 19 | A |
| 25-9 | 67 | B |
| 25-11 | 34 | B |
| 25-12 | 55 | B |
| 25-13 | 38 | B |
| 25-16 | 39 | B |
| 25-17 | 32 | B |
| 25-18 | 17 | B |
| 25-19 | 36 | B |
| 25-23 | 32 | B |
| 25-26 | 17 | B |
| 25-28 | 28 | B |
| 25-29 | 26 | B |
| 25-31 | 33 | B |
| 25-33 | 58 | B |
| 25-34 | 54 | B |
| 25-36 | 35 | B |
| 25-37 | 27 | B |
| 25-38 | 22 | B |
| 25-39 | 37 | B |
| 25-41 | 25 | B |
| 25-42 | 28 | B |
| 25-44 | 51 | B |
| Comparative Example 1 | >10000 | A |
| Comparative Example 2 | 476 | B |

As shown in Table 49, whereas Comparative Example 1 do not exhibit $EP_1$ receptor antagonism, it is apparent that the compounds of the present invention exhibit potent $EP_1$ receptor antagonism. Further, it is apparent that the compounds of the present invention exhibit potent $EP_1$ receptor antagonism, as also compared with Comparative Example 2.

Test Example 2

Inhibitory Effect of Compound on Sulprostone-Induced Bladder Contraction

Female SD rats were used. Under urethane anesthesia (1.25 g/kg, administered subcutaneously), a tracheal cannula (Size 8, HIBIKI) and a femoral vein cannula for administration (23 G needle-equipped PE50) were inserted thereinto. The bladder cannula (PE50) was inserted from the bladder apex. The bladder cannula was connected to a three-way stopcock, and then, one was connected to a pressure transducer and the other was connected to a syringe filled with saline. Saline was injected to the bladder at an injection rate of 3.6 mL/hour and the bladder contraction pressure was recorded at the time of injection with a recorder (RECTI-HORITZ-8K, NEC Corporation). After 10 minutes from stabilization of the bladder contraction pressure during urination, sulprostone was administered subcutaneously (0.3 mg/kg). Then, at the time point when the bladder contraction pressure became constant, a test agent was administered intravenously (1.0 mg/kg). An average bladder contraction pressure during the 10 minutes period before administration of sulprostone was taken as a baseline (0%). Further, an average bladder contraction pressure during the 10 minutes period before administration of the test agent was taken as a maximum bladder contraction pressure (100%). The average bladder contraction pressures were measured during 5 minutes before and after at 15 minutes and 60 minutes from administration of the test agent. The ratio of this measured value to the maximum bladder contraction pressure was calculated by the following equation and taken as an average bladder contraction rate after administration of the test agent: (Average Bladder Contraction Rate after Administration of Test Agent (%))=(Average Bladder Contraction Pressure after Administration of Test Agent)/(Maximum Bladder Contraction Pressure). In addition, the difference between the maximum bladder contraction rate (100%) and the average bladder contraction rate (%) after administration of the test agent was calculated by the following equation and taken as a bladder contraction inhibition rate of the test agent: (Bladder Contraction Inhibition Rate)=100%−(Average Bladder Contraction Rate after Administration of Test Agent (%)). The results were shown in Table 50.

TABLE 50

| | Bladder Contraction Inhibition Rate (%) | |
|---|---|---|
| Ex No. | 15 Minutes | 60 Minutes |
| 9-21 | 94.5 | 82.8 |
| 16-15 | 85.0 | 54.9 |

From the results above, it was found that the compounds of the present invention had potent and sustained inhibition of the bladder contraction even when administered in vivo.

SEQUENCE LIST FREE TEXT

<Sequence List 1>
SEQ ID NO. 1 is a sequence of a forward primer (5' primer) used for amplification of DNA of SEQ ID NO. 5.
<Sequence List 2>
SEQ ID NO. 2 is a sequence of a reverse primer (3' primer) used for amplification of DNA of SEQ ID NO. 5.
<Sequence List 3>
SEQ ID NO. 3 is a sequence of a forward primer (5' primer) used for amplification of DNA of SEQ ID NO. 5.
<SEQ ID NO. 4>
SEQ ID NO. 4 is a sequence of a reverse primer (3' primer) used for amplification of DNA of SEQ ID NO. 5.
<SEQ ID NO. 5>
SEQ ID NO. 5 is a DNA sequence for expressing a rat EP1 receptor which is amplified using the primers of SEQ ID NO. 1, SEQ ID NO. 2, SEQ ID NO. 3, and SEQ ID NO. 4.

The invention claimed is:

1. A compound represented by the general formula (I) or a pharmaceutically acceptable salt thereof:

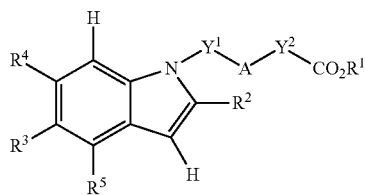

[wherein

A represents a group selected from the group consisting of the following a) to e):

a)
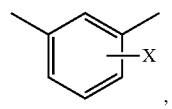

b)
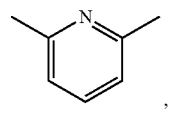

-continued c) 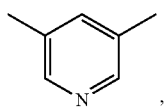

d) 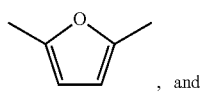, and e) 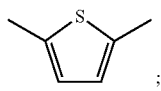;

X represents a hydrogen atom or a halogen atom;
$Y^1$ represents a methylene group;
$Y^2$ represents a single bond;
$R^1$ represents a hydrogen atom;
$R^2$ represents a group selected from the group consisting of the following f) to j):
f) a branched $C_{3-6}$ alkyl group,
g) a halo-$C_{1-6}$ alkyl group,
h) a $C_{3-6}$ cycloalkyl group,
i) a phenyl group, in which the ring is unsubstituted or substituted with 1 to 5 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group, and
j) a 5-membered aromatic heterocyclic group, in which the ring is unsubstituted or substituted with 1 to 3 groups independently selected from the group consisting of: a halogen atom, a $C_{1-6}$ alkyl group, a halo-$C_{1-6}$ alkyl group, a hydroxy-$C_{1-6}$ alkyl group, a $C_{1-6}$ alkoxy group and a cyano group;
$R^3$ represents a halogen atom, a methyl group or a $C_{1-6}$ alkoxy group;
$R^4$ represents a hydrogen atom, a halogen atom, a $C_{1-6}$ alkyl group, or a $C_{1-6}$ alkoxy group; and
$R^5$ represents a hydrogen atom, a halogen atom, a $C_{1-6}$ alkyl group, or a $C_{1-6}$ alkoxy group.

2. The compound as claimed in claim 1 or a pharmaceutically acceptable salt thereof, wherein $R^2$ is a group selected from the group consisting of the following a) to d):
a) a branched $C_{3-6}$ alkyl group,
b) a $C_{3-6}$ cycloalkyl group,
c) a phenyl group, and
d) a 5-membered aromatic;
$R^4$ is a hydrogen atom or a halogen atom; and
$R^5$ is a hydrogen atom.

3. The compound as claimed in claim 1 or a pharmaceutically acceptable salt thereof, wherein $R^3$ is a methoxy group.

4. The compound as claimed in claim 1 or a pharmaceutically acceptable salt thereof, wherein $R^3$ is a fluorine atom.

5. The compound as claimed in claim 1 or a pharmaceutically acceptable salt thereof, wherein $R^2$ is an isopropyl group, an isobutyl group, a sec-butyl group or a 1-ethylpropyl group.

6. The compound as claimed in claim 1 or a pharmaceutically acceptable salt thereof, wherein $R^2$ is a phenyl group or a 5-membered aromatic heterocyclic group.

7. The compound as claimed in claim 6 or a pharmaceutically acceptable salt thereof, wherein $R^2$ is a phenyl group, a 3-thienyl group or a 3-furyl group.

8. The compound as claimed in claim 1 or a pharmaceutically acceptable salt thereof, wherein $R^2$ is a group selected from the group consisting of the following a) to c):

a) 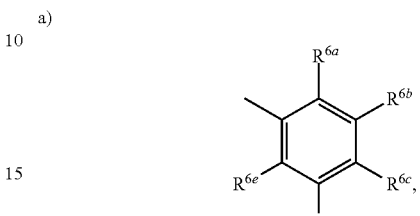

b) 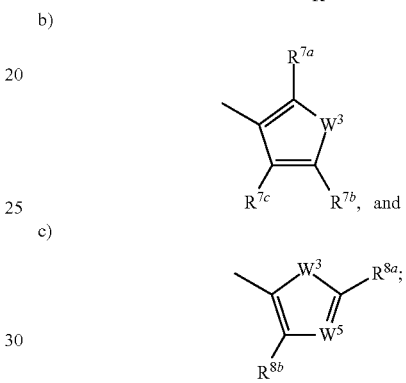, and c)

W3 is an oxygen atom or a sulfur atom;
$W^5$ is a nitrogen atom or $—CR^8=$;
$R^{6a}$, $R^{6b}$, $R^{6c}$, $R^{6d}$ and $R^{6e}$ are each independently a group selected from a hydrogen atom, a halogen atom, a $C_{1-6}$ alkyl group, a halo-$C_{1-6}$ alkyl group, a hydroxy-$C_{1-6}$ alkyl group, a $C_{1-6}$ alkoxy group, or a cyano group, with the proviso that all of $R^{6a}$, $R^{6b}$, $R^{6c}$, $R^{6d}$ and $R^{6e}$ are not simultaneously a hydrogen atom;
$R^{7a}$, $R^{7b}$ and $R^{7c}$ are each independently a hydrogen atom, a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, with the proviso that all of $R^{7a}$, $R^{7b}$, $R^{7c}$ and $R^{7d}$ are not simultaneously a hydrogen atom; and
$R^{8a}$, $R^{8b}$ and $R^{8c}$ are each independently a hydrogen atom, a halogen atom, a $C_{1-6}$ alkyl group, a halo-$C_{1-6}$ alkyl group, a hydroxy-$C_{1-6}$ alkyl group, a $C_{1-6}$ alkoxy group or a cyano group, with the proviso that all of $R^{8a}$, $R^{8b}$ and $R^{8c}$ are not simultaneously a hydrogen atom.

9. A pharmaceutical composition comprising the compound as claimed in claim 1 or a pharmaceutically acceptable salt thereof as an active ingredient.

10. A method for treating lower urinary tract symptoms, selected from the group consisting of urinary urgency, increased daytime frequency, nocturia, urinary incontinence and bladder sensation, comprising administering an effective amount of the compound as claimed in claim 1 or a pharmaceutically acceptable salt thereof.

* * * * *

SEQUENCE LISTING

<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 1
ttggccactg atatgagc                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 2
gctttgggca cattcaca                                                 18

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 3
caccactgat atgagcccct                                               20

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 4
gcctagcttt gggcacatt                                                19

<210> SEQ ID NO 5
<211> LENGTH: 2414
<212> TYPE: DNA
<213> ORGANISM: Rattus norvegicus

<400> SEQUENCE: 5
aacgccaata gggactttcc attgacgtca atgggtggag tatttacggt aaactgccca     60
cttggcagta catcaagtgt atcatatgcc aagtacgccc cctattgacg tcaatgacgg    120
taaatggccc gcctggcatt atgcccagta catgacctta tgggactttc ctacttggca    180
gtacatctac gtattagtca tcgctattac catggtgatg cggttttggc agtacatcaa    240
tgggcgtgga tagcggtttg actcacgggg atttccaagt ctccacccca ttgacgtcaa    300
tgggagtttg ttttggcacc aaaatcaacg ggactttcca aaatgtcgta caactccgc     360 cccattgacg caaatgggcg gtaggcgtgt acggtgggag gtctatataa gcagagctct    420
ctggctaact agagaaccca ctgcttactg gcttatcgaa attaatacga ctcactatag    480
ggagacccaa gctggctagt taagcttggt accgagctcg gatccagtac ccttcaccac    540
tgatatgagc ccctacgggc ttaacctgag cctagtggat gaggcaacaa cgtgtgtaac    600

-continued

```
acccagggtc cccaatacat ctgtggtgct gccaacaggc ggtaacggca catcaccagc    660
gctgcctatc ttctccatga cgctgggtgc tgtgtccaac gtgctggcgc tggcgctgct    720
ggcccaggtt gcaggcagac tgcggcgccg ccgctcgact gccaccttcc tgttgttcgt    780
cgccagcctg cttgccatcg acctagcagg ccatgtgatc ccgggcgcct tggtgcttcg    840
cctgtatact gcaggacgtg cgcccgctgg cggggcctgt catttcctgg gcggctgtat    900
ggtcttcttt ggcctgtgcc cacttttgct tggctgtggc atggccgtgg agcgctgcgt    960
gggtgtcacg cagccgctga tccacgcggc gcgcgtgtcc gtagcccgcg cacgcctggc   1020
actagccctg ctggccgcca tggctttggc agtggcgctg ctgccactag tgcacgtggg   1080
tcactacgag ctacagtacc ctggcacttg gtgtttcatt agccttgggc ctcctggagg   1140
ttggcgccag gcgttgcttg cgggcctctt cgccggcctt ggcctggctg cgctccttgc   1200
cgcactagtg tgtaatacgc tcagcggcct ggcgctcctt cgtgcccgct ggaggcggcg   1260
tcgctctcga cgtttccgag agaacgcagg tcccgatgat cgccgcgct ggggtcccg   1320
tggactccgc ttggcctccg cctcgtctgc gtcatccatc acttcaacca cagctgccct   1380
ccgcagctct cggggaggcg gctccgcgcg cagggttcac gcacacgacg tggaaatggt   1440
gggccagctc gtgggcatca tggtggtttc gtgcatctgc tggagccccc tgctggtatt   1500
ggtggtgttg gccatcgggg gctggaactc taactccctg cagcggccgc tctttctggc   1560
tgtacgcctc gcgtcgtgga accagatcct ggacccatgg gtgtacatcc tgctgcgcca   1620
ggctatgctg cgccaacttc ttcgcctcct acccctgagg ttagtgcca agggtggtcc   1680
aacggagctg agcctaacca agagtgcctg ggaggccagt tcactgcgta gctcccggca   1740
cagtggcttc agccacttgt gaatgtgccc aaagctaggc aagggtcaag acaattctgc   1800
agatatccag cacagtggcg gccgctcgag tctagagggc ccgcggttcg aaggtaagcc   1860
tatccctaac cctctcctcg gtctcgattc tacgcgtacc ggtcatcatc accatcacca   1920
ttgagtttaa acccgctgat cagcctcgac tgtgccttct agttgccagc catctgttgt   1980
ttgcccctcc cccgtgcctt ccttgaccct ggaaggtgcc actcccactg tcctttccta   2040
ataaaatgag gaaattgcat cgcattgtct gagtaggtgt cattctattc tggggggtgg   2100
ggtggggcag gacagcaagg gggaggattg ggaagacaat agcaggcatg ctggggatgc   2160
ggtgggctct atggcttctg aggcggaaag aaccagctgg ggctctaggg ggtatcccca   2220
cgcgccctgt agcggcgcat taagcgcggc gggtgtggtg gttacgcgca gcgtgaccgc   2280
tacacttgcc agcgccctag cgcccgctcc tttcgctttc ttcccttcct ttctcgccac   2340
gttcgccggc tttccccgtc aagctctaaa tcgggggctc cctttagggt tccgatttag   2400
tgctttacgg cacc                                                     2414
```